US008163880B2

(12) United States Patent
Heifetz et al.

(10) Patent No.: US 8,163,880 B2
(45) Date of Patent: Apr. 24, 2012

(54) PRODUCTION OF BIOLOGICALLY ACTIVE PROTEINS

(75) Inventors: Peter Bernard Heifetz, San Diego, CA (US); Blanca Llompart Royo, Barcelona (ES); Pablo Marzábal Luna, Barcelona (ES); Miriam Bastida Virgili, Molins de Rei (ES); Mª Dolores Ludevid Múgica, Sant Just Desvern (ES); Margarita Torrent Quetglas, Barcelona (ES); Kevin James O'Connor, El Prat de Llobregat (ES); Roser Pallisse Bergwerf, Valldoreix (ES); Mª Immaculada Ilop Tous, St. Feliu de Llobregat (ES)

(73) Assignee: ERA Biotech S.A., Barcelona (ES)

( * ) Notice: Subject to any disclaimer, the term of this patent is extended or adjusted under 35 U.S.C. 154(b) by 490 days.

(21) Appl. No.: 11/709,527

(22) Filed: Feb. 22, 2007

(65) Prior Publication Data

US 2007/0243198 A1    Oct. 18, 2007

Related U.S. Application Data

(60) Provisional application No. 60/776,391, filed on Feb. 23, 2006.

(51) Int. Cl.
*C07K 14/37* (2006.01)
*C07K 14/415* (2006.01)
*C07K 14/425* (2006.01)
*C12Q 1/34* (2006.01)
*C12Q 1/26* (2006.01)

(52) U.S. Cl. ........ 530/370; 530/372; 530/373; 530/350; 435/69.7; 435/18; 435/25

(58) Field of Classification Search .................. None
See application file for complete search history.

(56) References Cited

U.S. PATENT DOCUMENTS

| 4,215,040 | A | 7/1980 | Hager |
| 6,642,437 | B1 | 11/2003 | Lemaux et al. |
| 7,575,898 | B2 | 8/2009 | Ludevid Mugica et al. |
| 7,732,569 | B2 | 6/2010 | Decarolis et al. |
| 2005/0244924 | A1 | 11/2005 | Wagner et al. |
| 2006/0121573 | A1* | 6/2006 | Torrent et al. ................ 435/69.1 |
| 2006/0123509 | A1 | 6/2006 | Torrent et al. |
| 2010/0083403 | A1 | 4/2010 | Ludevid Mugica et al. |

FOREIGN PATENT DOCUMENTS

| WO | WO 96/21029 A1 | 7/1996 |
| WO | WO 02/086077 A2 | 10/2002 |
| WO | WO 2004/003207 A1 | 1/2004 |
| WO | WO 2005/113775 A1 | 12/2005 |
| WO | WO 2006/056483 A1 | 6/2006 |
| WO | WO 2006/056484 A1 | 6/2006 |

OTHER PUBLICATIONS

Kim, C.S., et al. 2002 The Plant Cell 14: 655-672.*
Verma et al. 1997 Nature 389: 239-242.*
Anderson, W.F. 1998 Nature 392: 25-30.*
Altschuler, Y., et al., "The N- and C-Terminal Regions Regulate the Transport of Wheat γ-Gliadin through the Endoplasmic Reticulum in Xenopus Oocytes," *Plant Cell* 5: 443-450, American Society for Plant Physiologists, US (1993).
Cameron-Mills, V., "The Structure and Composition of Protein Bodies Purified from Barley Endosperm by Silica Sol Density Gradients," *Carlsberg Res Commun* 45: 557-576, Carlsberg Laboratoriet, DK (1980).
Engelhard, E., et al., "The insect tracheal system: A conduit for the systemic spread of *Autographa californica* M Nuclear polyhedrosis virus," *Proc Natl Acad Sci, USA* 91: 3224-3227, National Academy of Science, US (1994).
Fernández-Carneado, J., et al., "Potential Peptide Carriers: Amphipathic Proline-Rich Peptides Derived from the N-Terminal Domain of γ-Zein," *Angewandte Chemie* 43:1811-1814, Wiley-VCH Verlag GmbH & Co., Germany (2004).
Geli, M., et al., "Two Structural Domains Mediate Two Sequential Events in γ-Zein Targeting: Protein Endoplasmic Reticulum Retention and Protein Body Formation," *Plant Cell* 6: 1911-1922, American Society of Plant Physiologists, US (1994).
Goytia, E., et al., "Production of plum pox virus HC-Pro functionally active for aphid transmission in a transient-expression system," *J Gen Virol* 37: 3413-3423, SGM, GB (2006).
Herman, E. and Larkins, B., "Protein Storage Bodies and Vacuoles," *Plant Cell* 11: 601-613, American Society of Plant Physiologists, US (1999).
Hurkman, W.J., et al., "Subcellular Compartmentalization of Maize Storage Proteins in *Xenopus* Oocytes Injected with Zein Messenger RNAs," *J. Cell Biol.* 89:292-299, The Rockefeller University Press, United States (1981).
Kim, C., et al., "Zein Protein Interactions, Rather Than the Asymmetric Distribution of Zein mRNAs on Endoplasmic Reticulum Membranes, Influence Protein Body Formation in Maize Endosperm," *Plant Cell* 14: 655-672, American Society for Plant Biologists, US (2002).
Luckow, V., et al., "Efficient Generation of Infectious Recombinant Baculoviruses by Site-Specific Transposon-Mediated Insertion of Foreign Genes into a Baculovirus Genome Propagated in *Escherichia coli*," *J Virol* 67(8): 5466-4579, American Society for Microbiology, US (1993).
Ludevid, M., et al., "Subcellular localization of glutelin-2 in maize (*Zea mays* L.) endosperm," *Plant Mol Biol* 3:277-234, Martinus Nijhoff / Dr. W. Junk Publishers, NL (1984).
Mainieri, D., et al., "Zeolin. A New Recombinant Storage Protein Constructed Using Maize γ-Zein and Bean Phaseolin," *Plant Physiol* 136: 3447-3456, American Society of Plant Biologists, US (2004).
Matteucci, M., et al., "Synthesis of Deoxyoligonucleotides on a Polymer Support," *J Am Chem Soc* 103: 3185-3191, American Chemical Society, US (1981).

(Continued)

*Primary Examiner* — Marsha Tsay
(74) *Attorney, Agent, or Firm* — Sterne Kessler Goldstein & Fox P.L.L.C.

(57) ABSTRACT

A fusion protein that is expressed in a recombinant protein body-like assembly (RPBLA) in host eukaryotic cells and organisms is disclosed. More particularly, a biologically active polypeptide fused to a protein sequence that mediates the induction of RPBLA formation is expressed and accumulated in host cells after transformation with an appropriate vector. The eukaryotic host cell does not produce protein bodies in the absence of the fusion protein. Methods for preparing and using the RPBLAs and the fusion protein are also disclosed, as are nucleic acid molecules that encode the fusion proteins.

20 Claims, 9 Drawing Sheets

OTHER PUBLICATIONS

Miflin, B., et al., "The Development of Protein Bodies in the Storage Tissues of Seeds: Subcellular Separations of Homogenates of Barley, Maize, and Wheat Endosperms and of Pea Cotyledons," *J Exp Bot* 32(126): 199-219, Oxford Journals, UK (1981).

Odell, J., et al., "Identification of DNA sequences required for activity of the cauliflower mosaic virus 35S promoter," *Nature* 313: 810-812, Nature Publishing Group, UK (1985).

Paszkowski, J., et al., "Direct gene transfer to plants," *EMBO J* 3(12): 2717-2722, IRL Press Limited, UK (1984).

Philip, R., et al., "Localization of BETA-glucuronidase in Protein Bodies of Transgenic Tobacco Seed by Fusion to an Amino Terminal Sequence of the Soybean Lectin Gene," Plant Sci 137:191-204 (1998).

Richard, G., et al., "Transport and deposition of cereal prolamins," *Plant Physiol Biochem* 34(2): 237-243, Gauthier-Villars, FR (1996).

Rosenberg, N., et al., "Wheat (*Triticum aestivum L.*) γ-Gliadin Accumulates in Dense Protein Bodies within the Endoplasmic Reticulum of Yeast," *Plant Physiol* 102:61-69, American Society of Plant Biologists, US (1993).

Shewry, P., et al., "Cereal seed storage proteins: structures, properties and role in grain utilization," *J Exp Bot* 53(370): 947-958, Oxford Journals, UK (2002).

Shukla, R., et al., "Zein: the industrial protein from corn," *Industrial Crops and Products* 13: 171-192, Elsevier Science B.V., UK (2001).

Sojikul, P., et al., "A plant signal peptide-hepatitis B surface antigen fusion protein with enhanced stability and immunogenicity expressed in plant cells," *Proc Natl Acad Sci, USA* 100(5): 2209-2214, National Academy of Science, US (2003).

Takagi, H., et al., "A rice-based edible vaccine expressing multiple T cell epitopes induces oral tolerance for inhibition of Th2-mediated IgE responses," *Proc Natl Acad Sci, USA* 102(48): 17525-17530, National Academy of Science, US (2005).

Thompson, S., et al., "High-Level Expression of a Wheat LMW Glutenin Subunit Using a Baculovirus System," *J. Agric. Food Chem.* 42:426-431, America Chemical Society, United States (1994).

Torrent, M., et al., Eukaryotic protein production in designed storage organelles,: *BMC Biology* 7:5, pp. 1-14, BioMed Central Ltd., UK (2009).

Torrent, M., et al., "In maize, glutelin-2 and low molecular weight zeins are synthesized by membrane-bound polyribosomes and translocated into microsomal membranes," *Plant Mol Biol* 7: 393-403, Martinus Nijhoff Publishers, NL (1986).

Torrent, M., et al., "Lysine-rich modified γ-zeins accumulate in protein bodies of transiently transformed maize endosperms," *Plant Mol Biol* 34(1): 139-149, Kluwe Academic Publishers, BE (1997).

Torrent, M., et al., "Role of structural domains for maize γ-zein retention in *Xenopus* Oocytes," *Planta* 192: 512-518, Springer-Verlag, DE (1994).

Wallace, J., et al., "Aggregation of Lysine-Containing Zeins into Protein Bodies in *Xenopus* Oocytes," *Science* 240: 662-664, American Association for the Advancement of Science, US (1988).

Yang, D., et al., "Expression and localization of human lysozyme in the endosperm of transgenic rice," *Planta* 216: 597-603, Springer-Verlag, DE (2003).

Office Action mailed Apr. 9, 2008, in U.S. Appl. No. 11/288,853, Torrent et al., filed Nov. 29, 2005.

Office Action mailed Jan. 14, 2009, in U.S. Appl. No. 11/288,853, Torrent et al., filed Nov. 29, 2005.

Office Action mailed Jun. 25, 2010, in U.S. Appl. No. 11/288,853, Torrent et al., filed Nov. 29, 2005.

Office Action mailed Mar. 17, 2010, in U.S. Appl. No. 11/288,853, Torrent et al., filed Nov. 29, 2005.

Office Action mailed Aug. 19, 2008, in U.S. Appl. No. 11/289,264, Torrent et al., filed Nov. 29, 2005.

Office Action mailed Mar. 31, 2010, in U.S. Appl. No. 11/289,264, Torrent et al., filed Nov. 29, 2005.

Office Action mailed Nov. 23, 2010, in U.S. Appl. No. 11/289,264, Torrent et al., filed Nov. 29, 2005.

International Search Report for International Application No. PCT/EP2007/001606, European Patent Office, Netherlands, mailed on Nov. 23, 2007.

International Search Report for International Application No. PCT/EP2005/012878, European Patent Office, Netherlands, mailed on Mar. 21, 2006.

International Search Report for International Application No. PCT/EP2005/012877, European Patent Office, Netherlands, mailed on Apr. 21, 2006.

García-Fruitós, E., et al., "Aggregation as bacterial inclusion bodies does not imply inactivation of enzymes and fluorescent proteins," *Microb. Cell Fact.* 4:1-6, BioMed Central, England (2005).

Greenberg, S. and Grinstein, S., "Phagocytosis and innate immunity," *Curr. Opin. Immunol.* 14:136-145, Elsevier Science Ltd., England (2002).

Marston, F.A.O., "The purification of eukaryotic polypeptides synthesized in *Escherichia coli*," *Biochem. J.* 240:1-12, the Biochemical Society, England (1986).

Öhlschläger, P., et al., "An improved rearranged Human Papillomavirus Type 16 E7 DNA vaccine candidate (HPV-16 E7SH) induces an E7 wildtype-specific T cell response," *Vaccine* 24:2880-2893, Elsevier Science B.V., Netherlands (2006).

Richard, G., et al., "Transport and deposition of cereal prolamins," *Plant Physiol. Biochem.* 34:237-243, Elsevier Science, France (1996).

Simon, R., et al., "Two Closely Related Wheat Storage Proteins Follow a Markedly Different Subcellular Route in *Xenopus laevis* Oocytes," *The Plant Cell* 2:941-950, American Society of Plant Physiologists, United States (1990).

\* cited by examiner

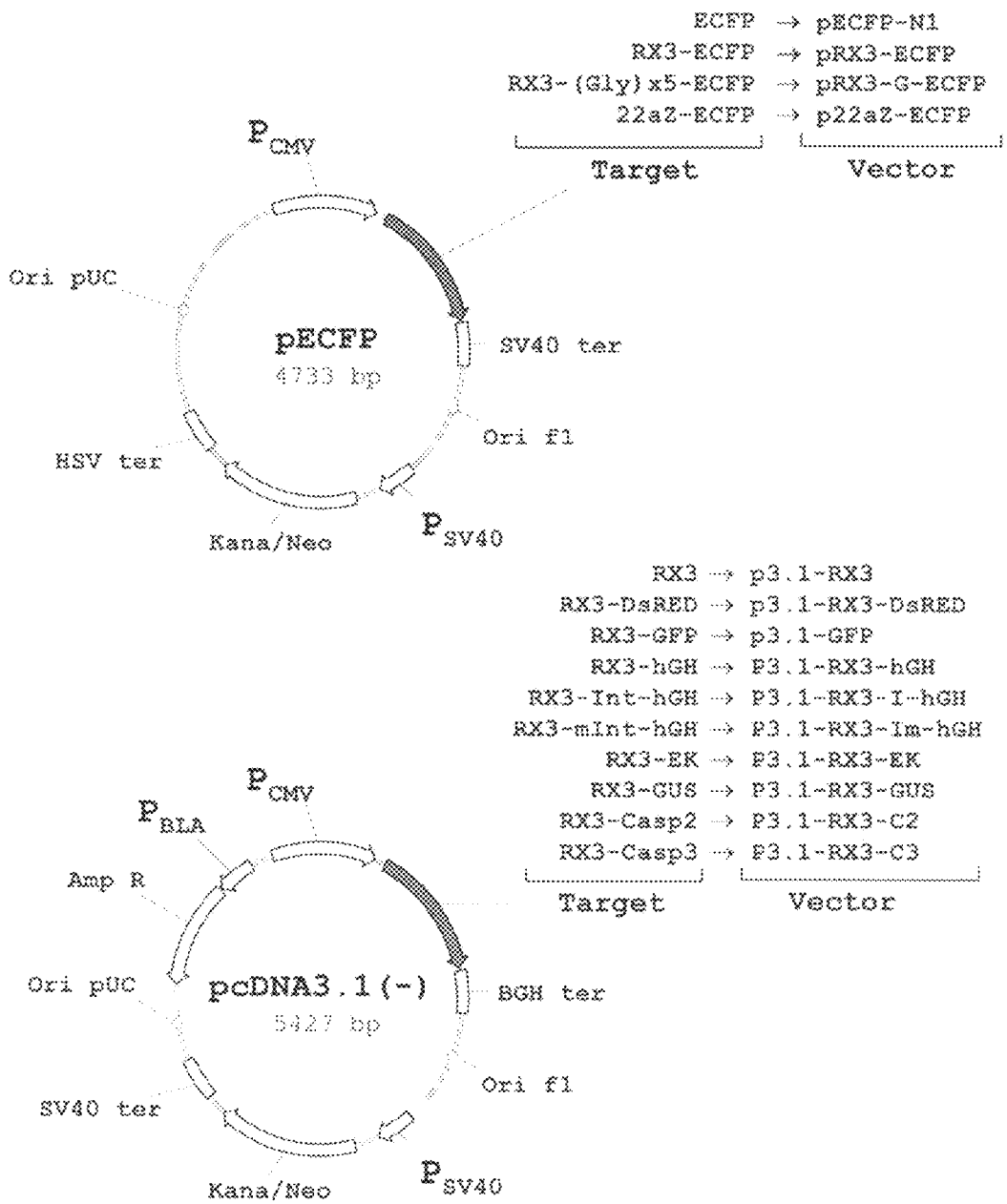

Fig. 1
Fig. 1B
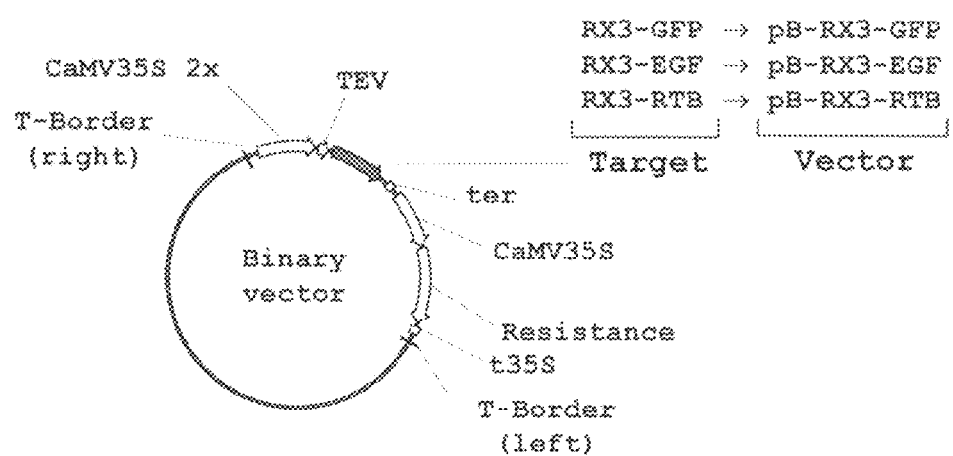
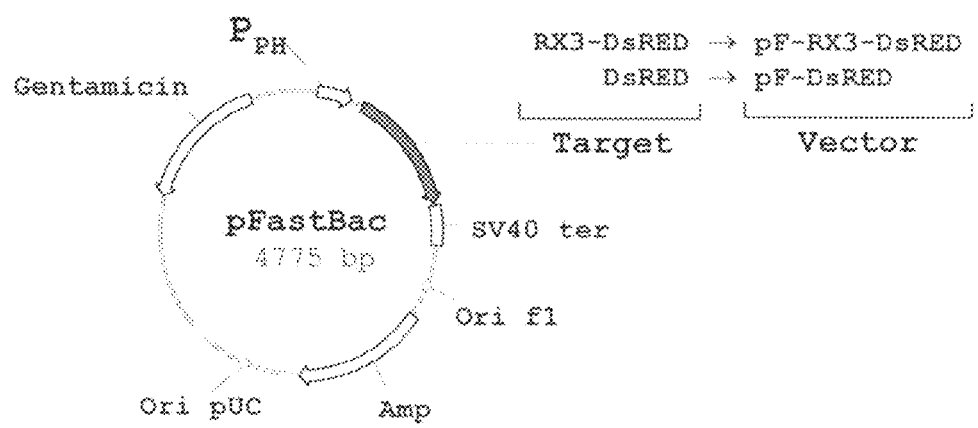

Fig. 2
Fig. 2A
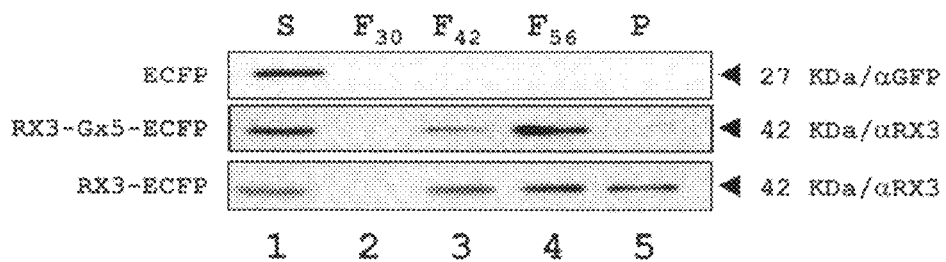
Fig. 2B
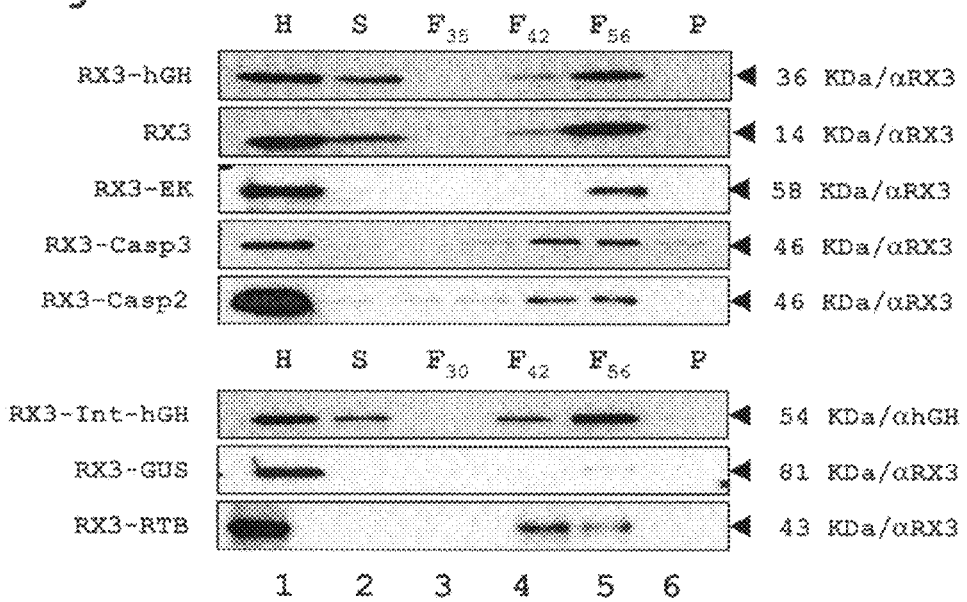
Fig. 2C
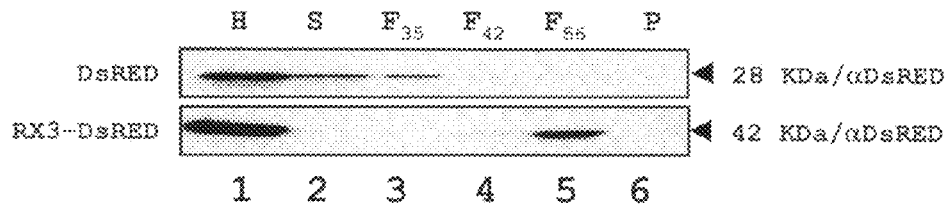

Fig. 6
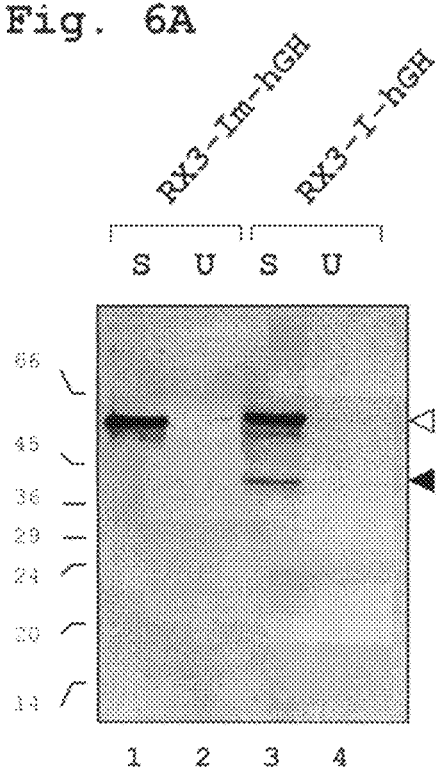
Fig. 6A
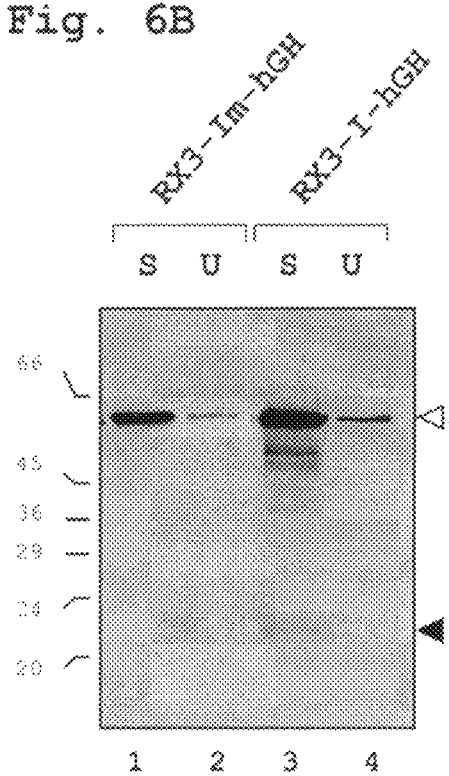
Fig. 6B
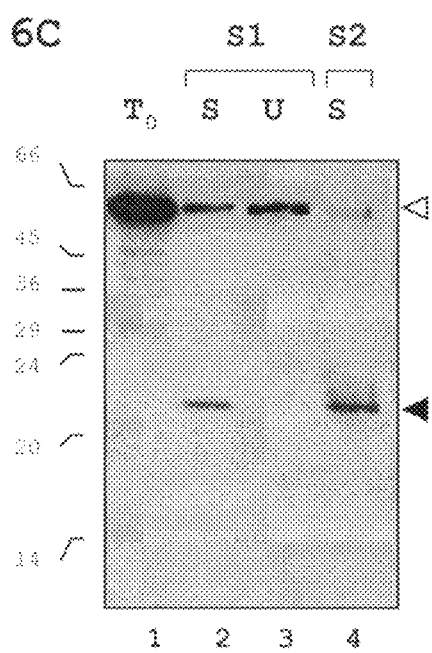
Fig. 6C

Fig. 7
Fig. 7A
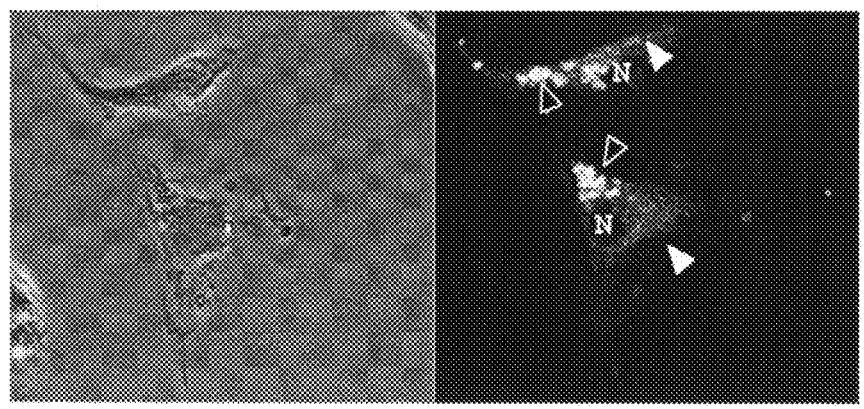
Fig. 7B
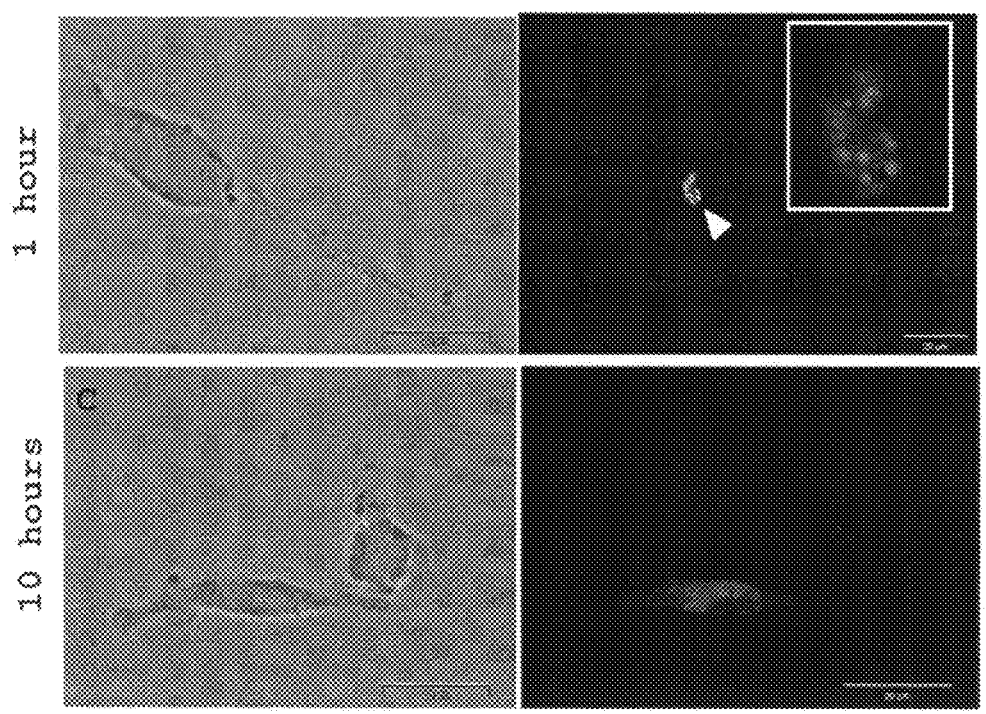

Fig. 8
Fig. 8A
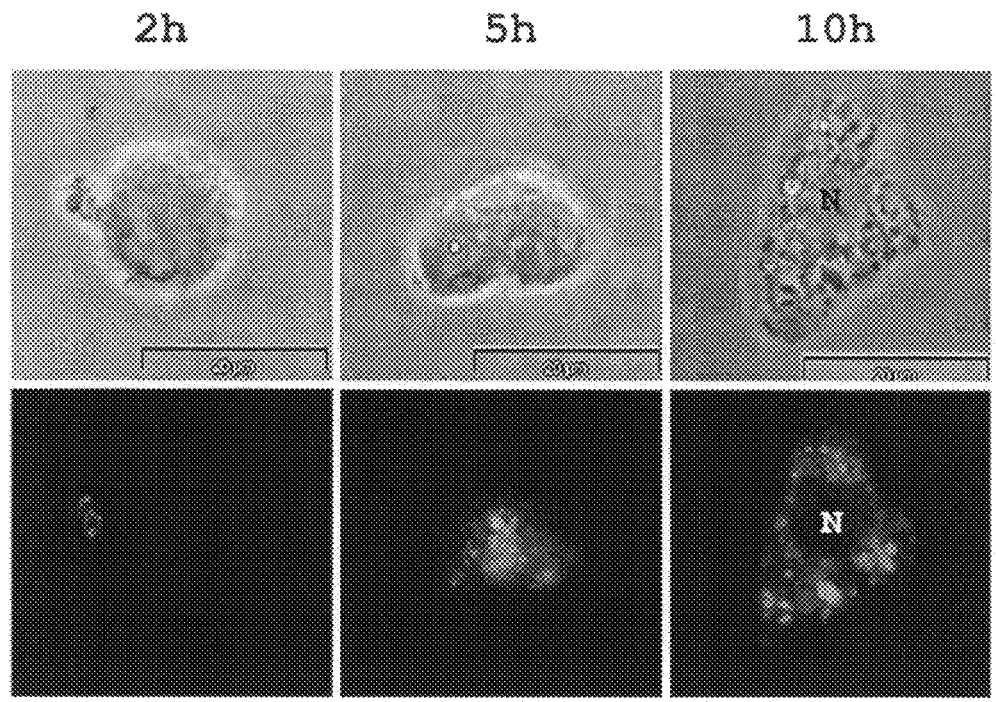
Fig. 8B
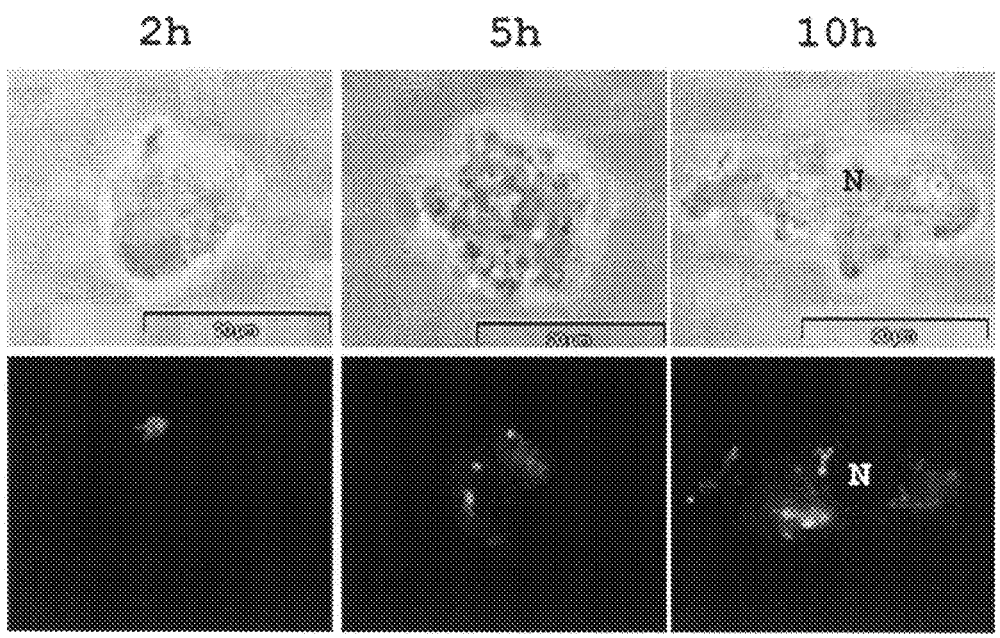

```
                        SEQUENCE LISTING

<160> NUMBER OF SEQ ID NOS: 74

<210> SEQ ID NO 1
<211> LENGTH: 6
<212> TYPE: PRT
<213> ORGANISM: Artificial sequence
<220> FEATURE:
<223> OTHER INFORMATION: part of Promoter 2xCaMV

<400> SEQUENCE: 1

Pro Pro Pro Val His Leu
1               5

<210> SEQ ID NO 2
<211> LENGTH: 53
<212> TYPE: PRT
<213> ORGANISM: Artificial sequence
<220> FEATURE:
<223> OTHER INFORMATION: RX3 query aa sequence

<400> SEQUENCE: 2

Pro Pro Pro Pro Val His Leu Pro Pro Val His Leu Pro Pro Pro
1               5                   10                  15

Val His Leu Pro Pro Pro Val His Leu Pro Pro Pro Val His Leu Pro
                20                  25                  30

Pro Pro Val His Leu Pro Pro Pro Val His Val Pro Pro Val His
            35                  40                  45

Leu Pro Pro Pro Pro
    50

<210> SEQ ID NO 3
<211> LENGTH: 65
<212> TYPE: PRT
<213> ORGANISM: Artificial sequence
<220> FEATURE:
<223> OTHER INFORMATION: Alpha zein aa sequence

<400> SEQUENCE: 3

Gln Gln Gln Gln Gln Phe Leu Pro Ala Leu Ser Gln Leu Asp Val Val
1               5                   10                  15

Asn Pro Val Ala Tyr Leu Gln Gln Gln Leu Leu Ala Ser Asn Pro Leu
                20                  25                  30

Ala Leu Ala Asn Val Ala Ala Tyr Gln Gln Gln Gln Leu Gln Gln
            35                  40                  45

Phe Leu Pro Ala Leu Ser Gln Leu Ala Met Val Asn Pro Ala Ala Tyr
        50                  55                  60

Leu
65

<210> SEQ ID NO 4
<211> LENGTH: 70
<212> TYPE: PRT
<213> ORGANISM: Artificial sequence
<220> FEATURE:
<223> OTHER INFORMATION: rice prolamin query aa sequence

<400> SEQUENCE: 4
```

```
Gln Gln Val Leu Ser Pro Tyr Asn Glu Phe Val Arg Gln Gln Tyr Gly
1               5                   10                  15

Ile Ala Ala Ser Pro Phe Leu Gln Ser Ala Thr Phe Gln Leu Arg Asn
            20                  25                  30

Asn Gln Val Trp Gln Gln Leu Ala Leu Val Ala Gln Gln Ser His Cys
        35                  40                  45

Gln Asp Ile Asn Ile Val Gln Ala Ile Ala Gln Gln Leu Gln Leu Gln
    50                  55                  60

Gln Phe Gly Asp Leu Tyr
65                  70

<210> SEQ ID NO 5
<211> LENGTH: 672
<212> TYPE: DNA
<213> ORGANISM: Maize

<400> SEQUENCE: 5
atgagggtgt tgctcgttgc cctcgctctc ctggctctcg ctgcgagcgc cacctccacg      60
catacaagcg gcggctgcgg ctgccagcca ccgccgccgg ttcatctacc gccgccggtg     120
catctgccac ctccggttca cctgccacct ccggtgcatc tcccaccgcc ggtccacctg     180
ccgccgccgg tccacctgcc accgccggtc catgtgccgc cgccggttca tctgccgccg     240
ccaccatgcc actaccctac tcaaccgccc ggcctcagc ctcatcccca gccacaccca      300
tgcccgtgcc aacagccgca tccaagcccg tgccagctgc agggaacctg cggcgttggc     360
agcaccccga tcctgggcca gtgcgtcgag tttctgaggc atcagtgcag cccgacggcg     420
acgccctact gctcgcctca gtgccagtcg ttgcggcagc agtgttgcca gcagctcagg     480
caggtggagc cgcagcaccg gtaccaggcg atcttcggct tggtcctcca gtccatcctg     540
cagcagcagc cgcaaaagcg gccaggtcgcg gggctgttgg cggcgcagat agcgcagcaa    600
ctgacggcga tgtgcggcct gcagcagccg actccatgcc cctacgctgc tgccggcggt    660
gtcccccacg cc                                                         672

<210> SEQ ID NO 6
<211> LENGTH: 224
<212> TYPE: PRT
<213> ORGANISM: Maize

<400> SEQUENCE: 6

Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Val His Leu Pro Pro Val His Leu
        35                  40                  45

Pro Pro Pro Val His Leu Pro Pro Val His Leu Pro Pro Val
    50                  55                  60

His Leu Pro Pro Val His Val Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110

Leu Gln Gly Thr Cys Gly Val Gly Ser Thr Pro Ile Leu Gly Gln Cys
        115                 120                 125
```

-continued

```
Val Glu Phe Leu Arg His Gln Cys Ser Pro Thr Ala Thr Pro Tyr Cys
            130                 135                 140

Ser Pro Gln Cys Gln Ser Leu Arg Gln Gln Cys Gln Gln Leu Arg
145                 150                 155                 160

Gln Val Glu Pro Gln His Arg Tyr Gln Ala Ile Phe Gly Leu Val Leu
                165                 170                 175

Gln Ser Ile Leu Gln Gln Pro Gln Ser Gly Gln Val Ala Gly Leu
            180                 185                 190

Leu Ala Ala Gln Ile Ala Gln Gln Leu Thr Ala Met Cys Gly Leu Gln
                195                 200                 205

Gln Pro Thr Pro Cys Pro Tyr Ala Ala Ala Gly Gly Val Pro His Ala
            210                 215                 220
```

<210> SEQ ID NO 7
<211> LENGTH: 339
<212> TYPE: DNA
<213> ORGANISM: Artificial sequence
<220> FEATURE:
<223> OTHER INFORMATION: RX3 DNA sequence

<400> SEQUENCE: 7

```
atgagggtgt tgctcgttgc cctcgctctc ctggctctcg ctgcgagcgc cacctccacg    60
catacaagcg gcggctgcgg ctgccagcca ccgccgccgg ttcatctacc gccgccggtg   120
catctgccac ctccggttca cctgccacct ccggtgcatc tcccaccgcc ggtccacctg   180
ccgccgccgg tccacctgcc accgccggtc catgtgccgc cgccggttca tctgccgccg   240
ccaccatgcc actaccctac tcaaccgccc ggcctcagc ctcatcccca gccacaccca    300
tgcccgtgcc aacagccgca tccaagcccg tgccagacc                           339
```

<210> SEQ ID NO 8
<211> LENGTH: 113
<212> TYPE: PRT
<213> ORGANISM: Artificial sequence
<220> FEATURE:
<223> OTHER INFORMATION: RX3 aa

<400> SEQUENCE: 8

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro Pro
            20                  25                  30

Pro Val His Leu Pro Pro Pro Val His Leu Pro Pro Pro Val His Leu
                35                  40                  45

Pro Pro Pro Val His Leu Pro Pro Pro Val His Leu Pro Pro Pro Val
50                  55                  60

His Leu Pro Pro Pro Val His Val Pro Pro Pro Val His Leu Pro Pro
65                  70                  75                  80

Pro Pro Cys His Tyr Pro Thr Gln Pro Pro Arg Pro Gln Pro His Pro
                85                  90                  95

Gln Pro His Pro Cys Pro Cys Gln Gln Pro His Pro Ser Pro Cys Gln
            100                 105                 110

Tyr
```

<210> SEQ ID NO 9
<211> LENGTH: 240
<212> TYPE: DNA
<213> ORGANISM: Artificial sequence
<220> FEATURE:
<223> OTHER INFORMATION: R3 DNA

<400> SEQUENCE: 9

```
atgagggtgt tgctcgttgc cctcgctctc ctggctctcg ctgcgagcgc cacctccacg    60
catacaagcg gcggctgcgg ctgccagcca ccgccgccgg ttcatctacc gccgccggtg   120
catctgccac ctccggttca cctgccacct ccggtgcatc tcccaccgcc ggtccacctg   180
ccgccgccgg tccacctgcc accgccggtc catgtgccgc cgccggttca tctgccgccg   240
```

<210> SEQ ID NO 10
<211> LENGTH: 92
<212> TYPE: PRT
<213> ORGANISM: Artificial sequence
<220> FEATURE:
<223> OTHER INFORMATION: chemically synthesized

<400> SEQUENCE: 10

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro
            20                  25                  30

Pro Val His Leu Pro Pro Pro Val His Leu Pro Pro Val His Leu
            35                  40                  45

Pro Pro Pro Val His Leu Pro Pro Val His Leu Pro Pro Val
        50                  55                  60

His Leu Pro Pro Val His Val Pro Pro Val His Leu Pro Pro
65                  70                  75                  80

Pro Pro Cys His Tyr Pro Thr Gln Pro Pro Arg Tyr
                85                  90
```

<210> SEQ ID NO 11
<211> LENGTH: 213
<212> TYPE: DNA
<213> ORGANISM: Artificial sequence
<220> FEATURE:
<223> OTHER INFORMATION: P4 DNA

<400> SEQUENCE: 11

```
atgagggtgt tgctcgttgc cctcgctctc ctggctctcg ctgcgagcgc cacctccacg    60
catacaagcg gcggctgcgg ctgccagcca ccgccgccgg ttcatctgcc gccgccacca   120
tgccactacc ctacacaacc gccccggcct cagcctcatc cccagccaca cccatgcccg   180
tgccaacagc cgcatccaag cccgtgccag acc                                213
```

<210> SEQ ID NO 12
<211> LENGTH: 71
<212> TYPE: PRT
<213> ORGANISM: Artificial sequence
<220> FEATURE:
<223> OTHER INFORMATION: P4 protein

<400> SEQUENCE: 12

```
Met Arg Val Leu Leu Val Ala Leu Ala Leu Leu Ala Leu Ala Ala Ser
1               5                   10                  15

Ala Thr Ser Thr His Thr Ser Gly Gly Cys Gly Cys Gln Pro Pro
            20                  25                  30

Pro Val His Leu Pro Pro Pro Cys His Tyr Pro Thr Gln Pro Pro
            35                  40                  45

Arg Pro Gln Pro His Pro Gln Pro His Pro Cys Pro Cys Gln Gln Pro
        50                  55                  60

His Pro Ser Pro Cys Gln Tyr
```

<210> SEQ ID NO 13
<211> LENGTH: 180
<212> TYPE: DNA
<213> ORGANISM: Artificial sequence
<220> FEATURE:
<223> OTHER INFORMATION: X10 DNA

<400> SEQUENCE: 13

```
atgagggtgt tgctcgttgc cctcgctctc ctggctctcg ctgcgagcgc cacctccacg    60
catacaagcg gcggctgcgg ctgccaatgc cactaccta tcaaccgcc ccggcctcag    120 cctcatcccc agccacaccc atgcccgtgc caacagccgc atccaagccc gtgccagacc    180
```

<210> SEQ ID NO 14
<211> LENGTH: 60
<212> TYPE: PRT
<213> ORGANISM: Artificial sequence
<220> FEATURE:
<223> OTHER INFORMATION: X10 protein

<400> SEQUENCE: 14

```
Met Arg Val Leu Leu Val Ala Leu Ala Leu Leu Ala Leu Ala Ala Ser
 1               5                  10                  15

Ala Thr Ser Thr His Thr Ser Gly Gly Cys Gly Cys Gln Cys His Tyr
            20                  25                  30

Pro Thr Gln Pro Pro Arg Pro Gln Pro His Pro Gln Pro His Pro Cys
        35                  40                  45

Pro Cys Gln Gln Pro His Pro Ser Pro Cys Gln Tyr
    50                  55                  60
```

<210> SEQ ID NO 15
<211> LENGTH: 150
<212> TYPE: PRT
<213> ORGANISM: Artificial sequence
<220> FEATURE:
<223> OTHER INFORMATION: rP13 protein

<400> SEQUENCE: 15

```
Met Lys Ile Ile Phe Val Phe Ala Leu Leu Ala Ile Ala Ala Cys Ser
 1               5                  10                  15

Ala Ser Ala Gln Phe Asp Val Leu Gly Gln Ser Tyr Arg Gln Tyr Gln
            20                  25                  30

Leu Gln Ser Pro Val Leu Leu Gln Gln Gln Val Leu Ser Pro Tyr Asn
        35                  40                  45

Glu Phe Val Arg Gln Gln Tyr Gly Ile Ala Ala Ser Pro Phe Leu Gln
    50                  55                  60

Ser Ala Thr Phe Gln Leu Arg Asn Asn Gln Val Trp Gln Gln Leu Ala
65                  70                  75                  80

Leu Val Ala Gln Gln Ser His Cys Gln Asp Ile Asn Ile Val Gln Ala
                85                  90                  95

Ile Ala Gln Gln Leu Gln Leu Gln Gln Phe Gly Asp Leu Tyr Phe Asp
            100                 105                 110

Arg Asn Leu Ala Gln Ala Gln Ala Leu Leu Ala Phe Asn Val Pro Ser
        115                 120                 125

Arg Tyr Gly Ile Tyr Pro Arg Tyr Tyr Gly Ala Pro Ser Thr Ile Thr
    130                 135                 140

Thr Leu Gly Gly Val Leu
145                 150
```

<210> SEQ ID NO 16
<211> LENGTH: 450
<212> TYPE: DNA
<213> ORGANISM: Artificial sequence
<220> FEATURE:
<223> OTHER INFORMATION: rP13 DNA

<400> SEQUENCE: 16

```
atgaagatca ttttcgtctt tgctctcctt gctattgctg catgcagcgc ctctgcgcag      60
tttgatgttt taggtcaaag ttataggcaa tatcagctgc agtcgcctgt cctgctacag     120
caacaggtgc ttagcccata taatgagttc gtaaggcagc agtatggcat agcggcaagc     180
cccttcttgc aatcagctac gtttcaactg agaaacaacc aagtctggca acagctcgcg     240
ctggtggcgc aacaatctca ctgtcaggac attaacattg ttcaggccat agcgcagcag     300
ctacaactcc agcagtttgg tgatctctac tttgatcgga atctggctca agctcaagct     360
ctgttggctt taacgtgcc atctagatat ggtatctacc taggtacta tggtgcaccc      420
agtaccatta ccaccttgg cggtgtcttg                                       450
```

<210> SEQ ID NO 17
<211> LENGTH: 144
<212> TYPE: PRT
<213> ORGANISM: Artificial sequence
<220> FEATURE:
<223> OTHER INFORMATION: 22aZt protein

<400> SEQUENCE: 17

```
Met Ala Thr Lys Ile Leu Ala Leu Leu Ala Leu Leu Ala Leu Phe Val
 1               5                  10                  15

Ser Ala Thr Asn Ala Phe Ile Ile Pro Gln Cys Ser Leu Ala Pro Ser
            20                  25                  30

Ala Ile Ile Pro Gln Phe Leu Pro Pro Val Thr Ser Met Gly Phe Glu
        35                  40                  45

His Leu Ala Val Gln Ala Tyr Arg Leu Gln Gln Ala Leu Ala Ala Ser
    50                  55                  60

Val Leu Gln Gln Pro Ile Asn Gln Leu Gln Gln Ser Leu Ala His
65                  70                  75                  80

Leu Thr Ile Gln Thr Ile Ala Thr Gln Gln Gln Gln Phe Leu Pro
                85                  90                  95

Ala Leu Ser Gln Leu Asp Val Val Asn Pro Val Ala Tyr Leu Gln Gln
            100                 105                 110

Gln Leu Leu Ala Ser Asn Pro Leu Ala Leu Ala Asn Val Ala Ala Tyr
        115                 120                 125

Gln Gln Gln Gln Gln Leu Gln Gln Phe Leu Pro Ala Leu Ser Gln Leu
    130                 135                 140
```

<210> SEQ ID NO 18
<211> LENGTH: 432
<212> TYPE: DNA
<213> ORGANISM: Artificial sequence
<220> FEATURE:
<223> OTHER INFORMATION: 22aZt DNA

<400> SEQUENCE: 18

```
atggctacca agatattagc cctccttgcg cttcttgccc tttttgtgag cgcaacaaat      60
gcgttcatta ttccacaatg ctcacttgct cctagtgcca ttataccaca gttcctccca     120
ccagttactt caatgggctt cgaacaccta gctgtgcaag cctacaggct acaacaagcg     180
cttgcggcaa gcgtcttaca acaaccaatt aaccaattgc aacaacaatc cttggcacat     240
```

```
ctaaccatac aaaccatcgc aacgcaacag caacaacagt tcctaccagc actgagccaa    300
ctagatgtgg tgaaccctgt cgcctacttg caacagcagc tgcttgcatc caacccactt    360
gctctggcaa acgtagctgc ataccaacaa caacaacaat tgcagcagtt tctgccagcg    420
ctcagtcaac ta                                                        432
```

<210> SEQ ID NO 19
<211> LENGTH: 283
<212> TYPE: PRT
<213> ORGANISM: Artificial sequence
<220> FEATURE:
<223> OTHER INFORMATION: gamm gliadin precursor

<400> SEQUENCE: 19

```
Asn Met Gln Val Asp Pro Ser Gly Gln Val Gln Trp Pro Gln Gln Gln
1               5                   10                  15

Pro Phe Pro Gln Pro Gln Gln Pro Phe Cys Gln Gln Pro Gln Arg Thr
            20                  25                  30

Ile Pro Gln Pro His Gln Thr Phe His His Gln Pro Gln Gln Thr Phe
        35                  40                  45

Pro Gln Pro Gln Gln Thr Tyr Pro His Gln Pro Gln Gln Phe Pro
    50                  55                  60

Gln Thr Gln Gln Pro Gln Gln Pro Phe Pro Gln Pro Gln Gln Thr Phe
65                  70                  75                  80

Pro Gln Gln Pro Gln Leu Pro Phe Pro Gln Pro Gln Gln Pro Phe
                85                  90                  95

Pro Gln Pro Gln Gln Pro Gln Pro Phe Pro Gln Ser Gln Gln Pro
            100                 105                 110

Gln Gln Pro Phe Pro Gln Pro Gln Gln Phe Pro Gln Pro Gln Gln
        115                 120                 125

Pro Gln Gln Ser Phe Pro Gln Gln Gln Pro Ala Ile Gln Ser Phe
    130                 135                 140

Leu Gln Gln Gln Met Asn Pro Cys Lys Asn Phe Leu Leu Gln Gln Cys
145                 150                 155                 160

Asn His Val Ser Leu Val Ser Ser Leu Val Ser Ile Ile Leu Pro Arg
                165                 170                 175

Ser Asp Cys Gln Val Met Gln Gln Cys Cys Gln Gln Leu Ala Gln
            180                 185                 190

Ile Pro Gln Gln Leu Gln Cys Ala Ala Ile His Ser Val Ala His Ser
        195                 200                 205

Ile Ile Met Gln Gln Glu Gln Gln Gln Gly Val Pro Ile Leu Arg Pro
    210                 215                 220

Leu Phe Gln Leu Ala Gln Gly Leu Gly Ile Ile Gln Pro Gln Gln Pro
225                 230                 235                 240

Ala Gln Leu Glu Gly Ile Arg Ser Leu Val Leu Lys Thr Leu Pro Thr
                245                 250                 255

Met Cys Asn Val Tyr Val Pro Pro Asp Cys Ser Thr Ile Asn Val Pro
            260                 265                 270

Tyr Ala Asn Ile Asp Ala Gly Ile Gly Gly Gln
        275                 280
```

<210> SEQ ID NO 20
<211> LENGTH: 2086
<212> TYPE: DNA
<213> ORGANISM: Artificial sequence
<220> FEATURE:
<223> OTHER INFORMATION: gamma gliadin DNA M36999

<400> SEQUENCE: 20

```
gcatgcattg tcaaagtttg tgaagtagaa ttaataacct tttggttatt gatcactgta      60
tgtatcttag atgtcccgta gcaacggtaa gggcattcac ctagtactag tccaatatta     120
attaataact tgcacagaat tacaaccatt gacataaaaa ggaaatatga tgagtcatgt     180
attgattcat gttcaacatt actacccttg acataaaaga agaatttgac gagtcgtatt     240
agcttgttca tcttaccatc atactatact gcaagctagt ttaaaaaga atyaaagtcc      300
agaatgaaca gtagaatagc ctgatctatc tttaacaaca tgcacaagaa tacaaattta     360
gtcccttgca agctatgaag atttggttta tgcctaacaa catgataaac ttagatccaa     420
aaggaatgca atctagataa ttgtttgact tgtaaagtcg ataagatgag tcagtgccaa     480
ttataaagtt ttcgccactc ttagatcata tgtacaataa aaaggcaact ttgctgacca     540
ctccaaaagt acgtttgtat gtagtgccac caaacacaac acaccaaata atcagtttga     600
taagcatcga atcactttaa aaagtgaaag aaataatgaa agaaaccta accatggtag      660
ctataaaaag cctgtaatat gtacactcca taccatcatc catccttcac acaactagag     720
cacaagcatc aaatccaagt aagtattagt taacgcaaat ccaccatgaa gaccttactc     780
atcctaacaa tccttgcgat ggcaacaacc atcgccaccg ccaatatgca agtcgacccc     840
agcggccaag tacaatggcc acaacaacaa ccattccccc agcccaaca accattctgc      900
cagcaaccac aacgaactat tccccaaccc catcaaacat tccaccatca accacaacaa     960
acatttcccc aaccccaaca acataccccc catcaaccac aacaacaatt tccccagacc    1020
caacaaccac aacaaccatt tccccagccc caacaaacat tccccccaaca accccaacta    1080
ccatttcccc aacaaccccca acaaccattc ccccagcctc agcaaccccca acaaccattt    1140
ccccagtcac aacaaccaca acaaccttt ccccagcccc aacaacaatt tccgcagccc    1200
caacaaccac aacaatcatt ccccccaacaa caacaaccgg cgattcagtc atttctacaa    1260
caacagatga accctgcaa gaatttcctc ttgcagcaat gcaaccatgt gtcattggtg     1320
tcatctctcg tgtcaataat tttgccacga agtgattgcc aggtgatgca gcaacaatgt     1380
tgccaacaac tagcacaaat tcctcaacag ctccagtgcg cagccatcca cagcgtcgcg     1440
cattccatca tcatgcaaca agaacaacaa caaggcgtgc cgatcctgcg gccactattt     1500
cagctcgccc agggtctggg tatcatccaa cctcaacaac cagctcaatt ggaggggatc     1560
aggtcattgg tattgaaaac tcttccaacc atgtgcaacg tgtatgtgcc acctgactgc     1620
tccaccatca acgtaccata tgccaacata gacgctggca ttggtggcca atgaaaaatg    1680
caagatcatc attgcttagc tgatgcacca atcgttgtag cgatgacaaa taaagtggtg    1740
tgcaccatca tgtgtgaccc cgaccagtgc tagttcaagc ttgggaataa aagacaaaca    1800
aagttcttgt ttgctagcat tgcttgtcac tgttacattc acttttttatt tcgatgttca    1860
tccctaaccg caatcctagc cttacacgtc aatagctagc tgcttgtgct ggcaggttac    1920
tatataatct atcaattaat ggtcgaccta ttaatccaag taataggcta ttgatagact    1980
gctcccaagc cgaccgagca cctatcagtt acgatttct tgaacattgc acactataat     2040
aattcaacgt atttcaacct ctagaagtaa agggcatttt agtagc                   2086
```

<210> SEQ ID NO 21
<211> LENGTH: 537
<212> TYPE: DNA
<213> ORGANISM: Artificial sequence
<220> FEATURE:
<223> OTHER INFORMATION: beta zein AF371264 DNA

<400> SEQUENCE: 21

```
atgaagatgg tcatcgttct cgtcgtgtgc ctggctctgt cagctgccag cgcctctgca      60
atgcagatgc cctgcccctg cgcggggctg cagggcttgt acggcgctgg cgccggcctg     120
acgacgatga tgggcgccgg cgggctgtac ccctacgcgg agtacctgag gcagccgcag     180
tgcagcccgc tggcggcggc gccctactac gccgggtgtg ggcagccgag cgccatgttc     240
cagccgctcc ggcaacagtg ctgccagcag cagatgagga tgatggacgt gcagtccgtc     300
gcgcagcagc tgcagatgat gatgcagctt gagcgtgccg ctgccgccag cagcagcctg     360
tacgagccag ctctgatgca gcagcagcag cagctgctgg cagcccaggg tctcaacccc     420
atggccatga tgatggcgca gaacatgccg gccatgggtg gactctacca gtaccagctg     480
cccagctacc gcaccaaccc ctgtggcgtc tccgctgcca ttccgcccta ctactga        537
```

<210> SEQ ID NO 22
<211> LENGTH: 178
<212> TYPE: PRT
<213> ORGANISM: Artificial sequence
<220> FEATURE:
<223> OTHER INFORMATION: beta zein AF371264 protein

<400> SEQUENCE: 22

```
Met Lys Met Val Ile Val Leu Val Val Cys Leu Ala Leu Ser Ala Ala
1               5                   10                  15
Ser Ala Ser Ala Met Gln Met Pro Cys Pro Cys Ala Gly Leu Gln Gly
                20                  25                  30
Leu Tyr Gly Ala Gly Ala Gly Leu Thr Thr Met Met Gly Ala Gly Gly
            35                  40                  45
Leu Tyr Pro Tyr Ala Glu Tyr Leu Arg Gln Pro Gln Cys Ser Pro Leu
        50                  55                  60
Ala Ala Ala Pro Tyr Tyr Ala Gly Cys Gly Gln Pro Ser Ala Met Phe
65                  70                  75                  80
Gln Pro Leu Arg Gln Gln Cys Cys Gln Gln Gln Met Arg Met Met Asp
                85                  90                  95
Val Gln Ser Val Ala Gln Gln Leu Gln Met Met Met Gln Leu Glu Arg
                100                 105                 110
Ala Ala Ala Ala Ser Ser Ser Leu Tyr Glu Pro Ala Leu Met Gln Gln
            115                 120                 125
Gln Gln Gln Leu Leu Ala Ala Gln Gly Leu Asn Pro Met Ala Met Met
        130                 135                 140
Met Ala Gln Asn Met Pro Ala Met Gly Gly Leu Tyr Gln Tyr Gln Leu
145                 150                 155                 160
Pro Ser Tyr Arg Thr Asn Pro Cys Gly Val Ser Ala Ala Ile Pro Pro
                165                 170                 175
Tyr Tyr
```

<210> SEQ ID NO 23
<211> LENGTH: 453
<212> TYPE: DNA
<213> ORGANISM: Artificial sequence
<220> FEATURE:
<223> OTHER INFORMATION: delta zein AF371266

<400> SEQUENCE: 23

```
atggcagcca agatgcttgc attgttcgct ctcctagctc tttgtgcaag cgccactagt      60
gcgacgcata ttccagggca cttgccacca gtcatgccat gggtaccat gaacccatgc     120
```

```
atgcagtact gcatgatgca acaggggctt gccagcttga tggcgtgtcc gtccctgatg      180
ctgcagcaac tgttggcctt accgcttcag acgatgccag tgatgatgcc acagatgatg      240
acgcctaaca tgatgtcacc attgatgatg ccgagcatga tgtcaccaat ggtcttgccg      300
agcatgatgt cgcaaatgat gatgccacaa tgtcactgcg acgccgtctc gcagattatg      360
ctgcaacagc agttaccatt catgttcaac ccaatggcca tgacgattcc acccatgttc      420
ttacagcaac cctttgttgg tgctgcattc tag                                    453
```

<210> SEQ ID NO 24
<211> LENGTH: 150
<212> TYPE: PRT
<213> ORGANISM: Artificial sequence
<220> FEATURE:
<223> OTHER INFORMATION: delta zein AF371266 protein

<400> SEQUENCE: 24

```
Met Ala Ala Lys Met Leu Ala Leu Phe Ala Leu Leu Ala Leu Cys Ala
1               5                   10                  15

Ser Ala Thr Ser Ala Thr His Ile Pro Gly His Leu Pro Pro Val Met
            20                  25                  30

Pro Leu Gly Thr Met Asn Pro Cys Met Gln Tyr Cys Met Met Gln Gln
        35                  40                  45

Gly Leu Ala Ser Leu Met Ala Cys Pro Ser Leu Met Leu Gln Gln Leu
    50                  55                  60

Leu Ala Leu Pro Leu Gln Thr Met Pro Val Met Met Pro Gln Met Met
65                  70                  75                  80

Thr Pro Asn Met Met Ser Pro Leu Met Met Pro Ser Met Met Ser Pro
                85                  90                  95

Met Val Leu Pro Ser Met Met Ser Gln Met Met Met Pro Gln Cys His
            100                 105                 110

Cys Asp Ala Val Ser Gln Ile Met Leu Gln Gln Gln Leu Pro Phe Met
        115                 120                 125

Phe Asn Pro Met Ala Met Thr Ile Pro Pro Met Phe Leu Gln Gln Pro
    130                 135                 140

Phe Val Gly Ala Ala Phe
145                 150
```

<210> SEQ ID NO 25
<211> LENGTH: 19
<212> TYPE: PRT
<213> ORGANISM: Artificial sequence
<220> FEATURE:
<223> OTHER INFORMATION: gamma zein signal peptide

<400> SEQUENCE: 25

```
Met Arg Val Leu Leu Val Ala Leu Ala Leu Leu Ala Leu Ala Ala Ser
1               5                   10                  15

Ala Thr Ser
```

<210> SEQ ID NO 26
<211> LENGTH: 20
<212> TYPE: PRT
<213> ORGANISM: Artificial sequence
<220> FEATURE:
<223> OTHER INFORMATION: alpha gliadin signal peptide

<400> SEQUENCE: 26

```
Met Lys Thr Phe Leu Ile Leu Val Leu Leu Ala Ile Val Ala Thr Thr
1               5                   10                  15
```

Ala Thr Thr Ala
            20

<210> SEQ ID NO 27
<211> LENGTH: 21
<212> TYPE: PRT
<213> ORGANISM: Artificial sequence
<220> FEATURE:
<223> OTHER INFORMATION: gamma gliadin signal peptide

<400> SEQUENCE: 27

Met Lys Thr Leu Leu Ile Leu Thr Ile Leu Ala Met Ala Ile Thr Ile
1               5                   10                  15

Gly Thr Ala Asn Met
            20

<210> SEQ ID NO 28
<211> LENGTH: 25
<212> TYPE: PRT
<213> ORGANISM: Artificial sequence
<220> FEATURE:
<223> OTHER INFORMATION: PR10 signal sequence

<400> SEQUENCE: 28

Met Asn Phe Leu Lys Ser Phe Pro Phe Tyr Ala Phe Leu Cys Phe Gly
1               5                   10                  15

Gln Tyr Phe Val Ala Val Thr His Ala
            20                  25

<210> SEQ ID NO 29
<211> LENGTH: 720
<212> TYPE: DNA
<213> ORGANISM: Artificial sequence
<220> FEATURE:
<223> OTHER INFORMATION: ECFP DNA

<400> SEQUENCE: 29
atggtgagca agggcgagga gctgttcacc ggggtggtgc ccatcctggt cgagctggac      60
ggcgacgtaa acggccacaa gttcagcgtg tccggcgagg gcgagggcga tgccacctac     120
ggcaagctga ccctgaagtt catctgcacc accggcaagc tgcccgtgcc ctggcccacc     180
ctcgtgacca ccctgacctg gggcgtgcag tgcttcagcc gctacccga ccacatgaag      240 cagcacgact tcttcaagtc cgccatgccc gaaggctacg tccaggagcg caccatcttc     300
ttcaaggacg acggcaacta caagacccgc gccgaggtga agttcgaggg cgacaccctg     360
gtgaaccgca tcgagctgaa gggcatcgac ttcaaggagg acggcaacat cctggggcac     420
aagctggagt acaactacat cagccacaac gtctatatca ccgccgacaa gcagaagaac     480
ggcatcaagg ccaacttcaa gatccgccac aacatcgagg acggcagcgt gcagctcgcc     540
gaccactacc agcagaacac ccccatcggc gacggccccg tgctgctgcc cgacaaccac     600
tacctgagca cccagtccgc cctgagcaaa gaccccaacg agaagcgcga tcacatggtc     660
ctgctggagt tcgtgaccgc cgccgggatc actctcggca tggacgagct gtacaagtaa     720

<210> SEQ ID NO 30
<211> LENGTH: 239
<212> TYPE: PRT
<213> ORGANISM: Artificial sequence
<220> FEATURE:
<223> OTHER INFORMATION: ECFP protein

<400> SEQUENCE: 30

Met Val Ser Lys Gly Glu Glu Leu Phe Thr Gly Val Val Pro Ile Leu

```
 1               5                  10                  15
Val Glu Leu Asp Gly Asp Val Asn Gly His Lys Phe Ser Val Ser Gly
                20                  25                  30

Glu Gly Glu Gly Asp Ala Thr Tyr Gly Lys Leu Thr Leu Lys Phe Ile
            35                  40                  45

Cys Thr Thr Gly Lys Leu Pro Val Pro Trp Pro Thr Leu Val Thr Thr
 50                  55                  60

Leu Thr Trp Gly Val Gln Cys Phe Ser Arg Tyr Pro Asp His Met Lys
 65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
 130                 135                 140

Asn Tyr Ile Ser His Asn Val Tyr Ile Thr Ala Asp Lys Gln Lys Asn
145                 150                 155                 160

Gly Ile Lys Ala Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
                180                 185                 190

Pro Val Leu Leu Pro Asp Asn His Tyr Leu Ser Thr Gln Ser Ala Leu
            195                 200                 205

Ser Lys Asp Pro Asn Glu Lys Arg Asp His Met Val Leu Leu Glu Phe
 210                 215                 220

Val Thr Ala Ala Gly Ile Thr Leu Gly Met Asp Glu Leu Tyr Lys
225                 230                 235

<210> SEQ ID NO 31
<211> LENGTH: 1854
<212> TYPE: DNA
<213> ORGANISM: Artificial sequence
<220> FEATURE:
<223> OTHER INFORMATION: GUS 1381 DNA

<400> SEQUENCE: 31
atggtagatc tgactagttt acgtcctgta gaaaccccaa cccgtgaaat caaaaaactc      60
gacggcctgt gggcattcag tctggatcgc gaaaactgtg aattgatca gcgttggtgg     120 gaaagcgcgt tacaagaaag ccgggcaatt gctgtgccag gcagttttaa cgatcagttc     180
gccgatgcag atattcgtaa ttatgcgggc aacgtctggt atcagcgcga agtctttata     240
ccgaaaggtt gggcaggcca cgtatcgtg ctgcgtttcg atgcggtcac tcattacggc     300
aaagtgtggg tcaataatca ggaagtgatg agcatcagg gcggctatac gccatttgaa     360
gccgatgtca cgccgtatgt tattgccggg aaaagtgtac gtatcaccgt tgtgtgaac     420 aacgaactga ctggcagac tatcccgccg ggaatggtga ttaccgacga aaacggcaag     480
aaaaagcagt cttacttcca tgatttcttt aactatgccg gaatccatcg cagcgtaatg     540
ctctacacca cgccgaacac ctgggtggac gatatcaccg tggtgacgca tgtcgcgcaa     600
gactgtaacc acgcgtctgt tgactggcag gtggtggcca atggtgatgt cagcgttgaa     660
ctgcgtgatg cggatcaaca ggtggttgca actggacaag gcactagcgg acttttgcaa     720
gtggtgaatc cgcacctctg gcaaccgggt gaaggttatc tctatgaact gtgcgtcaca     780
```

```
gccaaaagcc agacagagtg tgatatctac ccgcttcgcg tcggcatccg gtcagtggca    840
gtgaagggcc aacagttcct gattaaccac aaaccgttct actttactgg ctttggtcgt    900
catgaagatg cggacttacg tggcaaagga ttcgataacg tgctgatggt gcacgaccac    960
gcattaatgg actggattgg ggccaactcc taccgtacct cgcattaccc ttacgctgaa   1020
gagatgctcg actgggcaga tgaacatggc atcgtggtga ttgatgaaac tgctgctgtc   1080
ggctttcagc tgtctttagg cattggtttc gaagcgggca acaagccgaa agaactgtac   1140
agcgaagagg cagtcaacgg ggaaactcag caagcgcact acaggcgat  taaagagctg   1200 atagcgcgtg acaaaaacca cccaagcgtg gtgatgtgga gtattgccaa cgaaccggat   1260
acccgtccgc aaggtgcacg ggaatatttc gcgccactgg cggaagcaac gcgtaaactc   1320
gacccgacgc gtccgatcac ctgcgtcaat gtaatgttct gcgacgctca caccgatacc   1380
atcagcgatc tctttgatgt gctgtgcctg aaccgttatt acggatggta tgtccaaagc   1440
ggcgatttgg aaacggcaga gaaggtactg gaaaaagaac ttctggcctg caggagaaa    1500 ctgcatcagc cgattatcat caccgaatac ggcgtggata cgttagccgg gctgcactca   1560
atgtacaccg acatgtggag tgaagagtat cagtgtgcat ggctggatat gtatcaccgc   1620
gtctttgatc gcgtcagcgc cgtcgtcggt gaacaggtat ggaatttcgc cgattttgcg   1680
acctcgcaag gcatattgcg cgttggcggt aacaagaaag ggatcttcac tcgcgaccgc   1740
aaaccgaagt cggcggcttt tctgctgcaa aaacgctgga ctggcatgaa cttcggtgaa   1800
aaaccgcagc agggaggcaa acaagctagc caccaccacc accaccacgt gtga         1854
```

<210> SEQ ID NO 32
<211> LENGTH: 617
<212> TYPE: PRT
<213> ORGANISM: Artificial sequence
<220> FEATURE:
<223> OTHER INFORMATION: GUS 1381 protein

<400> SEQUENCE: 32

```
Met Val Asp Leu Thr Ser Leu Arg Pro Val Glu Thr Pro Thr Arg Glu
1               5                   10                  15

Ile Lys Lys Leu Asp Gly Leu Trp Ala Phe Ser Leu Asp Arg Glu Asn
                20                  25                  30

Cys Gly Ile Asp Gln Arg Trp Trp Glu Ser Ala Leu Gln Glu Ser Arg
            35                  40                  45

Ala Ile Ala Val Pro Gly Ser Phe Asn Asp Gln Phe Ala Asp Ala Asp
        50                  55                  60

Ile Arg Asn Tyr Ala Gly Asn Val Trp Tyr Gln Arg Glu Val Phe Ile
65                  70                  75                  80

Pro Lys Gly Trp Ala Gly Gln Arg Ile Val Leu Arg Phe Asp Ala Val
                85                  90                  95

Thr His Tyr Gly Lys Val Trp Val Asn Asn Gln Glu Val Met Glu His
            100                 105                 110

Gln Gly Gly Tyr Thr Pro Phe Glu Ala Asp Val Thr Pro Tyr Val Ile
        115                 120                 125

Ala Gly Lys Ser Val Arg Ile Thr Val Cys Val Asn Asn Glu Leu Asn
    130                 135                 140

Trp Gln Thr Ile Pro Pro Gly Met Val Ile Thr Asp Glu Asn Gly Lys
145                 150                 155                 160

Lys Lys Gln Ser Tyr Phe His Asp Phe Phe Asn Tyr Ala Gly Ile His
                165                 170                 175

Arg Ser Val Met Leu Tyr Thr Thr Pro Asn Thr Trp Val Asp Asp Ile
```

```
                180             185             190
Thr Val Val Thr His Val Ala Gln Asp Cys Asn His Ala Ser Val Asp
            195             200             205
Trp Gln Val Val Ala Asn Gly Asp Val Ser Val Glu Leu Arg Asp Ala
            210             215             220
Asp Gln Gln Val Val Ala Thr Gly Gln Gly Thr Ser Gly Thr Leu Gln
225             230             235             240
Val Val Asn Pro His Leu Trp Gln Pro Gly Glu Gly Tyr Leu Tyr Glu
            245             250             255
Leu Cys Val Thr Ala Lys Ser Gln Thr Glu Cys Asp Ile Tyr Pro Leu
            260             265             270
Arg Val Gly Ile Arg Ser Val Ala Val Lys Gly Gln Gln Phe Leu Ile
            275             280             285
Asn His Lys Pro Phe Tyr Phe Thr Gly Phe Gly Arg His Glu Asp Ala
            290             295             300
Asp Leu Arg Gly Lys Gly Phe Asp Asn Val Leu Met Val His Asp His
305             310             315             320
Ala Leu Met Asp Trp Ile Gly Ala Asn Ser Tyr Arg Thr Ser His Tyr
            325             330             335
Pro Tyr Ala Glu Glu Met Leu Asp Trp Ala Asp Glu His Gly Ile Val
            340             345             350
Val Ile Asp Glu Thr Ala Ala Val Gly Phe Gln Leu Ser Leu Gly Ile
            355             360             365
Gly Phe Glu Ala Gly Asn Lys Pro Lys Glu Leu Tyr Ser Glu Ala
            370             375             380
Val Asn Gly Glu Thr Gln Gln Ala His Leu Gln Ala Ile Lys Glu Leu
385             390             395             400
Ile Ala Arg Asp Lys Asn His Pro Ser Val Val Met Trp Ser Ile Ala
            405             410             415
Asn Glu Pro Asp Thr Arg Pro Gln Gly Ala Arg Glu Tyr Phe Ala Pro
            420             425             430
Leu Ala Glu Ala Thr Arg Lys Leu Asp Pro Thr Arg Pro Ile Thr Cys
            435             440             445
Val Asn Val Met Phe Cys Asp Ala His Thr Asp Thr Ile Ser Asp Leu
            450             455             460
Phe Asp Val Leu Cys Leu Asn Arg Tyr Tyr Gly Trp Tyr Val Gln Ser
465             470             475             480
Gly Asp Leu Glu Thr Ala Glu Lys Val Leu Glu Lys Glu Leu Leu Ala
            485             490             495
Trp Gln Glu Lys Leu His Gln Pro Ile Ile Ile Thr Glu Tyr Gly Val
            500             505             510
Asp Thr Leu Ala Gly Leu His Ser Met Tyr Thr Asp Met Trp Ser Glu
            515             520             525
Glu Tyr Gln Cys Ala Trp Leu Asp Met Tyr His Arg Val Phe Asp Arg
            530             535             540
Val Ser Ala Val Val Gly Glu Gln Val Trp Asn Phe Ala Asp Phe Ala
545             550             555             560
Thr Ser Gln Gly Ile Leu Arg Val Gly Gly Asn Lys Lys Gly Ile Phe
            565             570             575
Thr Arg Asp Arg Lys Pro Lys Ser Ala Ala Phe Leu Leu Gln Lys Arg
            580             585             590
Trp Thr Gly Met Asn Phe Gly Glu Lys Pro Gln Gln Gly Gly Lys Gln
            595             600             605
```

Ala Ser His His His His His Val
     610               615

<210> SEQ ID NO 33
<211> LENGTH: 2041
<212> TYPE: DNA
<213> ORGANISM: Artificial sequence
<220> FEATURE:
<223> OTHER INFORMATION: GUS 1391Z DNA

<400> SEQUENCE: 33

```
atggtagatc tgagggtaaa tttctagttt ttctccttca ttttcttggt taggaccctt      60
ttctcttttt attttttga  gctttgatct ttctttaaac tgatctattt tttaattgat     120
tggttatggt gtaaatatta catagcttta actgataatc tgattacttt atttcgtgtg     180
tctatgatga tgatgatagt tacagaaccg acgactcgtc cgtcctgtag aacgtgaaat     240
caaaaaactc gacggcctgt gggcattcag tctggatcgc gaaaactgtg gaattgatca     300
gcgttggtgg gaaagcgcgt tacaagaaag ccgggcaatt gctgtgccag gcagttttaa     360
cgatcagttc gccgatgcag atattcgtaa ttatgcgggc aacgtctggt atcagcgcga     420
agtctttata ccgaaaggtt gggcaggcca gcgtatcgtg ctgcgtttcg atgcggtcac     480
tcattacggc aaagtgtggg tcaataatca ggaagtgatg gagcatcagg cggctatac      540
gccatttgaa gccgatgtca cgccgtatgt tattgccggg aaaagtgtac gtatcaccgt     600
ttgtgtgaac aacgaactga actggcagac tatcccgccg ggaatggtga ttaccgacga     660
aaacggcaag aaaaagcagt cttacttcca tgatttcttt aactatgccg gaatccatcg     720
cagcgtaatg ctctacacca cgccgaacac ctgggtggac gatatcaccg tggtgacgca     780
tgtcgcgcaa gactgtaacc acgcgtctgt tgactggcag gtggtggcca atggtgatgt     840
cagcgttgaa ctgcgtgatg cggatcaaca ggtggttgca actggacaag cactagcgg      900
gactttgcaa gtggtgaatc cgcacctctg gcaaccgggt gaaggttatc tctatgaact     960
gtgcgtcaca gccaaaagcc agacagagtg tgatatctac ccgcttcgcg tcggcatccg    1020
gtcagtggca gtgaagggcg aacagttcct gattaaccac aaaccgttct actttactgg    1080
ctttggtcgt catgaagatg cggacttacg tggcaaagga ttcgataacg tgctgatggt    1140
gcacgaccac gcattaatgg actggattgg ggccaactcc taccgtacct cgcattaccc    1200
ttacgctgaa gagatgctcg actgggcaga tgaacatggc atcgtggtga ttgatgaaac    1260
tgctgctgtc ggctttaacc tctctttagg cattggtttc gaagcgggca caagccgaa     1320
agaactgtac agcgaagagg cagtcaacgg ggaaactcag caagcgcact acaggcgat     1380
taaagagctg atagcgcgtg acaaaaacca cccaagcgtg gtgatgtgga gtattgccaa    1440
cgaaccggat acccgtccgc aagtgcacgg gaatatttcg ccactggcgg aagcaacgcg    1500
taaactcgac ccgacgcgtc cgatcacctg cgtcaatgta atgttctgcg acgctcacac    1560
cgataccatc agcgatctct tgatgtgct  gtgcctgaac cgttattacg atggtatgt     1620
ccaaagcggc gatttggaaa cggcagaaa  ggtactggaa aaagaacttc tggcctggca    1680
ggagaaactg catcagccga ttatcatcac cgaatacggc gtggatacgt agccgggct     1740
gcactcaatg tacaccgaca tgtggagtga agagtatcag tgtgcatggc tggatatgta    1800
tcaccgcgtc tttgatcgcg tcagcgccgt cgtcggtgaa caggtatgga atttcgccga    1860
ttttgcgacc tcgcaaggca tattgcgcgt tggcggtaac aagaaaggga tcttcactcg    1920
cgaccgcaaa ccgaagtcgg cggctttttct gctgcaaaaa cgctggactg gcatgaactt    1980
cggtgaaaaa ccgcagcagg gaggcaaaca agctagccac caccaccacc accacgtgtg    2040
```

-continued

<210> SEQ ID NO 34
<211> LENGTH: 617
<212> TYPE: PRT
<213> ORGANISM: Artificial sequence
<220> FEATURE:
<223> OTHER INFORMATION: GUS 1391Z protein

<400> SEQUENCE: 34

```
Met Val Asp Leu Arg Val Asn Arg Arg Leu Val Arg Pro Val Glu Arg
1               5                   10                  15

Glu Ile Lys Lys Leu Asp Gly Leu Trp Ala Phe Ser Leu Asp Arg Glu
            20                  25                  30

Asn Cys Gly Ile Asp Gln Arg Trp Trp Glu Ser Ala Leu Gln Glu Ser
        35                  40                  45

Arg Ala Ile Ala Val Pro Gly Ser Phe Asn Asp Gln Phe Ala Asp Ala
    50                  55                  60

Asp Ile Arg Asn Tyr Ala Gly Asn Val Trp Tyr Gln Arg Glu Val Phe
65                  70                  75                  80

Ile Pro Lys Gly Trp Ala Gly Gln Arg Ile Val Leu Arg Phe Asp Ala
                85                  90                  95

Val Thr His Tyr Gly Lys Val Trp Val Asn Asn Gln Glu Val Met Glu
            100                 105                 110

His Gln Gly Gly Tyr Thr Pro Phe Glu Ala Asp Val Thr Pro Tyr Val
        115                 120                 125

Ile Ala Gly Lys Ser Val Arg Ile Thr Val Cys Val Asn Asn Glu Leu
    130                 135                 140

Asn Trp Gln Thr Ile Pro Pro Gly Met Val Ile Thr Asp Glu Asn Gly
145                 150                 155                 160

Lys Lys Lys Gln Ser Tyr Phe His Asp Phe Phe Asn Tyr Ala Gly Ile
                165                 170                 175

His Arg Ser Val Met Leu Tyr Thr Thr Pro Asn Thr Trp Val Asp Asp
            180                 185                 190

Ile Thr Val Val Thr His Val Ala Gln Asp Cys Asn His Ala Ser Val
        195                 200                 205

Asp Trp Gln Val Val Ala Asn Gly Asp Val Ser Val Glu Leu Arg Asp
    210                 215                 220

Ala Asp Gln Gln Val Val Ala Thr Gly Gln Gly Thr Ser Gly Thr Leu
225                 230                 235                 240

Gln Val Val Asn Pro His Leu Trp Gln Pro Gly Glu Gly Tyr Leu Tyr
                245                 250                 255

Glu Leu Cys Val Thr Ala Lys Ser Gln Thr Glu Cys Asp Ile Tyr Pro
            260                 265                 270

Leu Arg Val Gly Ile Arg Ser Val Ala Val Lys Gly Glu Gln Phe Leu
        275                 280                 285

Ile Asn His Lys Pro Phe Tyr Phe Thr Gly Phe Gly Arg His Glu Asp
    290                 295                 300

Ala Asp Leu Arg Gly Lys Gly Phe Asp Asn Val Leu Met Val His Asp
305                 310                 315                 320

His Ala Leu Met Asp Trp Ile Gly Ala Asn Ser Tyr Arg Thr Ser His
                325                 330                 335

Tyr Pro Tyr Ala Glu Glu Met Leu Asp Trp Ala Asp Glu His Gly Ile
            340                 345                 350

Val Val Ile Asp Glu Thr Ala Ala Val Gly Phe Asn Leu Ser Leu Gly
```

```
                355               360               365
Ile Gly Phe Glu Ala Gly Asn Lys Pro Lys Glu Leu Tyr Ser Glu Glu
    370               375               380

Ala Val Asn Gly Glu Thr Gln Gln Ala His Leu Gln Ala Ile Lys Glu
385               390               395               400

Leu Ile Ala Arg Asp Lys Asn His Pro Ser Val Val Met Trp Ser Ile
            405               410               415

Ala Asn Glu Pro Asp Thr Arg Pro Gln Val His Gly Asn Ile Ser Pro
            420               425               430

Leu Ala Glu Ala Thr Arg Lys Leu Asp Pro Thr Arg Pro Ile Thr Cys
            435               440               445

Val Asn Val Met Phe Cys Asp Ala His Thr Asp Thr Ile Ser Asp Leu
    450               455               460

Phe Asp Val Leu Cys Leu Asn Arg Tyr Tyr Gly Trp Tyr Val Gln Ser
465               470               475               480

Gly Asp Leu Glu Thr Ala Glu Lys Val Leu Lys Glu Leu Leu Ala
                485               490               495

Trp Gln Glu Lys Leu His Gln Pro Ile Ile Thr Glu Tyr Gly Val
                500               505               510

Asp Thr Leu Ala Gly Leu His Ser Met Tyr Thr Asp Met Trp Ser Glu
            515               520               525

Glu Tyr Gln Cys Ala Trp Leu Asp Met Tyr His Arg Val Phe Asp Arg
            530               535               540

Val Ser Ala Val Val Gly Glu Gln Val Trp Asn Phe Ala Asp Phe Ala
545               550               555               560

Thr Ser Gln Gly Ile Leu Arg Val Gly Gly Asn Lys Lys Gly Ile Phe
                565               570               575

Thr Arg Asp Arg Lys Pro Lys Ser Ala Ala Phe Leu Leu Gln Lys Arg
            580               585               590

Trp Thr Gly Met Asn Phe Gly Lys Pro Gln Gly Gly Lys Gln
            595               600               605

Ala Ser His His His His His His Val
    610               615

<210> SEQ ID NO 35
<211> LENGTH: 34
<212> TYPE: PRT
<213> ORGANISM: Artificial sequence
<220> FEATURE:
<223> OTHER INFORMATION: Salmon calcitonin BAC57417

<400> SEQUENCE: 35

Lys Cys Ser Asn Leu Ser Thr Cys Val Leu Gly Lys Leu Ser Gln Glu
1               5                   10                  15

Leu His Lys Leu Gln Thr Tyr Pro Arg Thr Asn Thr Gly Ser Gly Thr
                20                  25                  30

Pro Gly

<210> SEQ ID NO 36
<211> LENGTH: 102
<212> TYPE: DNA
<213> ORGANISM: Artificial sequence
<220> FEATURE:
<223> OTHER INFORMATION: Salmon calcitonin BAC57417 DNA

<400> SEQUENCE: 36
aagtgctcca acctctctac ctgcgttctt ggtaagctct ctcaggagct tcacaagctc      60
```

```
cagacttacc ctagaaccaa cactggttcc ggtaccc ctg gt                    102
```

<210> SEQ ID NO 37
<211> LENGTH: 53
<212> TYPE: PRT
<213> ORGANISM: Artificial sequence
<220> FEATURE:
<223> OTHER INFORMATION: hEGF based on AAF85790

<400> SEQUENCE: 37

```
Asn Ser Asp Ser Glu Cys Pro Leu Ser His Asp Gly Tyr Cys Leu His
 1               5                  10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50
```

<210> SEQ ID NO 38
<211> LENGTH: 162
<212> TYPE: DNA
<213> ORGANISM: Artificial sequence
<220> FEATURE:
<223> OTHER INFORMATION: hEGF based on AAF85790 DNA

<400> SEQUENCE: 38

```
aactctgatt cagaatgccc actcagtcac gacggatatt gtcttcacga tggggtatgc    60
atgtacatcg aggccttgga caagtacgca tgtaattgtg tagtgggata cattggtgaa   120
cgctgtcagt atcgagactt gaaatggtgg gagcttaggt ga                     162
```

<210> SEQ ID NO 39
<211> LENGTH: 191
<212> TYPE: PRT
<213> ORGANISM: Artificial sequence
<220> FEATURE:
<223> OTHER INFORMATION: hGH based on P01241

<400> SEQUENCE: 39

```
Phe Pro Thr Ile Pro Leu Ser Arg Leu Phe Asp Asn Ala Met Leu Arg
 1               5                  10                  15

Ala His Arg Leu His Gln Leu Ala Phe Asp Thr Tyr Gln Glu Phe Glu
            20                  25                  30

Glu Ala Tyr Ile Pro Lys Glu Gln Lys Tyr Ser Phe Leu Gln Asn Pro
        35                  40                  45

Gln Thr Ser Leu Cys Phe Ser Glu Ser Ile Pro Thr Pro Ser Asn Arg
    50                  55                  60

Glu Glu Thr Gln Gln Lys Ser Asn Leu Glu Leu Leu Arg Ile Ser Leu
65                  70                  75                  80

Leu Leu Ile Gln Ser Trp Leu Glu Pro Val Gln Phe Leu Arg Ser Val
                85                  90                  95

Phe Ala Asn Ser Leu Val Tyr Gly Ala Ser Asp Ser Asn Val Tyr Asp
            100                 105                 110

Leu Leu Lys Asp Leu Glu Glu Gly Ile Gln Thr Leu Met Gly Arg Leu
        115                 120                 125

Glu Asp Gly Ser Pro Arg Thr Gly Gln Ile Phe Lys Gln Thr Tyr Ser
    130                 135                 140

Lys Phe Asp Thr Asn Ser His Asn Asp Asp Ala Leu Leu Lys Asn Tyr
145                 150                 155                 160
```

Gly Leu Leu Tyr Cys Phe Arg Lys Asp Met Asp Lys Val Glu Thr Phe
            165                 170                 175

Leu Arg Ile Val Gln Cys Arg Ser Val Glu Gly Ser Cys Gly Phe
        180                 185                 190

<210> SEQ ID NO 40
<211> LENGTH: 576
<212> TYPE: DNA
<213> ORGANISM: Artificial sequence
<220> FEATURE:
<223> OTHER INFORMATION: hGH based on P01241

<400> SEQUENCE: 40
ttcccaacca ttcccttatc caggcttttt gacaacgcta tgctccgcgc ccatcgtctg    60
caccagctgg cctttgacac ctaccaggag tttgaagaag cctatatccc aaaggaacag   120
aagtattcat tcctgcagaa cccccagacc tccctctgtt tctcagagtc tattccgaca   180
ccctccaaca gggaggaaac acaacagaaa tccaacctag agctgctccg catctccctg   240
ctgctcatcc agtcgtggct ggagcccgtg cagttcctca ggagtgtctt cgccaacagc   300
ctggtgtacg gcgcctctga cagcaacgtc tatgacctcc taaggacct agaggaaggc   360 atccaaacgc tgatggggag gctggaagat ggcagccccc ggactgggca gatcttcaag   420
cagacctaca gcaagttcga cacaaactca cacaacgatg acgcactact caagaactac   480
gggctgctct actgcttcag gaaggacatg gacaaggtcg agacattcct gcgcatcgtg   540
cagtgccgct ctgtggaggg cagctgtggc ttctga                             576

<210> SEQ ID NO 41
<211> LENGTH: 53
<212> TYPE: PRT
<213> ORGANISM: Artificial sequence
<220> FEATURE:
<223> OTHER INFORMATION: hEGF protein

<400> SEQUENCE: 41

Asn Ser Asp Ser Glu Cys Pro Leu Ser His Asp Gly Tyr Cys Leu His
1               5                   10                  15

Asp Gly Val Cys Met Tyr Ile Glu Ala Leu Asp Lys Tyr Ala Cys Asn
            20                  25                  30

Cys Val Val Gly Tyr Ile Gly Glu Arg Cys Gln Tyr Arg Asp Leu Lys
        35                  40                  45

Trp Trp Glu Leu Arg
    50

<210> SEQ ID NO 42
<211> LENGTH: 162
<212> TYPE: DNA
<213> ORGANISM: Artificial sequence
<220> FEATURE:
<223> OTHER INFORMATION: hEGF DNA

<400> SEQUENCE: 42
aactctgatt cagaatgccc actcagtcac gacggatatt gtcttcacga tggggtatgc    60
atgtacatcg aggccttgga caagtacgca tgtaattgtg tagtgggata cattggtgaa   120
cgctgtcagt atcgagactt gaaatggtgg gagcttaggt ga                      162

<210> SEQ ID NO 43
<211> LENGTH: 33
<212> TYPE: DNA
<213> ORGANISM: Artificial sequence
<220> FEATURE:

```
<223> OTHER INFORMATION: 22aZ5'DNA

<400> SEQUENCE: 43
gaggatccgc atggctacca agatattagc cct                                  33

<210> SEQ ID NO 44
<211> LENGTH: 48
<212> TYPE: DNA
<213> ORGANISM: Artificial sequence
<220> FEATURE:
<223> OTHER INFORMATION: 22aZ3' DNA

<400> SEQUENCE: 44
cattcatgat tccgccacct ccaccaaaga tggcacctcc aacgatgg                  48

<210> SEQ ID NO 45
<211> LENGTH: 42
<212> TYPE: DNA
<213> ORGANISM: Artificial sequence
<220> FEATURE:
<223> OTHER INFORMATION: Rice13ProI-5'

<400> SEQUENCE: 45
gagtcgacgg atccatgaag atcattttcg tctttgctct cc                        42

<210> SEQ ID NO 46
<211> LENGTH: 51
<212> TYPE: DNA
<213> ORGANISM: Artificial sequence
<220> FEATURE:
<223> OTHER INFORMATION: Rice13ProI-3'

<400> SEQUENCE: 46
catccatggt tccgccacct ccacccaaga caccgccaag ggtggtaatg g              51

<210> SEQ ID NO 47
<211> LENGTH: 7
<212> TYPE: PRT
<213> ORGANISM: Artificial sequence
<220> FEATURE:
<223> OTHER INFORMATION: wheat prolamin storage protein

<400> SEQUENCE: 47

Pro Gln Gln Pro Phe Pro Gln
1               5

<210> SEQ ID NO 48
<211> LENGTH: 8
<212> TYPE: PRT
<213> ORGANISM: Artificial sequence
<220> FEATURE:
<223> OTHER INFORMATION: wheat prolamin storage protein

<400> SEQUENCE: 48

Pro Gln Gln Gln Pro Pro Phe Ser
1               5

<210> SEQ ID NO 49
<211> LENGTH: 5
<212> TYPE: PRT
<213> ORGANISM: Artificial sequence
<220> FEATURE:
<223> OTHER INFORMATION: wheat prolamin storage protein

<400> SEQUENCE: 49

Pro Gln Gln Pro Gln
1               5
```

<210> SEQ ID NO 50
<211> LENGTH: 34
<212> TYPE: DNA
<213> ORGANISM: Artificial sequence
<220> FEATURE:
<223> OTHER INFORMATION: Primer GFP5'

<400> SEQUENCE: 50
aattcatgag cagtaaagga gaagaacttt tcac                          34

<210> SEQ ID NO 51
<211> LENGTH: 35
<212> TYPE: DNA
<213> ORGANISM: Artificial sequence
<220> FEATURE:
<223> OTHER INFORMATION: Primer GFP3'

<400> SEQUENCE: 51
attggatcct cattatttgt atagttcatc catgc                         35

<210> SEQ ID NO 52
<211> LENGTH: 34
<212> TYPE: DNA
<213> ORGANISM: Artificial sequence
<220> FEATURE:
<223> OTHER INFORMATION: Primer RTB5

<400> SEQUENCE: 52
aattcatgag cagtaaagga gaagaacttt tcac                          34

<210> SEQ ID NO 53
<211> LENGTH: 26
<212> TYPE: DNA
<213> ORGANISM: Artificial sequence
<220> FEATURE:
<223> OTHER INFORMATION: Primer RTB3

<400> SEQUENCE: 53
ttaccattat tttgataccc gggaag                                   26

<210> SEQ ID NO 54
<211> LENGTH: 39
<212> TYPE: DNA
<213> ORGANISM: Artificial sequence
<220> FEATURE:
<223> OTHER INFORMATION: Primer SPfor

<400> SEQUENCE: 54
cagtcgacac catgagggtg ttgctcgttg ccctcgctc                     39

<210> SEQ ID NO 55
<211> LENGTH: 30
<212> TYPE: DNA
<213> ORGANISM: Artificial sequence
<220> FEATURE:
<223> OTHER INFORMATION: Pimer RX3ECFP3'

<400> SEQUENCE: 55
ggtggatccc tagaatccat ggtctggcac                               30

<210> SEQ ID NO 56
<211> LENGTH: 44
<212> TYPE: DNA
<213> ORGANISM: Artificial sequence
<220> FEATURE:
<223> OTHER INFORMATION: Primer RX3G5ECFP3'

<400> SEQUENCE: 56
ggtggatccc tagagccacc gccacctcca tccatggtct ggca    44

<210> SEQ ID NO 57
<211> LENGTH: 1580
<212> TYPE: DNA
<213> ORGANISM: Artificial sequence
<220> FEATURE:
<223> OTHER INFORMATION: HindII/XbaI DNA fragment

<400> SEQUENCE: 57
aagcttcgaa ttctgcagtc gacaacatgg ctaccaagat attagccctc cttgcgcttc    60
ttgcccttt tgtgagcgca acaaatgcgt tcattattcc acaatgctca cttgctccta    120
gtgccattat accacagttc ctcccaccag ttacttcaat gggcttcgaa cacctagctg    180
tgcaagccta caggctacaa caagcgcttg cggcaagcgt cttacaacaa ccaattaacc    240
aattgcaaca acaatccttg gcatctaa ccatacaaac catcgcaacg caacagcaac    300
aacagttcct accagcactg agccaactag atgtggtgaa ccctgtcgcc tacttgcaac    360
agcagctgct tgcatccaac ccacttgctc tggcaaacgt agctgcatac caacaacaac    420
aacaattgca gcagtttctg ccagcgctca gtcaactagc catggtgaac cctgccgcct    480
acctacaaca gcaacaactg ctttcatcta gccctctcgc tgtgggtaat gcacctacat    540
acctgcaaca acaattgctg caacagattg taccagctct gactcagcta gctgtggcaa    600
accctgctgc ctacttgcaa cagctgcttc cattcaacca actgactgtg tcgaactctg    660
ctgcgtacct acaacagcga caacagttac ttaatccact agaagtgcca aacccattgg    720
tcgctgcctt cctacagcag caacaattgc taccatacag ccagttctct ttgatgaacc    780
ctgccttgtc gtggcagcaa cccatcgttg gaggtgccat ctttggtgga ggtggcggaa    840
tcatggtgag caagggcgag gagctgttca ccggggtggt gcccatcctg gtcgagctgg    900
acggcgacgt aaacggccac aagttcagcg tgtccggcga gggcgagggc gatgccacct    960
acggcaagct gaccctgaag ttcatctgca ccaccggcaa gctgcccgtg ccctggccca    1020
ccctcgtgac caccctgacc tggggcgtgc agtgcttcag ccgctacccc gaccacatga    1080
agcagcacga cttcttcaag tccgccatgc ccgaaggcta cgtccaggag cgcaccatct    1140
tcttcaagga cgacggcaac tacaagaccc gcgccgaggt gaagttcgag ggcgacaccc    1200
tggtgaaccg catcgagctg aagggcatcg acttcaagga ggacggcaac atcctggggc    1260
acaagctgga gtacaactac atcagccaca acgtctatat caccgccgac aagcagaaga    1320
acggcatcaa ggccaacttc aagatccgcc acaacatcga ggacggcagc gtgcagctcg    1380
ccgaccacta ccagcagaac accccatcg gcgacggccc cgtgctgctg cccgacaacc    1440
actacctgag cacccagtcc gccctgagca agaccccaa cgagaagcgc gatcacatgg    1500
tcctgctgga gttcgtgacc gccgccggga tcactctcgg catggacgag ctgtacaagt    1560
aaagcggccg cgactctaga    1580

<210> SEQ ID NO 58
<211> LENGTH: 29
<212> TYPE: DNA
<213> ORGANISM: Artificial sequence
<220> FEATURE:
<223> OTHER INFORMATION: ECFP NcoI oligonucleotide

<400> SEQUENCE: 58
gtaccatggt gagcaagggc gaggagctg    29

<210> SEQ ID NO 59
<211> LENGTH: 48
<212> TYPE: DNA
<213> ORGANISM: Artificial sequence
<220> FEATURE:
<223> OTHER INFORMATION: ECFPN1 BamNotSac oligonucleotide

<400> SEQUENCE: 59
gcagagctcg cggccgcgga tccttacttg tacagctcgt ccatgccg    48

<210> SEQ ID NO 60
<211> LENGTH: 24
<212> TYPE: DNA
<213> ORGANISM: Artificial sequence
<220> FEATURE:
<223> OTHER INFORMATION: mCherry RcaI 5' template

<400> SEQUENCE: 60
atcatgatgg tgagcaaggg cgag    24

<210> SEQ ID NO 61
<211> LENGTH: 27
<212> TYPE: DNA
<213> ORGANISM: Artificial sequence
<220> FEATURE:
<223> OTHER INFORMATION: RX3STOP3' fragment

<400> SEQUENCE: 61
tcggatcctt ctagaatcat caggtct    27

<210> SEQ ID NO 62
<211> LENGTH: 30
<212> TYPE: DNA
<213> ORGANISM: Artificial sequence
<220> FEATURE:
<223> OTHER INFORMATION: primer 5'DNAb

<400> SEQUENCE: 62
agccatggcg cgagtccgga gctatctctg    30

<210> SEQ ID NO 63
<211> LENGTH: 23
<212> TYPE: DNA
<213> ORGANISM: Artificial sequence
<220> FEATURE:
<223> OTHER INFORMATION: primer 3' DNAb

<400> SEQUENCE: 63
gttgtgtaca atgatgtcat tcg    23

<210> SEQ ID NO 64
<211> LENGTH: 43
<212> TYPE: DNA
<213> ORGANISM: Artificial sequence
<220> FEATURE:
<223> OTHER INFORMATION: DNAbhGH

<400> SEQUENCE: 64
gaatgacatc attgtacaca acttcccaac cattcccctta tcc    43

<210> SEQ ID NO 65
<211> LENGTH: 40
<212> TYPE: DNA
<213> ORGANISM: Artificial sequence
<220> FEATURE:
<223> OTHER INFORMATION: 3'hGH primer

```
<400> SEQUENCE: 65
atggtaccac gcgtcttatc agaagccaca gctgccctcc                            40

<210> SEQ ID NO 66
<211> LENGTH: 36
<212> TYPE: DNA
<213> ORGANISM: Artificial sequence
<220> FEATURE:
<223> OTHER INFORMATION: primer IM-for

<400> SEQUENCE: 66
atcattgtac acgccttccc aaccattccc ttatcc                                36

<210> SEQ ID NO 67
<211> LENGTH: 35
<212> TYPE: DNA
<213> ORGANISM: Artificial sequence
<220> FEATURE:
<223> OTHER INFORMATION: primer IM-rev

<400> SEQUENCE: 67
tcaggatcct tatcagaagc cacagctgcc ctcca                                 35

<210> SEQ ID NO 68
<211> LENGTH: 45
<212> TYPE: DNA
<213> ORGANISM: Artificial sequence
<220> FEATURE:
<223> OTHER INFORMATION: Casp forward fragment

<400> SEQUENCE: 68
gactcatgat cgatgaggtg gacatggaga acactgaaaa ctcag                      45

<210> SEQ ID NO 69
<211> LENGTH: 49
<212> TYPE: DNA
<213> ORGANISM: Artificial sequence
<220> FEATURE:
<223> OTHER INFORMATION: Casp3 reverse fragment

<400> SEQUENCE: 69
ctgggtacca tgtctagatc attagtgata aaaatagagt tcttttgtg                  49

<210> SEQ ID NO 70
<211> LENGTH: 43
<212> TYPE: DNA
<213> ORGANISM: Artificial sequence
<220> FEATURE:
<223> OTHER INFORMATION: Casp2 for fragment

<400> SEQUENCE: 70
gactcatgat cgatgagcac gacggtcctc tctgccttca ggt                        43

<210> SEQ ID NO 71
<211> LENGTH: 43
<212> TYPE: DNA
<213> ORGANISM: Artificial sequence
<220> FEATURE:
<223> OTHER INFORMATION: Casp2 reverse fragment

<400> SEQUENCE: 71
ctgggtacca tgtctagata atcatgtggg agggtgtcct ggg                        43

<210> SEQ ID NO 72
<211> LENGTH: 1148
```

```
<212> TYPE: DNA
<213> ORGANISM: Artificial sequence
<220> FEATURE:
<223> OTHER INFORMATION: DNA fragment

<400> SEQUENCE: 72
gctagcgttt aaacgggccc tctagactcg acaccatgag ggtgttgctc gttgccctcg     60
ctctcctggc tctcgctgcg agcgccacct ccacgcatac aagcggcggc tgcggctgcc    120
agccaccgcc gccggttcat ctaccgccgc cggtgcatct gccacctccg gttcacctgc    180
cacctccggt gcatctccca ccgccggtcc acctgccgcc gccggtccac ctgccaccgc    240
cggtccatgt gccgccgccg gttcatctgc cgccgccacc atgccactac cctactcaac    300
cgccccggcc tcagcctcat ccccagccac acccatgccc gtgccaacag ccgcatccaa    360
gcccgtgcca aggcgcgcc ggtggaggcg gaggtaccat gattgagggt aggattgttg     420
gtggaagtga ttcccgtgaa ggtgcttggc cttgggttgt ggctctttat ttcgatgatc    480
agcaagtttg tggagcctcc cttgtttcta gagattggct tgtgtctgct gcacattgcg    540
tgtatggaag aaatatggaa ccaagtaagt ggaaggcagt tcttggattg catatggctt    600
caaatcttac aagtccacag attgaaactc gtctcatcga tcaaattgtt atcaacccac    660
actataacaa gaggagaaaa aacaatgata ttgctatgat gcatcttgag atgaaagtga    720
actacacaga ttacattcag ccaatttgtc ttccagagga aaaccaagtt ttcccacctg    780
gaaggatttg ttctattgcc ggttggggag cacttatcta tcaaggatca actgcagatg    840
ttcttcaaga agcagatgtt ccacttttgt caaatgagaa atgccaacag caaatgcctg    900
agtataacat tactgagaat atggtgtgtg ctggatacga ggcaggaggt gtggattctt    960
gtcagggaga ttctggaggt cctcttatgt gccaggagaa taacagatgg cttttagccg   1020
gagttacttc tttcggatac caatgcgcat tgccaaatag acctggtgtg tatgctagag   1080
ttccaaggtt tacagagtgg attcaatcat ttctacattg ataaggatcc gagctcggta   1140
ccaagctt                                                            1148

<210> SEQ ID NO 73
<211> LENGTH: 18
<212> TYPE: DNA
<213> ORGANISM: Artificial sequence
<220> FEATURE:
<223> OTHER INFORMATION: bGH rev primer

<400> SEQUENCE: 73
cctcgactgt gccttcta                                                    18

<210> SEQ ID NO 74
<211> LENGTH: 37
<212> TYPE: DNA
<213> ORGANISM: Artificial sequence
<220> FEATURE:
<223> OTHER INFORMATION: bGH rev2 primer

<400> SEQUENCE: 74
cctctagact cgacccatgg tgagcaaggg cgaggag                               37
```

PRODUCTION OF BIOLOGICALLY ACTIVE PROTEINS

CROSS-REFERENCE TO RELATED APPLICATION

This application claims benefit of provisional application Ser. No. 60/776,391 that was filed on Feb. 23, 2006.

TECHNICAL FIELD

The present invention contemplates the production of biologically active recombinant peptides and proteins, collectively referred to as polypeptides, in eukaryotic cells and organisms as host systems. More particularly, a biologically active polypeptide is fused to a protein body-inducing sequence (PBIS) that mediates the induction of recombinant protein body-like assemblies (RPBLA) to form a fusion protein that is stably expressed and accumulated in the host system as an RPBLA after transformation of the host cells with an appropriate vector.

BACKGROUND ART

The production of recombinant proteins for therapeutic, nutraceutical or industrial uses has enjoyed great success over the past several decades. Introduction of heterologous genes having desired nucleotide sequences into a variety of expression hosts is now routine. This process nearly always leads to expression of polypeptides or proteins having the correct predicted primary amino acid residue sequence (primary structure) encoded by the introduced nucleotides. In many instances, however, the protein or polypeptide that is ultimately produced can possess the correct primary amino acid residue sequence of the naturally-produced molecule, but lack the biological activity expected of that material.

Biological activity, given the proper primary structure of the expressed product, can be a function of the protein's secondary, tertiary or quaternary structure. These structural features include having the proper folding and internal hydrogen, Van der Waals, ionic and disulfide bonding patterns, appropriate intermolecular and intramolecular subunit interactions, and also having the proper post-translational modifications, as for instance glycosylation. For example, disulfide bond formation occurs spontaneously in the lumen of the endoplasmic reticulum (ER) of eukaryotic cells, but not in the reducing environment of the cytosol of prokaryotes, which makes bacterial cells such as *Escherichia coli* poor hosts for the synthesis of correctly-folded mammalian proteins that are normally stabilized by disulfide bonds. Disulfide bond formation can occur in the periplasmic space of *E. coli* where certain prokaryotic chaperoning, foldases and PDI-like proteins are functional (Fernandez, et al., 2001. *Mol. Microbiol.* April 40(2):332-346). However, even in this compartment the bacterial oxi-redox system is not very efficient for eukaryotic proteins.

A particular case in point relates to erythropoietin (EPO), a protein that stimulates red blood cell production. Recombinant EPO is disclosed in Lin, U.S. Pat. No. 4,703,008, which describes activities for heterologous human EPO protein expressed from *E. coli, S. cerevisiae*, and mammalian Chinese hamster ovary (CHO) and African green monkey kidney (COS-1) cells. Although EPO expressed by each cell type had the correct primary amino acid sequence and was cross-reactive with anti-EPO antisera, only the proteins expressed from mammalian cells exhibited the expected levels of biological activity as determined by in vitro and in vivo assays. These observed differences in biological activity were determined to be a function of improper glycosylation in the prokaryotic and lower eukaryotic host cells. *E. coli*, a prokaryote, does not perform the eukaryotic enzymatic steps of N-linked glycosylation. Yeast cells are eukaryotes and capable of N-linked glycosylation, but their glycosylation enzymes differ from that of animals and plants and consequently result in a different pattern of terminal glycosylation for secreted proteins. On the other hand, the CHO and COS-1 cells used to provide proteins of substantially correct biological activity were mammalian, and the proteins expressed therefrom were consequently useful. Published studies of glycosylated and aglycosylated EPO indicate that glycosylation plays a critical role in stabilizing erythropoietin under denaturing conditions (Narhi et al., (1991) *J. Biol. Chem.* 266(34):23022-23026). In addition, it has been reported that in vivo life time and activity of EPO can be related to the glycosylation state of the molecule, and correct interaction with the erythrogenic EPO receptor is also affected by EPO glycosylation pattern.

Eukaryotic cells are therefore greatly preferred for recombinant production of therapeutic, industrial and other useful proteins of eukaryotic origin. Consequently, many different types of eukaryotic cells and organisms have been shown to be capable of producing biologically active recombinant proteins. Unfortunately, many such eukaryotic expression systems are inefficient with respect to protein product yield and cost of manufacture, even when proteins are secreted extracellularly. The high costs frequently derived from low recombinant protein production levels and/or from complicated downstream protein isolation and purification procedures can invalidate a protein's commercial application. Active research is thus being done to improve both production levels and purification procedures.

One way of improving the efficiency of recombinant protein isolation is by means of intracellular concentration. One of these approaches is the random aggregation of recombinant proteins into non-secreted inclusion bodies which can be separated from lysed cells by density-based purification techniques. Insoluble inclusion bodies are amorphous protein deposits found in bacteria expressing complex recombinant proteins (such as those of eukaryotic origin). The absence of specialized eukaryotic molecular chaperones in prokaryotic cells results in random folding of eukaryotic proteins. Structural characterization studies have shown that the insoluble nature of inclusion bodies may be due to the random hydrophobic intermolecular interactions of proteins which are not correctly folded (Seshadri et al., 1999, *Methods Enzymol.* 309:559-576). The general strategy used to recover active proteins from inclusion bodies subsequent to their separation from cell material requires the complete solubilization of the recombinant protein to disrupt the random aggregates followed by one or more chemical refolding steps. This is an important issue because the efficiency of protein renaturation is highly limiting, particularly if the protein contains disulfide bonds (Clarc, Ed., April 2001 *Curr. Opin. Biotechnol.* 12(2): 202-207).

More particularly, high concentrations of strong denaturants and chaotropic agents (e.g. detergents, urea and guanidinium hydrochloride) are required for solubilization of the aggregated and unfolded proteins in inclusion bodies. These agents must be dialyzed away completely in order to later refold the proteins into their correct and biologically active conformations. As a consequence the yield of correctly refolded recombinant proteins from inclusion bodies is extremely low, and moreover the biological activities of such refolded proteins are typically much less than that of the native-formed proteins.

Protein bodies (PBs) are naturally-occurring structures in certain plant seeds that have evolved to concentrate storage proteins intracellularly in eukaryotic cells while retaining correct folding and biological activity. PBs share some of the characteristics of the inclusion bodies from bacteria. They are dense, and contain a high quantity of proteins that are tightly packed by hydrophobic interactions [Momany et al., 2006 *J. Agric. Food Chem*. January 25; 54(2):543-547 and Garrat, et al., 1993 *Proteins* January; 15(1):88-99]. However, in contrast to the randomly-aggregated proteins in bacterial inclusion bodies, the proteins in PBs are thought to be aggregated in a non-random (assembled) manner.

A new technology for creation of synthetic PBs based on the fusion of a plant seed storage protein domain with a heterologous protein of interest (WO 2004/003207) has been developed to increase the stability and accumulation of recombinant proteins in higher plants. These storage proteins are specific to plant seeds wherein they accumulate stably in natural PBs (Galili et al., 1993, *Trends Cell Biol* 3:437-442) following insertion into the lumen of the ER via a signal peptide and assembly into ER-derived protein bodies (ER-PBs) (Okita et al., 1996 *Annu. Rev. Plant Physiol Mol. Biol.* 47:327-350; Herman et al., 1999 *Plant Cell* 11:601-613; Sanderfoot et al., 1999 *Plant Cell* 11:629-642). Full-length recombinant storage proteins have also been observed to assemble into PB-like organelles in non-plant host systems as *Xenopus* oocytes following injection of the corresponding mRNAs. This system has been used as a model to study the targeting properties of these storage proteins (Simon et al., 1990, *Plant Cell* 2:941-950; Altschuler et al., 1993, *Plant Cell* 5:443-450; Torrent et al., 1994, *Planta* 192:512-518) and to test the possibility of modifying the 19 kDa α-zein, a maize prolamin, by introducing the essential amino acids lysine and tryptophan into its sequence, without altering its stability (Wallace et al, 1988, *Science* 240:662-664).

Zeins, the complex group of maize prolamins, have also been produced recombinantly in yeast. Coraggio et al. (1988, *Eur J Cell Biol* 47:165-172), expressed native and modified α-zeins in yeast to study targeting determinants of this protein. Kim et al., 2002, *Plant Cell* 14: 655-672, studied the possible α-, β-, γ- and δ-zein interactions that could lead to protein body formation. To address this question, they transformed yeast cells with cDNAs encoding these proteins. In addition, those authors constructed zein-GFP fusion proteins to determine the subcellular localization of zein proteins in yeast cells but did not observe formation of dense, concentrated structures characteristic of bona fide PBs. It is worth to noting that Kim et al. (2002, *Plant Cell* 14: 655-672) concluded that yeast is a poor model for the study of zein interactions because zeins accumulated very poorly in transformed yeast. Yeast has also been used as a model to study the mechanisms that control the transport and deposition of gliadin storage proteins in wheat (Rosenberg et al., 1993, *Plant Physiol* 102:61-69).

These results in yeast as well as the similarities between bacterial inclusion bodies and PBs suggested that proteins accumulated in synthetic PBs would not be active unless renaturation steps were performed. Moreover, the presence of disulfide bonds in some natural PB-assembling protein domains, as for instance RX3, [Ludevid et al., 1984 *Plant Mol. Biol.* 3:227-234 and Kawagoe et al., 2005 *Plant Cell* April 17(4):1141-1153], which are probably involved in PB formation and stabilization, could represent an additional difficulty for production of a biologically active, native-folded protein in PBs. This would be particularly relevant for a recombinant protein that contains its own cysteine residues that might interact inappropriately with cysteines in the PB-assembling domain. The observation of biological activity without the need for refolding and renaturation of a wide variety of proteins produced in synthetic PBs in non-yeast eukaryotic hosts was therefore unexpected.

Biological activity is particularly relevant for vaccines, which must induce a correct immune response in an immunized human or other animal. Several new vaccines are composed of synthetic, recombinant, or highly purified subunit immunogens (antigens) that are thought to be safer than whole-inactivated or live-attenuated vaccines. However, the absence of immunomodulatory components having adjuvant properties associated with attenuated or killed vaccines often results in weaker immunogenicity for such vaccines.

Immunologic adjuvants are agents that enhance specific immune responses. An immunologic adjuvant can be defined as any substance or formulation that, when incorporated into a vaccine, acts generally to accelerate, prolong, or enhance the quality of specific immune responses to vaccine antigens. The word adjuvant is derived from the Latin verb adjuvare, which means to help or aid. Adjuvant mechanisms of action include the following: (1) increasing the biological or immunologic half-life of vaccine immunogens; (2) improving antigen delivery to antigen-presenting cells (APCs), as well as antigen processing and presentation by the APCs; and (3) inducing the production of immunomodulatory cytokines.

Phagocytosis involves the entry of large particles, such as apoptotic cells or whole microbes. The capacity of the cells to engulf large particles likely appeared as a nutritional function in unicellular organisms; however complex organisms have taken advantage of the phagocytic machinery to fulfill additional functions. For instance, the phagocytosis of antigens undertaken by the macrophages, the B-cells or the dendritic cells represents a key process in innate and adaptive immunity. Indeed, phagocytosis and the subsequent killing of microbes in phagosomes form the basis of an organism's innate defense against intracellular pathogens. Furthermore, the degradation of pathogens in the phagosome lumen and the production of antigenic peptides, which are presented by phagocytic cells to activate specific lymphocytes, also link phagocytosis to adaptive immunity (Jutras et al., 2005, *Annual Review in Cell Development Biology.* 21:511-27).

The proteins present on engulfed particles encounter an array of degrading proteases in phagosomes. Yet, this destructive environment generates peptides that are capable of binding to MHC class II molecules. Newly formed antigen-MHC class II complexes are delivered to the cell surface for presentation to CD4+ T cells (Boes et al. 2002 *Nature* 418:983-988). The activation of these cells induces the Th2 subset of cytokines such as IL-4 and IL-5 that help B cells to proliferate and differentiate, and is associated with humoral-type immune response.

A large body of evidence indicates that, in addition to the clear involvement of the MHC class II pathway in the immune response against phagocytosed pathogens, antigens from pathogens, including mycobacteria, *Salmonella, Brucella*, and *Leishmania*, can elicit an antigen cross-presentation. That is to say, the presentation of engulfed antigen by phagocytosis by the MHC class I-dependent response promotes the proliferation of CD8+ cytotoxic T cells (Ackerman et al., 2004 *Nature Immunology* 5(7):678-684; Kaufmann et al., 2005 *Current Opinions in Immunology* 17(1):79-87).

Dendritic cells play a central antigen presentation role to induce the immune system (Blander et al., *Nature Immunology* 2006 10:1029-1035). Although rare, dendritic cells are the most highly specialized APC, with the ability both to instigate and regulate immune reactivity (Lau et al. 2003 *Gut* 52:307-314). Although dendritic cells are important in presenting antigens, particularly to initiate primary immune responses, macrophages are the APC type most prominent in inflammatory sites and are specialized for clearing necrotic and apoptotic material. Macrophages can act not only as APCs, but can also perform either pro- or anti-inflammatory roles, dependent on the means by which they are activated.

Considering that APCs play a central role in the induction and regulation of the adaptive immunity (humoral and cellular), the recognition and phagocytosis of an antigen by those cells can be considered a key step in the immunization process. A wide variety of techniques based on the uptake of fluorescent particles have been developed to study phagocytosis by the macrophages (Vergne et al., 1998 *Analytical Biochemistry* 255:127-132).

An important aspect in veterinary vaccines is the genetic diversity of the species being considered and the requirement for generic systems that work across different species. To a large degree, this diversity limits the use of molecular targeting techniques to cell surface markers and immune modulators such as cytokines, because for many species including wildlife, only minimal knowledge of these molecules is available. Thus, adjuvants that rely on universal activation signals of the innate immune response (i.e. that are identical in different species) are to be preferred. Taking these requirements into consideration, particulate vaccine delivery systems are well suited for veterinary and wildlife vaccine strategies (Scheerlinck et al., 2004 *Methods* 40:118-124).

As is discussed in greater detail hereinafter, the present invention discloses that the expression of a fusion protein comprised of (i) a protein sequence that mediates induction of recombinant protein body-like assemblies (RPBLAs) linked to (ii) a biologically active polypeptide (protein of interest or target) induces the accumulation of those RPBLAs in cells of eukaryotic organisms such as plants, fungi, algae and animals, producing a biologically active target (protein).

BRIEF SUMMARY OF THE INVENTION

The present invention provides a system and method for producing a fusion protein containing a protein body-inducing sequence (PBIS) and a biologically active peptide or protein of interest (often collectively referred to herein as a polypeptide or target) in eukaryotic cells. The fusion proteins containing the polypeptide of interest stably accumulate as recombinant protein body-like assemblies (RPBLAs) in the eukaryotic cells, which can be plant, animal, fungal or algal cells.

Cells of higher plants are preferred eukaryotic host cells in some embodiments, whereas cells of lower plants such as algae are preferred in other embodiments, cells of animals such as mammals and insects are preferred eukaryotic host cells in further embodiments and fungi are preferred eukaryotic host cells in still other embodiments. The fusion protein can be expressed constitutively or preferentially in particular cells in multi-cellular eukaryotes. The PBISs are able to mediate the induction of RPBLA formation and fusion protein entry and/or accumulation in these organelles, with appropriate folding and/or post-translational modifications such as basal glycosylation and disulfide bond formation to provide biological activity to the expressed peptide or protein of interest (targets).

Thus, a eukaryotic host cell that contains a biologically active recombinant fusion protein within recombinant protein body-like assemblies (RPBLAs) is contemplated as one aspect of the present invention. The fusion protein contains two sequences linked together in which one sequence is a protein body-inducing sequence (PBIS) and the other is the sequence of at least 20 amino acid residues of a biologically active polypeptide of interest. The biologically active polypeptide, as found in nature, can be heterologous to the recited eukaryotic host cells and is thus expressed in a second cell type that is different from the first-mentioned eukaryotic host cell, or it is produced synthetically. In addition, the eukaryotic host cell does not produce PBs in the absence of the fusion protein. Thus, it is the expression of the fusion protein and the PBIS portion of that fusion protein that causes the host cell to form protein body-like assemblies or RPBLAs.

In a particular embodiment, the nucleic acid sequence used for transformation comprises (i) a nucleic acid sequence coding for a PBIS, and (ii) a nucleic acid sequence comprising the nucleotide sequence coding for a product of interest. In one embodiment, the 3' end of nucleic acid sequence (i) is linked to the 5' end of said nucleic acid sequence (ii). In another embodiment, the 5' end of nucleic acid sequence (i) is linked to the 3' end of nucleic acid sequence (ii). Thus, the PBIS sequence can be at the N-terminus or the C-terminus of the fusion protein. It is to be understood that all of the DNA linkages discussed herein for the expression of a fusion protein are such that the two components of the fusion protein are expressed in frame.

The biologically active polypeptide of the fusion protein exhibits at least 25 percent, preferably at least 50 percent, more preferably 75 percent, and most preferably at least 90 percent of the biological activity of the same polypeptide isolated from the above second cell type in an assay of the activity of that polypeptide.

In another particular embodiment, the nucleic acid sequence used for transformation comprises, in addition to the before-mentioned nucleic acid sequences (i) and (ii), a nucleic acid sequence comprising the nucleotide sequence coding for a linker or spacer amino acid sequence. The spacer amino acid sequence can be an amino acid sequence cleavable, or not cleavable, by enzymatic or autoproteolytic or chemical means. In a particular embodiment, the nucleic acid sequence (iii) is placed between the nucleic acid sequences (i) and (ii), e.g., the 3' end of nucleic acid sequence (iii) is linked to the 5' end of said nucleic acid sequence (ii). In another embodiment, the 5' end of said nucleic acid sequence (iii) is linked to the 3' end of nucleic acid sequence (ii).

Also, in a particular embodiment, the nucleic acid sequence used for transformation purposes encodes a sequence in accord with patent application WO 2004003207, wherein the nucleic acid sequence coding for the amino acid sequence that is specifically cleavable by enzymatic or chemical means is present or absent. In a further embodiment, the fusion proteins can be a direct fusion between the PBIS and the peptide or protein of interest.

In a further embodiment, the method of the invention further comprises the isolation and purification of the biologically active fusion protein.

In another embodiment, the method of the invention further comprises the isolation and purification of the fusion protein, and obtaining a biologically active fusion protein. Thus, where the fusion protein is tightly assembled and enclosed within a membrane, it can be difficult to illustrate that the polypeptide is biologically active. As a consequence, the biological activity can be assayed after removal of the membrane, and if it is required, the solubilization of the fusion protein. A method of preparing a biologically active polypeptide is therefore contemplated.

In this method, recombinant protein body-like assemblies (RPBLAs) are provided that comprise a membrane-enclosed fusion protein. The RPBLAs are usually present in a generally spherical form having a diameter of about 0.5 to about 3 microns (μ), but in some instances are amorphous in shape and can vary widely in dimensions, but are still derived from the ER. The fusion protein contains two sequences linked together in which one sequence is a protein body-inducing sequence (PBIS) and the other is a biologically active polypeptide. The RPBLAs are contacted with an aqueous buffer containing a membrane-disassembling amount of a detergent (surfactant). That contact is maintained for a time period sufficient to disassemble the membrane and at a temperature that does not denature the biologically active polypeptide to separate the membrane and fusion protein. The separated fusion protein is thereafter collected in a usual manner, or can be acted upon further without collection.

In some embodiments, the separated fusion protein exhibits the biological activity of the biologically active polypeptide. In other embodiments, biological activity of the polypeptide is exhibited after the fusion protein is dissolved or dispersed in an appropriate buffer. In yet other embodiments, the fusion protein has to be cleaved into its constituent parts before biological activity of the polypeptide is exhibited. Thus, the biologically active polypeptide can be linked to the PBIS by a spacer amino acid sequence that is cleavable by enzymatic or chemical means. Then, upon cleavage, the biologically active polypeptide exhibits biological activity when cleaved from the PBIS of the fusion protein. In some embodiments, the fusion protein retains its activity even when still incorporated into the intact RPBLA.

In another embodiment, the biologically active polypeptide contains at least two N-linked glycosylation sequences.

In yet another preferred embodiment, the polypeptide of interest is fused to a natural or modified storage protein, as for instance, natural or modified prolamins or prolamin domains.

In another embodiment, the RPBLAs containing the biologically active polypeptide are used as a delivery system for the biologically active polypeptide. The benefits of this invention could be applied in drug delivery, vaccines and nutrition.

In yet another embodiment, the RPBLAs containing a polypeptide antigen can be used as a delivery system to provide adjuvanticity (increase the immune response). The administration of these RPBLAs can represent an improvement in the immunization parameters such as the speed, quantity, quality and duration of the immunization. The beneficial effect of administrating antigens in RPBLAs can be achieved because (i) the antigen is encapsulated and remains longer in the blood or in the gastrointestinal tract (slow release effect) and/or (ii) the antigen is better exposed to the immune system (RPBLAs as an antigen presentation vehicle) and/or (iii) the presence of adjuvant molecules in the RPBLAs preparations, and/or (iv) the RPBLAs are carriers able to cross membranes that themselves provide adjuvanticity, and/or others.

Thus, another aspect of the invention is a vaccine or inoculum (immunogenic composition) that comprises an immunogenic effective amount of RPBLAs that contain biologically active recombinant fusion protein dissolved or dispersed in a pharmaceutically acceptable diluent. The recombinant fusion protein contains two sequences linked together in which one sequence is a PBIS and the other is a biologically active polypeptide to which an immunological response is to be induced by said vaccine or inoculum. The pharmaceutically acceptable diluent composition typically also contains water. In another embodiment an RPBLA not incorporating an antigen but possessing active adjuvant properties is co-delivered with an isolated antigen to induce an immunological response.

In another embodiment, the PBIS can be used as a carrier to cross membranes. In a specific embodiment the PBIS is ZERA (RX3) or a fragment of it.

BRIEF DESCRIPTION OF THE DRAWINGS

In the drawings forming a portion of this disclosure,

FIG. 1, Panel A is the schematic representation of the constructs used for the CHO cells transfection studies. The construct pECFP-N1 corresponds to the control expressing the ECFP in the cytosol. The pRX3-ECFP and pRX3-Gx5-ECFP are the constructs expressing the fusion protein RX3-ECFP, in the absence or presence of a spacer formed by five glycine amino acids (Gx5), respectively. The p22aZ-ECFP is the constructs coding for the maize alpha zein (22 KDa) fused to ECFP. On the bottom, the pcDNA3.1(−) (Invitrogen) based vectors are represented along with several constructs discussed hereinafter. Panel B shows the schematic representation of binary vectors for plant transformation (upper) and the baculovirus vectors for insect infection (bottom). "RX3"=N-terminal proline-rich gamma-zein sequence; "(Gly)× 5"=spacer formed by five glycines; "ECFP"=enhanced cyan fluorescent protein gene; "$P_{CMV}$"=human cytomegalovirus promoter; "$P_{PH}$"=Polyhedrin promoter; "$P_{SV40}$"=SV40 early promoter; "CaMV35S×2"=Double cauliflower mosaic virus promoter; "$P_{cbh1}$"=major cellulase promoter; "t35S"=Cauliflower mosaic virus terminator; "TEV"=Translational enhancer of the tobacco etch virus; "SV40 ter"=SV40 terminator; "HSV ter"=herpes simplex virus thymidine kinase polyadenylation signal; "cbh1 ter"=major cellulase polyadenylation signal; "Kana/Neo"=kanamycin/neomycin resistance gene; "Amp R"=Ampicilin resistance gene; "Gentamicine"=Gentamicin resistance gene; "$SP_{cbh1}$"=major cellulase signal peptide; "Ori f1"=f1 single strand DNA origin; "Ori pUC"=plasmid replication origin; "BGH ter"=Bovine growth hormone terminator; "P BLA"=beta lactamase gene promoter; "GFP"=Green fluorescent protein; "DsRED"=*Dicosoma* red fluorescent protein; "hGH"=human growth hormone; "EGF"=human epidermal growth factor; "EK"=bovine enterokinase; "GUS"=glucuronidase; "RTB"=lectin subunit of ricin (*Ricinus comunis*); "Casp2"=Human Caspase 2; "Casp3"=Human Caspase 3; "Int"=Ssp DNAb intein (New England Biolabs); "mInt"=mutated version of Ssp DNAb intein (Asp154→Ala substitution).

FIG. 2 shows immunoblots from subcellular fractionation studies of CHO cells transfected with pRX3-ECFP, pRX3-G-ECFP and pECFP-N1 as a control (Panel A); p3.1-RX3-hGH, p3.1-RX3, p3.1-RX3-EK, p3.1-RX3-C3, p3.1-RX3-C2, p3.1-RX3-GUS and p3.1-RX3-I-hGH plasmids (Panel B). In panel B the immunoblot from subcellular fractionation studies of tobacco plants agroinfiltrated with pB-RX3-RTB are also shown. Panel C corresponds to subcellular fractionation studies of insect larvae infected with pF-RX3-DsRED and pF-DsRED as a control. Transfected cell homogenates were loaded on step sucrose gradients, and after centrifugation, the accumulation of the corresponding fusion proteins in the supernatant, interphase and pellet fractions was analyzed by immunoblot. The molecular weights and the antibody used in the immunoblot are indicated on the right. H, homogenate loaded in the density gradient; S, supernatant; $F_x$, upper interphase of the X % w/w sucrose cushion; P, pellet under 56% sucrose cushion.

FIG. 6 shows western blots that illustrate the induction of Ssp DNAb intein self-cleavage after RX3-I-hGH fusion protein solubilization from a RPBLA preparation by low speed centrifugation. Panels A and B illustrate the self-cleavage of the RX3-I-hGH (wild type Ssp DNAb intein) fusion protein, after solubilization. The RX3-Im-hGH (mutated Ssp DNAb intein) fusion protein was included as a negative control. Equivalent volumes of the samples were loaded per lane, and the western blot was performed with anti-RX3 serum (Panel A) or anti-hGH serum (Panel B). The full length fusion proteins are indicated with white arrowheads and the products of the Ssp DNAb intein self-cleavage (RX3-I in Panel A, and hGH in Panel B) are indicated with black arrowheads. Panel C illustrates the comparison of RX3-I-hGH fusion protein self-cleavage efficiency after 0.1% SDS (S1) and biphasic solubilization (S2). Equivalent volumes of the samples were loaded per lane, except T0 that was overloaded 4-fold. The incubation with anti-hGH serum shows the full length fusion protein RX3-I-hGH (white arrowhead) and the liberated hGH (black arrowhead). "S"=Soluble fraction; "U"=insoluble fraction; "T0"=Sample before induction of intein self-cleavage.

FIG. 7 shows the uptake and processing by macrophages of RX3-DsRED RPBLAs produced in insect larvae. In panel A, confocal microscopy analysis of macrophages 1 hour after incubation with insect RX3-DsRED RPBLAs is shown. On the left, 2 macrophages can be observed by phase contrast microscopy. On the right is a merged image of DsRED fluorescence (black arrowheads) and the self-fluorescence of the macrophages (white arrowheads) from 1 micrometer optical section of the same cells. The position of the nucleus (N) in this optical section indicates that the RPBLAs have been taken up and are now intracellular. Panel B shows a time course study (1 and 10 hours) of DsRED fluorescence emitted by the macrophages, after incubation for 1 hour with RPBLAs containing RX3-DsRED. On the left, phase contrast microscopy shows the presence of macrophages. On the right, the DsRED fluorescence of 1 micrometer optical sections shows the presence of undigested RPBLAs at 1 hour (white arrowhead) and a more homogeneous DsRED fluorescence pattern at 10 hours indicative of digested and dispersed RPBLAs. The inset image corresponds to a higher magnification of the undigested RPBLAs observed at 1 hour.

FIG. 8 shows the uptake of RX3-DsRED RPBLAs from insect larvae by dendritic cells. The micrographs correspond to dendritic cells incubated with RPBLAs (Panel A) and membrane-less RPBLAs (Panel B) over time (2, 5 and 10 hours). In the upper portion of each panel are phase contrast images showing the presence of dendritic cells. At the bottom, the DsRED fluorescence from the same dendritic cells shows the presence of RPBLAs absorbed to the plasma membrane (2 hours) or phagocytosed inside the cell (5 and 10 hours). "N"=nucleus.

Figure 3:
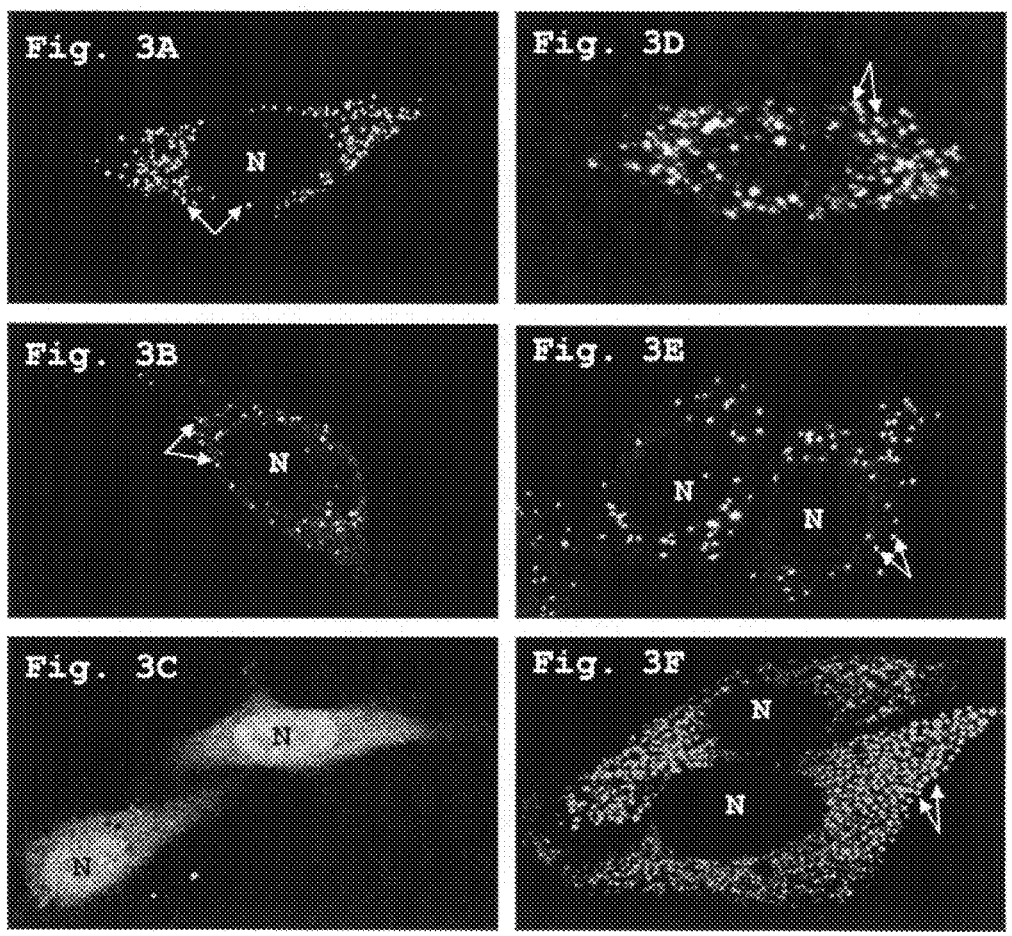
FIG. 3 is a confocal microscopy photographic montage in six panels showing the localization of the fusion proteins RX3-ECFP (panel A), RX3-Gx5-ECFP (panel B), 22aZ-ECFP (panel D), RX3-GFP (panel E) and RX3-DsRED (panel F) in RPBLAs within transfected CHO cells. Some of the RPBLA structures containing the active (fluorescent) fusion proteins are indicated by arrows. The localization of the ECFP in the cytosol and the nucleus (panel C) in CHO cells transfected by pECFP-N1 are shown as a control. "N"=nucleus.
Figure 4:
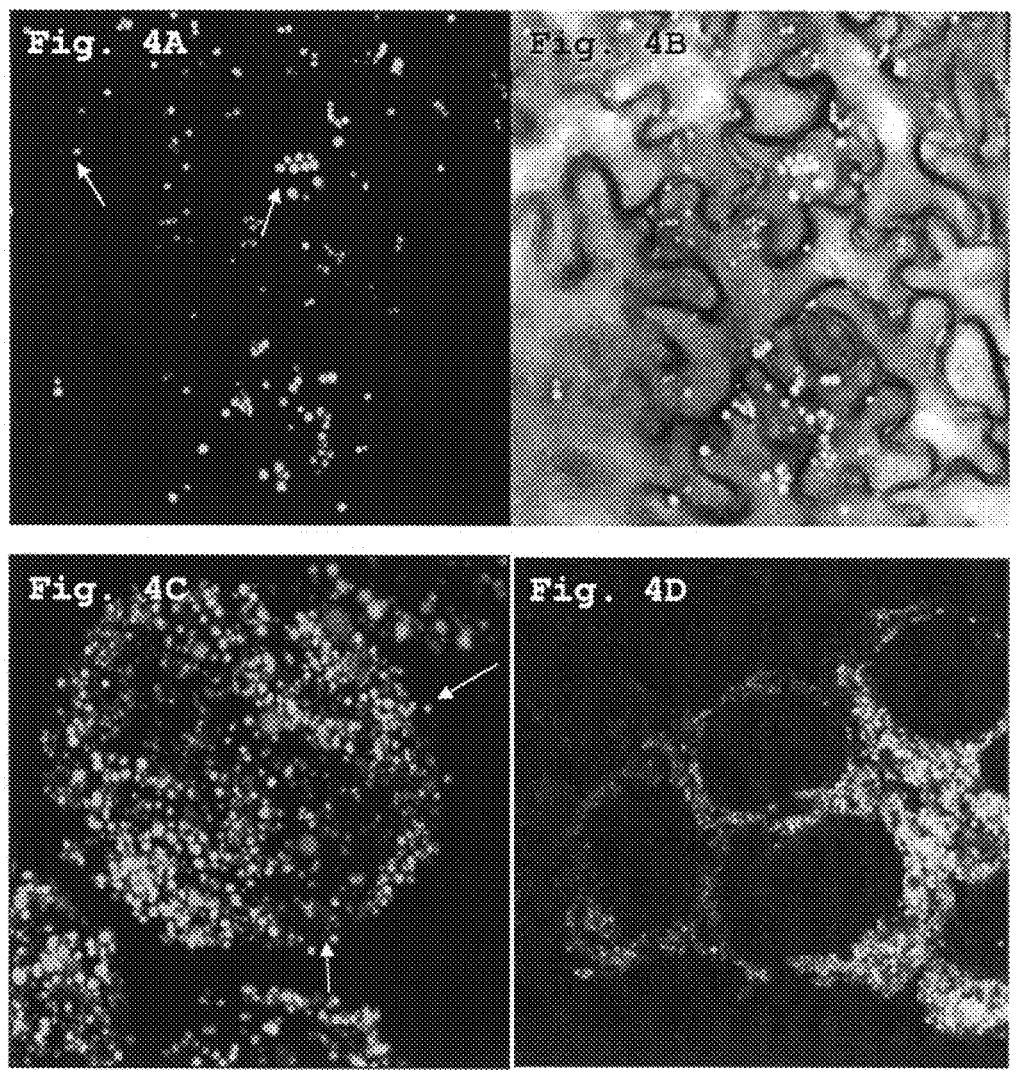
FIG. 4 is a confocal microscopy photograph in four panels showing the localization of fluorescent RX3 fusion proteins in different hosts. In panel A is shown the confocal optical sections of epidermal leaf tissue from tobacco plants co-agroinfiltrated with pB-RX3-GFP and a binary vector coding for HcPRO, a suppressor of gene silencing. It can be observed a lot fluorescent RPBLAs containing the active RX3-GFP fusion protein. On the right, in Panel B, the merging of the RX3-GFP fluorescence and the contrast phase shows the high percentage of transiently transfected cells. The projection of optical sections of SF9 insect cells infected with pF-RX3-DsRED is shown in Panel C. One micrometer optical sections of fat tissue from insect larvae infected with pF-RX3-DsRED are shown in Panel D. Some of the RPBLA structures containing the active (fluorescent) fusion proteins are indicated by arrows.

The present invention has several benefits and advantages.

One benefit is that use of the invention enables relatively simple and rapid expression of a desired recombinant biologically active protein in a eukaryotic cell of choice.

An advantage of the invention is that it provides a source of readily obtainable and purifiable recombinant biologically active protein due to the unique properties of expression in RPBLAs.

Another benefit of the invention is that the fusion protein-containing RPBLAs can be used for delivery of vaccines, including oral delivery.

Another advantage of the present invention is that the fusion protein-containing RPBLAs can be used as is in an immunogen in an injectable vaccine.

Another advantage of the present invention is that RPBLAs can be used as insulators, membrane-bound structures that isolate the expressed polypeptide from the rest of the cell components. These insulators protect the cell from the polypeptide activity, and the polypeptide from the cell, increasing the accumulation rate. Thus, difficult biologically-active polypeptides that are toxic and/or labile can be successfully expressed.

Still further benefits and advantages will be apparent to the skilled worker from the discussion that follows.

DETAILED DESCRIPTION OF THE INVENTION

A contemplated recombinant biologically active polypeptide is a portion of a fusion protein that forms recombinant protein body-like assemblies (RPBLAs), frequently membrane-enclosed, in the host cells in which they are expressed. RPBLA formation is induced by a protein body-inducing sequence (PBIS) comprised of a signal peptide and storage protein domain that forms high density deposits inside the cells. These dense deposits can accumulate in the cytosol, an endomenbrane system organelle, mitochondria, plastid or can be secreted. With the exception of certain cereal plant seeds, the eukaryotic host cell does not itself produce protein bodies (PBs) in the absence of the fusion protein. Thus, it is the expression of the fusion protein and its PBIS portion that causes the host cell to form protein body-like assemblies or RPBLAs.

A contemplated fusion protein comprises two polypeptide sequences linked together directly or indirectly by a peptide bond, in which one sequence is that of a protein body-inducing sequence (PBIS) linked to the second sequence that is a biologically active polypeptide product (e.g., peptide or protein) of interest (target). The biologically active polypeptide, as found in nature, is heterologous to the recited eukaryotic host cells and is thus expressed in a second cell type that is different from the first-mentioned eukaryotic host cell, or it is produced synthetically. That is, the biologically active polypeptide is heterologous to the recited eukaryotic host cells. PBIS are protein or polypeptide amino acid sequences that mediate the induction of RPBLA formation and the protein entry and/or accumulation in organelles such as the ER. The fusion protein when free and separated from the PBIS exhibits a biological activity similar to that of the polypeptide.

The biologically active polypeptide of the fusion protein exhibits at least 25 percent, preferably at least 50 percent, more preferably at least 75 percent and most preferably at least 90 percent of the biological activity of the same polypeptide isolated from the above second cell type, or synthesized in vitro. A material is considered "biologically active" or "bioactive" if it has interaction with or effect on any metabolite, protein, receptor, organelle, cell or tissue in an organism.

These biological activities can be readily determined and quantified using standard techniques for measuring the activity of that polypeptide. For example, assay results for biological activity between the polypeptide isolated from the second cell type, or synthesized in vitro, and the expressed polypeptide can be compared. When comparing the activity of a fusion protein, the proportion of that material provided by the PBIS and any linker sequence are taken into account in the assay comparison. Biological activity can be exhibited by the expressed RPBLAs, the fusion protein as a protein free of a surrounding membrane or as a target polypeptide that is free of its PBIS.

In a particular embodiment, the nucleic acid sequence used for transformation comprises (i) a nucleic acid sequence coding for a PBIS, and (ii) a nucleic acid sequence comprising the nucleotide sequence coding for a product of interest. In one embodiment, the 3' end of nucleic acid sequence (i) is linked to the 5' end of said nucleic acid sequence (ii). In another embodiment, the 5' end of nucleic acid sequence (i) is linked to the 3' end of nucleic acid sequence (ii). Thus, the PBIS sequence can be at the N-terminus or the C-terminus of the fusion protein. It is to be understood that all of the DNA linkages discussed herein for the expression of a fusion protein are such that the two components of the fusion protein are expressed in-frame.

Most protein bodies are round-shaped (generally spherical) structures, with diameters of about 0.5 to about 3.0µ. When expressed in animal cells, the RPBLAs are generally spherical in shape, have diameters of about 0.5 to about 3 microns (µ) and have a surrounding membrane. RPBLAs expressed in plants are also usually generally spherical, have diameters of about 0.5 to about 2µ, and are surrounded by a membrane. RPBLAs expressed in either plants, animals or fungi are derived from the ER if targeted there by an ER-specific secretion signal and accumulate externally to the ER envelope of the host cell following assembly. It is noted that EGF-containing RPBLAs expressed in the ER of plant cells were not generally spherical, and were amorphous in shape and of non-uniform size.

The recombinant protein body-like assemblies have a predetermined density that can differ among different fusion proteins, but is predictable across hosts for a particular fusion protein being prepared. That predetermined density of the RPBLAs is typically greater than that of substantially all of the endogenous host cell proteins present in the homogenate, and is typically about 1.1 to about 1.35 g/ml. The high density of novel RPBLAs is due to the general ability of the recombinant fusion proteins to self-assemble and accumulate into ordered aggregates associated with membranes. The contemplated RPBLAs are expressed in eukaryotes and can be characterized by their densities as noted above, and their size and shape.

The polypeptide portion of the fusion protein is believed to obtain its biological activity from folding and assembly within the ER, including disulfide bond formation, and in some instances from basal glycosylation in the ER. Interestingly, most plants and animals as well as lower eukaryotes such as fungi, N-glycosylate proteins in the same pattern based upon the tripeptide glycosylation recognition sequence Asn-X-Ser or Asn-X-Thr, where "X" is any amino acid residue but proline. Thus, a $Glc_3Man_9(GlcNAc)_2$ N-linked polypeptide is formed initially, and is trimmed back after formation to a $Man_{7-9}(GlcNAc)_2$ N-linked polypeptide that can be excreted to the Golgi or retained within the ER. This basal glycosylation is remarkably similar across eukaryotic genera. Further post-translational modification that are host-specific such as terminal glycosylation can occur in the Golgi for proteins not maintained in RPBLAs as are the fusion proteins contemplated here In this method, recombinant protein body-like assemblies (RPBLAs) are provided that typically comprise a membrane-enclosed fusion protein ordered assembly, and are preferably present in a generally spherical form having a diameter of about 0.5 to about 3 microns. The fusion protein contains two sequences linked together in which one sequence is a protein body-inducing sequence (PBIS) and the other is a biologically active polypeptide. The RPBLAs are contacted with an aqueous buffer containing a membrane-disassembling amount of a detergent (surfactant). That contact is maintained for a time period sufficient to disassemble the membrane and at a temperature that does not denature the biologically active polypeptide (e.g., above freezing to about 40° C.) to separate the membrane and fusion protein. The separated fusion protein is thereafter collected in a usual manner, or can be acted upon further without collection. Illustrative useful surfactants include Triton-X 100, CHAPS and the like are well-known in biochemistry for solubilizing lipids under mild conditions.

The separated fusion protein is typically in an insoluble form due to the interactions among the PBIS portions of the fusion protein mediated at least in part by the presence of cysteine residues. However, the polypeptide of interest is completed with eukaryotic chaperones and foldases derived from the ER and hence is held in a correctly folded conformation despite being tethered to the assembled (and hence insoluble) PBIS domain. The PBIS-PBIS interactions can be disrupted and the fusion protein solubilized by contacting the fusion protein with an aqueous buffer that contains a reducing agent such as dithiothreitol or 2-mercaptoethanol or β-mercaptoethanol (β-ME). Conditions are chosen so as to not disrupt and unfold the attached biologically active protein of interest. The separated, solubilized fusion protein that contains the biologically active polypeptide is then collected or otherwise used. In addition, the two portions of the fusion can be cleaved from each other upon solubilization. It is to be understood that that cleavage need not be at the exact borders between the two portions.

In some embodiments, the separated fusion protein exhibits the biological activity of the biologically active polypeptide. In other embodiments, the fusion protein is dissolved or dispersed in a suitable buffer to exhibit the biological activity of the polypeptide. For example, as discussed in detail hereinafter, human growth hormone (hGH) expressed in RPBLAs in mammalian cells exhibited activities substantially similar to that of the native polypeptide both when solubilized as a fusion protein directly from RPBLAs and also as a cleaved, isolated polypeptide produced from the fusion protein.

In yet other embodiments, for steric interaction or size reasons the fusion protein has to be cleaved into its constituent parts before biological activity of the polypeptide is revealed. Thus, the biologically active polypeptide can be linked to the PBIS by a by a spacer amino acid sequence that is cleavable by enzymatic or chemical means. Then, upon cleavage from the BPIS of the fusion protein and assay, the target (biologically active) polypeptide exhibits biological activity. Studies discussed hereinafter illustrate biological activity of the T-20 polypeptide cleaved from its fusion partner and produced in plants.

Protein Body-Inducing Sequences

A contemplated protein body-inducing sequences (PBIS) and the host cell are preferably of different biological phyla. Thus, the PBIS is preferably from a higher plant, a spermatophyte, whereas the host cell is a eukaryote that is other than a spermatophyte and can be an animal cell, as for instance mammalian or insect cells, a fungus, or an algal cell, all of which are of different phyla from spermatophytes. A PBIS and the host cell can also be from the same phylum so that both can be from a higher plant, for example. Illustrative, non-limiting examples of PBIS include storage proteins or modified storage proteins, as for instance, prolamins or modified prolamins, prolamin domains or modified prolamin domains. Prolamins are reviewed in Shewry et al., 2002 *J. Exp. Bot.* 53(370):947-958. Preferred PBIS are those of prolamin compounds such as gamma-zein, alpha-zein, delta-zein, beta-zein, rice prolamin and the gamma-gliadin that are discussed hereinafter.

A PBIS also includes a sequence that directs a protein towards the endoplasmic reticulum (ER) of a plant cell. That sequence often referred to as a leader sequence or signal peptide can be from the same plant as the remainder of the PBIS or from a different plant or an animal or fungus. Illustrative signal peptides are the 19 residue gamma-zein signal peptide sequence shown in WO 2004003207 (US 20040005660), the 19 residue signal peptide sequence of alpha-gliadin or 21 residue gamma-gliadin signal peptide sequence (see, Altschuler et al., 1993 *Plant Cell* 5:443-450; Sugiyama et al., 1986 *Plant Sci.* 44:205-209; and Rafalski et al., 1984 *EMBO J.* 3(6):1409-11415 and the citations therein.) The pathogenesis-related protein of PR10 class includes a 25 residue signal peptide sequence that is also useful herein. Similarly functioning signal peptides from other plants and animals are also reported in the literature.

The characteristics of the signal peptides responsible for directing the protein to the ER have been extensively studied (von Heijne et al., 2001 *Biochim. Biophys. Acta* December 12 1541(1-2):114-119). The signal peptides do not share homology at a primary structure, but have a common tripartite structure: a central hydrophobic h-region and hydrophilic N- and C-terminal flanking regions. These similarities, and the fact that proteins are translocated through the ER membrane using apparently common pathways, permits interchange of the signal peptides between different proteins or even from different organisms belonging to different phyla (See, Examples 1 and 2 hereinafter, and Martoglio et al., 1998 *Trends Cell Biol.* October; 8(10):410-415). Thus, a PBIS can include a signal peptide of a protein from a phylum different from higher plants.

Gamma-Zein, a maize storage protein whose DNA and amino acid residue sequences are shown hereinafter, is one of the four maize prolamins and represents 10-15 percent of the total protein in the maize endosperm. As other cereal prolamins, alpha- and gamma-zeins are biosynthesized in membrane-bound polysomes at the cytoplasmic side of the rough ER, assembled within the lumen and then sequestered into ER-derived protein bodies (Herman et al., 1999 *Plant Cell* 11:601-613; Ludevid et al., 1984 *Plant Mol. Biol.* 3:277-234; Torrent et al., 1986 *Plant Mol. Biol.* 7:93-403).

Gamma-Zein is composed of four characteristic domains i) a peptide signal of 19 amino acids, ii) the repeat domain containing eight units of the hexapeptide PPPVHL (SEQ ID NO:1) [(53 amino acid residues (aa)], iii) the ProX domain where proline residues alternate with other amino acids (29 aa) and iv) the hydrophobic cysteine rich C-terminal domain (111 aa).

The ability of gamma-zein to assemble in ER-derived RPBLAs is not restricted to seeds. In fact, when gamma-zein-gene was constitutively expressed in transgenic *Arabidopsis* plants, the storage protein accumulated within ER-derived PBLS in leaf mesophyl cells (Geli et al., 1994 *Plant Cell* 6:1911-1922). Looking for a signal responsible for the gamma-zein deposition into the ER-derived protein bodies (prolamins do not have KDEL signal for ER-retention), it has been demonstrated that the proline-rich N-terminal domain including the tandem repeat domain was necessary for ER retention. In this work, it was also suggested that the C-terminal domain could be involved in protein body formation, however, recent data (WO2004003207A1) demonstrate that the proline-rich N-terminal domain is necessary and sufficient to retain in the ER and to induce the protein body formation. However, the mechanisms by which these domains promote the protein body assembly are still unknown, but evidence from in vitro studies suggests that the N-terminal portion of gamma-zein is able to self-assemble into ordered structures.

It is preferred that a gamma-zein-based PBIS include at least one repeat and the amino-terminal nine residues of the ProX domain, and more preferably the entire Pro-X domain. The C-terminal portion of gamma-zein is not needed, but can be present. Those sequences are shown in US 20040005660 and designated as RX3 and P4, respectively, and are noted hereinafter.

Inasmuch as PBs are appropriately so-named only in seeds, similar structures produced in other plant organs and in non-higher plants are referred to generally as synthetic PBs or recombinant protein body-like assemblies (RPBLAs).

Zeins are of four distinct types: alpha, beta, delta, and gamma. They accumulate in a sequential manner in the ER-derived protein bodies during endosperm development. Beta-zein and delta-zein do not accumulate in large amount in maize PBs, but they were stable in the vegetative tissues and were deposited in ER-derived protein body-like structures when expressed in tobacco plants (Bagga et al., 1997 *Plant Cell* September 9(9):1683-1696). This result indicates that beta-zein, as well as delta-zein, can induce ER retention and PB formation.

The wheat prolamin storage proteins, gliadins, are a group of K/HDEL-less proteins whose transport via the ER appears to be complex. These proteins sequester in to the ER where they are either retained and packaged into dense protein bodies, or are transported from the ER via the Golgi into vacuoles. (Altschuler et al., 1993 *Plant Cell* 5:443-450.)

The gliadins appear to be natural chimeras, containing two separately folded autonomous regions. The N-terminus is composed of about 7 to about 16 tandem repeats rich in glutamine and proline. The sequence of the tandem repeats varies among the different gliadins, but are based on one or the other consensus sequences PQQPFPQ (SEQ ID NO:47), PQQQPPFS (SEQ ID NO:48) and PQQPQ (SEQ ID NO:49). The C-terminal region of the protein contains six to eight cysteines that form intramolecular disulfide bonds. The work of the Altschuler et al. indicates that the N-terminal region and consensus sequences are responsible for PB formation in the ER from gamma-gliadin. (Altschuler et al., 1993 *Plant Cell* 5:443-450.)

Illustrative useful prolamin-type sequences are shown in the Table below along with their GenBank identifiers.

| PROTEIN NAME | GENBANK ID |
| --- | --- |
| α-Zein (22 kD) | M86591 |
| Albumin (32 kD) | X70153 |
| γ-Zein (27 kD) | X53514 |
| γ-Zein (50 kD) | AF371263 |
| δ-Zein (18 kD) | AF371265 |
| 7S Globulin or Vicilin type | NM_113163 |
| 11S Globulin or Legumin type | DQ256294 |
| Prolamin 13 kD | AB016504 |
| Prolamin 16 kD | AY427574 |
| Prolamin 10 kD | AF294580 |
| γ-Gliadin | M36999 |
| γ-Gliadin precursor | AAA34272 |

Further useful sequences are obtained by carrying out a BLAST search in the all non-redundant GenBank CDS translations+PDB+SwissProt+PIR+PRF (excluding environmental samples) data base as described in Altschul et al., 1997 *Nucleic Acids Res.* 25:3389-3402 using a query such as those shown below:

```
RX3 query
                                          SEQ ID NO:2
PPPPVHLPPPVHLPPPVHLPPPVHLPPPVHLPPPVHLPPPVHVPPPVHLP
PPP Alpha- zein
                                          SEQ ID NO:3
QQQQQFLPALSQLDVVNPVAYLQQQLLASNPLALANVAAYQQQQQLQQFL
PALSQLAMVNPAAYL Rice prolamin query
                                          SEQ ID NO:4
QQVLSPYNEFVRQQYGIAASPFLQSATFQLRNNQVWQQLALVAQQSHCQD
INIVQAIAQQLQLQQFGDLY
```

An illustrative modified prolamin includes (a) a signal peptide sequence, (b) a sequence of one or more copies of the repeat domain hexapeptide PPPVHL (SEQ ID NO: 1) of the protein gamma-zein, the entire domain containing eight hexapeptide units; and (c) a sequence of all or part of the ProX domain of gamma-zein. Illustrative specific modified prolamins include the polypeptides identified below as R3, RX3 and P4 whose DNA and amino acid residue sequences are also shown below.

Particularly preferred prolamins include gamma-zein and its component portions as disclosed in published application WO2004003207, the rice rP13 protein and the 22 kDa maize alpha-zein and its N-terminal fragment. The DNA and amino acid residue sequences of the gamma-zein, rice and alpha-zein proteins are shown below.

```
Gamma-zein of 27 kD
DNA Sequence:
                                          SEQ ID NO:5
atgagggtgt tgctcgttgc cctcgctctc ctggctctcg  40
ctgcgagcgc cacctccacg catacaagcg gcggctgcgg  80
ctgccagcca ccgccgccgg ttcatctacc gccgccggtg 120
catctgccac ctccggttca cctgccacct ccggtgcatc 160
tcccaccgcc ggtccacctg ccgccgccgg tccacctgcc 200
accgccggtc catgtgccgc cgccggttca tctgccgccg 240
ccaccatgcc actaccctac tcaaccgccc cggcctcagc 280
ctcatcccca gccacaccca tgcccgtgcc aacagccgca 320
tccaagcccg tgccagctgc agggaacctg cggcgttggc 360
agcaccccga tcctgggcca gtgcgtcgag tttctgaggc 400
atcagtgcag cccgacggcg acgccctact gctcgcctca 440
gtgccagtcg ttgcggcagc agtgttgcca gcagctcagg 480
caggtggagc cgcagcaccg gtaccaggcg atcttcggct 520
tggtcctcca gtccatcctg cagcagcagc cgcaaagcgg 560
ccaggtcgcg gggctgttgg cggcgcagat agcgcagcaa 600
ctgacggcga tgtgcggcct gcagcagccg actccatgcc 640
cctacgctgc tgccggcggt gtcccccacg cc           672

Protein Sequence:
                                          SEQ ID NO:6
          Met Arg Val Leu Leu Val Ala Leu Ala Leu Leu Ala Leu Ala Ala Ser
          1               5                  10                  15
```

-continued

```
Ala Thr Ser Thr His Thr Ser Gly Gly Cys Gly Cys Gln Pro Pro
            20                  25                  30

Pro Val His Leu Pro Pro Val His Leu Pro Pro Val His Leu
        35                  40                  45

Pro Pro Pro Val His Leu Pro Pro Val His Leu Pro Pro Val
    50                  55                  60

His Leu Pro Pro Val His Val Pro Pro Val His Leu Pro Pro
 65                  70                  75                  80

Pro Pro Cys His Tyr Pro Thr Gln Pro Arg Pro Gln Pro His Pro
            85                  90                  95

Gln Pro His Pro Cys Pro Cys Gln Gln Pro His Pro Ser Pro Cys Gln
            100                 105                 110

Leu Gln Gly Thr Cys Gly Val Gly Ser Thr Pro Ile Leu Gly Gln Cys
            115                 120                 125

Val Glu Phe Leu Arg His Gln Cys Ser Pro Thr Ala Thr Pro Tyr Cys
 130                 135                 140

Ser Pro Gln Cys Gln Ser Leu Arg Gln Gln Cys Gln Gln Leu Arg
 145                 150                 155                 160

Gln Val Glu Pro Gln His Arg Tyr Gln Ala Ile Phe Gly Leu Val Leu
            165                 170                 175

Gln Ser Ile Leu Gln Gln Pro Gln Ser Gly Gln Val Ala Gly Leu
            180                 185                 190

Leu Ala Ala Gln Ile Ala Gln Gln Leu Thr Ala Met Cys Gly Leu Gln
            195                 200                 205

Gln Pro Thr Pro Cys Pro Tyr Ala Ala Ala Gly Gly Val Pro His Ala
            210                 215                 220
```

RX3
DNA Sequence:
SEQ ID NO:7

```
atgagggtgt tgctcgttgc cctcgctctc ctggctctcg   40
ctgcgagcgc cacctccacg catacaagcg gcggctgcgg   80
ctgccagcca ccgccgccgg ttcatctacc gccgccggtg  120
catctgccac ctccggttca cctgccacct ccggtgcatc  160
tcccaccgcc ggtccacctg ccgccgccgg tccacctgcc  200
accgccggtc catgtgccgc cgccggttca tctgccgccg  240
ccaccatgcc actaccctac tcaaccgccc cggcctcagc  280
ctcatcccca gccacaccca tgcccgtgcc aacagccgca  320
tccaagcccg tgccagacc                         339
```

Protein Sequence:
SEQ ID NO:8

```
Met Arg Val Leu Leu Val Ala Leu Ala Leu Leu Ala Leu Ala Ala Ser
 1               5                  10                  15

Ala Thr Ser Thr His Thr Ser Gly Gly Cys Gly Cys Gln Pro Pro
            20                  25                  30

Pro Val His Leu Pro Pro Val His Leu Pro Pro Val His Leu
        35                  40                  45

Pro Pro Pro Val His Leu Pro Pro Val His Leu Pro Pro Val
    50                  55                  60

His Leu Pro Pro Val His Val Pro Pro Val His Leu Pro Pro
 65                  70                  75                  80
```

-continued

Pro Pro Cys His Tyr Pro Thr Gln Pro Pro Arg Pro Gln Pro His Pro
            85                  90                  95

Gln Pro His Pro Cys Pro Cys Gln Gln Pro His Pro Ser Pro Cys Gln
            100                 105                 110

Tyr

R3
DNA Sequence:
                                                        SEQ ID NO:9
atgagggtgt tgctcgttgc cctcgctctc ctggctctcg  40
ctgcgagcgc cacctccacg catacaagcg gcggctgcgg  80
ctgccagcca ccgccgccgg ttcatctacc gccgccggtg  120
catctgccac ctccggttca cctgccacct ccggtgcatc  160
tcccaccgcc ggtccacctg ccgccgccgg tccacctgcc  200
accgccggtc catgtgccgc cgccggttca tctgccgccg  240

Protein Sequence:
                                                        SEQ ID NO:10
Met Arg Val Leu Leu Val Ala Leu Ala Leu Leu Ala Leu Ala Ala Ser
 1               5                   10                  15

Ala Thr Ser Thr His Thr Ser Gly Gly Cys Gly Cys Gln Pro Pro Pro
            20                  25                  30

Pro Val His Leu Pro Pro Pro Val His Leu Pro Pro Val His Leu
            35                  40                  45

Pro Pro Pro Val His Leu Pro Pro Val His Leu Pro Pro Val
       50                   55                  60

His Leu Pro Pro Pro Val His Val Pro Pro Pro Val His Leu Pro Pro
 65                  70                  75                  80

Pro Pro Cys His Tyr Pro Thr Gln Pro Pro Arg Tyr
            85                  90

P4
DNA Sequence:
                                                        SEQ ID NO:11
atgagggtgt tgctcgttgc cctcgctctc ctggctctcg  40
ctgcgagcgc cacctccacg catacaagcg gcggctgcgg  80
ctgccagcca ccgccgccgg ttcatctgcc gccgccacca  120
tgccactacc ctacacaacc gccccggcct cagcctcatc  160
cccagccaca cccatgcccg tgccaacagc cgcatccaag  200
cccgtgccag acc                              213

Protein Sequence:
                                                        SEQ ID NO:12
Met Arg Val Leu Leu Val Ala Leu Ala Leu Leu Ala Leu Ala Ala Ser
 1               5                   10                  15

Ala Thr Ser Thr His Thr Ser Gly Gly Cys Gly Cys Gln Pro Pro
            20                  25                  30

Pro Val His Leu Pro Pro Pro Cys His Tyr Pro Thr Gln Pro Pro
            35                  40                  45

Arg Pro Gln Pro His Pro Gln Pro His Pro Cys Pro Cys Gln Gln Pro
       50                   55                  60

His Pro Ser Pro Cys Gln Tyr
 65                  70 x10

```
DNA Sequence:
                                              SEQ ID NO:13
atgagggtgt tgctcgttgc cctcgctctc ctggctctcg    40
ctgcgagcgc cacctccacg catacaagcg gcggctgcgg    80
ctgccaatgc cactacccta ctcaaccgcc ccggcctcag   120
cctcatcccc agccacaccc atgcccgtgc caacagccgc   160
atccaagccc gtgccagacc                         180

Protein Sequence:
                                              SEQ ID NO:14
Met Arg Val Leu Leu Val Ala Leu Ala Leu Leu Ala Leu Ala Ala Ser
 1               5                  10                  15

Ala Thr Ser Thr His Thr Ser Gly Gly Cys Gly Cys Gln Cys His Tyr
             20                  25                  30

Pro Thr Gln Pro Pro Arg Pro Gln Pro His Pro Gln Pro His Pro Cys
         35                  40                  45

Pro Cys Gln Gln Pro His Pro Ser Pro Cys Gln Tyr
     50                  55                  60
``` rP13—rice prolamin of 13 kD homologous to the clone—AB016504 Sha et al., 1996 *Biosci. Biotechnol. Biochem.* 60(2):335-337; Wen et al., 1993 *Plant Physiol.* 101(3):1115-1116; Kawagoe et al., 2005 *Plant Cell* 17(4):1141-1153; Mullins et al., 2004 *J. Agric. Food Chem.* 52(8):2242-2246; Mitsukawa et al., 1999 *Biosci. Biotechnol. Biochem.* 63(11):1851-1858

```
Protein Sequence:
                                              SEQ ID NO:15
MKIIFVFALLAIAACSASAQFDVLGQSYRQYQLQSPVLLQQQVLSPYNEF

VRQQYGIAASPFLQSATFQLRNNQVWQQLALVAQQSHCQDINIVQAIAQQ

LQLQQFGDLYFDRNLAQAQALLAFNVPSRYGIYPRYYGAPSTITTLGGVL

DNA Sequence:
                                              SEQ ID NO:16
atgaagatca tttttcgtct tttgctctcc ttgctattgc tgcatgcagc gc ctctgcgca gtttgatgtt ttaggtcaaa gttataggca atatcagctg c agtcgcctg tcctgctaca gcaacaggtg cttagcccat ataatgagtt c gtaaggcag cagtatggca tagcggcaag ccccttcttg caatcagcta c gtttcaact gagaaacaac caagtctggc aacagctcgc gctggtggcg c aacaatctc actgtcagga cattaacatt gttcaggcca tagcgcagca g ctacaactc cagcagtttg gtgatctcta ctttgatcgg aatctggctc a agctcaagc tctgttggct tttaacgtgc catctagata tggtatctac c ctaggtact atggtgcacc cagtaccatt accaccttgg cggtgtcttg
```

22aZt N-terminal fragment of the maize alpha-zein of 22 kD—V01475 Kim et al., 2002 *Plant Cell* 14(3):655-672; Woo et al., 2001 *Plant Cell* 13(10):2297-2317; Matsushima et al., 1997 *Biochim. Biophys. Acta* 1339(1):14-22; Thompson et al., 1992 *Plant Mol. Biol.* 18 (4):827-833.

```
Protein Sequence (full length)
                                              SEQ ID NO:17
MATKILALLALLALFVSATNAFIIPQCSLAPSAIIPQFLPPVTSMGFEHL

AVQAYRLQQALAASVLQQPINQLQQQSLAHLTIQTIATQQQQQFLPALSQ

LDVVNPVAYLQQQLLASNPLALANVAAYQQQQQLQQFLPALSQL

DNA Sequence (full length):
                                              SEQ ID NO:18
atggctacca agatattagc cctccttgcg cttcttgccc tttttgtgag cgcaacaaat gcgttcatta ttccacaatg ctcacttgct cctagtgcca ttataccaca gttcctccca ccagttactt caatgggctt cgaacaccta gctgtgcaag cctacaggct acaacaagcg cttgcggcaa gcgtcttaca acaaccaatt aaccaattgc aacaacaatc ccttggcaca tctaaccatac aaaccatcgc aacgcaacag caacaacagt tcctaccagc actgagccaa ctagatgtgg taaccctgtc gcctacttgc aacagcagct gcttgcatc caacccacttg ctctggcaaa cgtagctgca taccaacaac aacaacaat tgcagcagtt tctgccagcg ctcagtcaacta
```

Gamma-Gliadin precursor—AAA34272—Scheets et al., 1988 *Plant Sci.* 57:141-150.

```
Protein Sequence:
                                              SEQ ID NO:19
NMQVDPSGQV QWPQQQPFPQ PQQPFCQQPQ RTIPQPHQTF HHQPQQTFPQ

PQQTYPHQPQ QQFPQTQQPQ QPFPQPQQTF PQQPQLPFPQ QPQQPFPQPQ

QPQQPFPQSQ QPQQPFPQPQ QQFPQPQQPQ QSFPQQQQPA IQSFLQQQMN

PCKNFLLQQC NHVSLVSSLV SIILPRSDCQ VMQQQCCQQL AQIPQQLQCA
```

-continued

AIHSVAHSII MQQEQQQGVP ILRPLFQLAQ GLGIIQPQQP AQLEGIRSLV

LKTLPTMCNV YVPPDCSTIN VPYANIDAGI

GGQ

DNA Sequence (M36999)

SEQ ID NO:20 gcatgcattg tcaaagtttg tgaagtagaa ttaataacct tttggttatt gatcactgta tgtatcttag atgtcccgta gcaacggtaa gggcattcac ctagtactag tccaatatta attaataact tgcacagaat tacaaccatt gacataaaaa ggaaatatga tgagtcatgt attgattcat gttcaacatt actacccttg acataaaaga agaatttgac gagtcgtatt agcttgttca tcttaccatc atactatact gcaagctagt ttaaaaaaga atyaaagtcc agaatgaaca gtagaatagc ctgatctatc tttaacaaca tgcacaagaa tacaaattta gtcccttgca agctatgaag atttggttta tgcctaacaa catgataaac ttagatccaa aaggaatgca atctagataa ttgtttgact tgtaaagtcg ataagatgag tcagtgccaa ttataaagtt ttcgccactc ttagatcata tgtacaataa aaaggcaact ttgctgacca ctccaaaagt acgtttgtat gtagtgccac caaacacaac acaccaaata atcagtttga taagcatcga atcactttaa aaagtgaaaa aaataatgaa aagaaaccta accatggtag ctataaaaag cctgtaatat gtacactcca taccatcatc catccttcac acaactagag cacaagcatc aaatccaagt aagtattagt t aacgcaaat ccaccatgaa gaccttactc atcctaacaa tccttgcgat ggcaacaacc atcgccaccg ccaatatgca agtcgacccc agcggccaag tacaatggcc acaacaacaa ccattccccc agccccaaca accattctgc cagcaaccac aacgaactat tccccaaccc catcaaacat tccaccatca accacaacaa acatttcccc aaccccaaca aacataccccc catcaaccac aacaacaatt tccccagacc caacaaccac aacaaccatt tccccagccc caacaaacat tcccccaaca accccaacta ccatttcccc aacaacccca acaaccattc ccccagcctc agcaacccca acaaccattt ccccagtcac aacaaccaca acaaccttt ccccagcccc aacaacaatt tccgcagccc caacaaccac aacaatcatt cccccaacaa caacaaccgg cgattcagtc atttctacaa caacagatga accctgcaa gaatttcctc ttgcagcaat gcaaccatgt gtcattggtg tcatctctcg tgtcaataat tttgccacga agtgattgcc aggtgatgca gcaacaatgt tgccaacaac tagcacaaat tcctcaacag ctccagtgcg cagccatcca cagcgtcgcg cattccatca tcatgcaaca agaacaacaa caaggcgtgc cgatcctgcg gccactattt cagctcgccc agggtctggg tatcatccaa cctcaacaac cagctcaatt ggaggggatc aggtcattgg tattgaaaac tcttccaacc atgtgcaacg tgtatgtgcc acctgactgc tccaccatca acgtaccata tgccaacata gacgctggca ttggtggcca atgaaaaatg caagatcatc attgcttagc tgatgcacca atcgttgtag cgatgacaaa taaagtggtg tgcaccatca tgtgtgaccc cgaccagtgc tagttcaagc ttgggaataa aagacaaaca aagttcttgt ttgctagcat tgcttgtcac

```
tgttacattc acttttatt tcgatgttca tccctaaccg caatcctagc cttacacgtc aatagctagc tgcttgtgct ggcaggttac tatataatct atcaattaat ggtcgaccta ttaatccaag taataggcta ttgatagact gctcccaagc cgaccgagca cctatcagtt acggatttct tgaacattgc acactataat aattcaacgt atttcaacct ctagaagtaa agggcatttt agtagc
```

Beta zein—AF371264—Woo et al., (2001) Plant Cell 13 (10), 2297-2317.

DNA
SEQ ID NO:21
```
atgaagatggtcatcgttctcgtcgtgtgcctggctctgtcagctgccag cgcctctgcaatgcagatgccctgcccctgcgcggggctgcagggcttgt acggcgctggcgccggcctgacgacgatgatgggcgccggcgggctgtac ccctacgcggagtacctgaggcagccgcagtgcagcccgctggcggcggc gccctactacgccgggtgtgggcagccgagcgccatgttccagccgctcc ggcaacagtgctgccagcagcagatgaggatgatggacgtgcagtccgtc gcgcagcagctgcagatgatgatgcagcttgagcgtgccgctgccgccag cagcagcctgtacgagccagctctgatgcagcagcagcagcagctgctgg cagcccagggtctcaacccatggccatgatgatggcgcagaacatgccg gccatgggtggactctaccagtaccagctgcccagctaccgcaccaaccc ctgtggcgtctccgctgccattccgccctactactga
```

Protein
SEQ ID NO:22
MKMVIVLVVCLALSAASASAMQMPCPCAGLQGLYGAGAGLTTMMGAGGLY

PYAEYLRQPQCSPLAAAPYYAGCGQPSAMFQPLRQQCCQQQMRMMDVQSV

AQQLQMMMQLERAAAASSSLYEPALMQQQQQLLAAQGLNPMAMMMAQNMP

AMGGLYQYQLPSYRTNPCGVSAAIPPYY

Delta zein 10 kD—AF371266—Woo et al., (2001) Plant Cell 13 (10), 2297-2317. and Kirihara et al., (1988) Gene. November 30; 71(2):359-70.

DNA
SEQ ID NO:23
```
atggcagccaagatgcttgcattgttcgctctcctagctctttgtgcaag cgccactagtgcgacgcatattccagggcacttgccaccagtcatgccat tgggtaccatgaacccatgcatgcagtactgcatgatgcaacaggggctt gccagcttgatggcgtgtccgtccctgatgctgcagcaactgttggcctt accgcttcagacgatgccagtgatgatgccacagatgatgacgcctaaca tgatgtcaccattgatgatgccgagcatgatgtcaccaatggtcttgccg agcatgatgtcgcaaatgatgatgccacaatgtcactgcgacgccgtctc gcagattatgctgcaacagcagttaccattcatgttcaacccaatggcca tgacgattccacccatgttcttacagcaacccttgttggtgctgcattc tag
```

Protein
SEQ ID NO:24
MAAKMLALFALLALCASATSATHIPGHLPPVMPLGTMNPCMQYCMMQQGL

ASLMACPSLMLQQLLALPLQTMPVMMPQMMTPNMMSPLMMPSMMSPMVLP

SMMSQMMMPQCHCDAVSQIMLQQQLPFMFNPMAMTIPPMFLQQPFVGAAF

Signal Peptides
Gamma-Zein
SEQ ID NO:25
Met Arg Val Leu Leu Val Ala Leu Ala Leu Leu Ala Leu Ala Ala Ser Ala Thr Ser Alpha-Gliadin
SEQ ID NO:26
Met Lys Thr Phe Leu Ile Leu Val Leu Leu Ala Ile Val Ala Thr Thr Ala Thr Thr Ala Gamma-Gliadin
SEQ ID NO:27
Met Lys Thr Leu Leu Ile Leu Thr Ile Leu Ala Met Ala Ile Thr Ile Gly Thr Ala Asn Met PR10
SEQ ID NO:28
Met Asn Phe Leu Lys Ser Phe Pro Phe Tyr Ala Phe Leu Cys Phe Gly Gln Tyr Phe Val Ala Val Thr His Ala Proteins of Interest Examples of polypeptides or proteins of interest (targets) include any protein having therapeutic, nutraceutical, agricultural, or industrial uses. Illustrative activities of such proteins include (a) light capture and emission as are provided by green fluorescent protein (GFP), enhanced cyan fluorescent protein (ECFP), red fluorescent protein (DsRed) and the like; (b) enzymatic activity that can be associated with primary and secondary intracellular signaling and metabolic pathways, is exemplified by enterokinase, beta-glucuronidase (GUS), phytase, carbonic anhydrase, and industrial enzymes (hydrolases, glycosidases, cellulases, oxido-reductases, and the like); (c) protein-protein, protein-receptor, and protein-ligand interaction such as, for example antibodies (mAbs such as IgG, IgM, IgA, etc.) and fragments thereof, hormones [calcitonin, human growth hormone (hGH), epidermal growth factor (EGF) and the like], protease inhibitors, antibiotics, antimicrobials, HIV entry inhibitors [Ryser et al., 2005 *Drug Discov Today*. August 15; 10(16):1085-1094], collagen, human lactoferrin, and cytokines; (d) protein and peptides antigens for vaccines (human immunodeficiency virus, HIV; hepatitis B pre-surface, surface and core antigens, Foot and Mouth Disease Virus (FMDV) structural polyprotein gene P1 [Dus Santos et al., 2005 *Vaccine*. March 7; 23(15):1838-1843] T cell stimulating peptides of U.S. Pat. No. 4,882,145, gastroenteritis corona virus, human papilloma virus, and the like); (e) protein-non protein interactions such as, phytohaemagglutinin (PHA), the Ricin Toxin subunit B (RTB) and other lectins.

Assays for the bioactivity of such expressed polypeptides are well known in the art and are available in one or more publications. For example, ECFP activity can be measured by quantifying the fluorescence emitted at a 470-530 nm wavelength when the protein has been exited at 458 nm. See, Richards et al., 2003 *Plant Cell Rep.* 22:117-121. The enzymatic activity of enterokinase (EK), for example, can be measured with two different approaches. The activity can be determined by analyzing the cleavage of a fusion protein containing the enterokinase specific cleavage site by western blot, as discussed in the Invitrogen Life Technologies catalog (E180-01 and E180-2), and also by quantifying the EK activity using fluorogenic peptide substrate for EK (Sigma G-5261, CAS® RN 70023-02-8); enzyme activity is measured by an increase of fluorescence (excitation at 337 nm, emission at 420 nm) caused by the release of β-naphthylamine from the peptide over time. See, LaVallie et al., 1993 *J. Biol. Chem.* 268(31):23311-23317. The activity of the enzyme beta-glucuronidase (GUS) can be measured by the conversion of the substrate MUG (4-methyl umbelliferyl glucuronide) to the product MU. This product can be quantified by measuring the fluorescence with excitation at 365 nm, emission at 455 nm on a spectrofluorimeter. See, Pai-Hsiang et al., 2001 *J. Plant Physiol.* 158(2):247-254; and Jefferson et al., 1987 *EMBO J.* 6:3901-3907. Phytase assays are carried out by the quantification of inorganic ortho phosphates liberated from the AAM reagent consisting of acetone, 5.0 N sulfuric acid, and 10 mM ammonium molybdate. See, Ullah et al., 1999 *Biochem. Biophys. Res. Commun.* 264(1):201-206. Similar assays are available for other biological proteins. The RTB activity assays can be performed by measuring the binding of RTB to asialofetuin, lactose and galactose, as described in Reed et al., 2005 *Plant Cell Rep.* April; 24(1): 15-24.

EGF is a growth factor involved in fibroblasts proliferation. EGF activity can be assayed by the quantification of the induction of DNA synthesis measured by incorporation of the pyrimidine analog 5-bromo-2'-deoxyuridine (BrdU), instead of thymidine, into the DNA of proliferating cells using the cell proliferation ELISA kit [Oliver, et al., 2004 *Am. J. Physiol. Cell Physiol.* 286:1118-1129; Catalog no. 1647229, Roche Diagnostics, Mannheim, Germany]

It is noted that light capture and emission constitutes a separate and special type of "biological activity" in that such activity does not provide therapeutic, nutraceutical, agricultural, or industrial use as do the other types of activity noted above. The polypeptides of this class of targets are included herein as biologically active because they share some of the required secondary, tertiary and quaternary structural features that are possessed by the target molecules that provide therapeutic, nutraceutical, agricultural, or industrial uses. These proteins are useful, however, as reporter molecules in many types of assays or screens used in the analysis or discovery of biologically important molecules, and their luminescent activity requires the presence of correct secondary and tertiary protein structure. It is possibly more accurate to refer to the group of targets as those polypeptides that are biologically active and/or luminescently active.

Illustrative DNA and amino acid residue sequences for illustrative proteins of interest are provided below.

ECFP

SEQ ID NO:29 atggtgagcaagggcgaggagctgttcaccggggtggtgcccatcctggt cgagctggacggcgacgtaaacggccacaagttcagcgtgtccggcgagg gcgagggcgatgccacctacggcaagctgaccctgaagttcatctgcacc accggcaagctgcccgtgccctggcccaccctcgtgaccaccctgacctg gggcgtgcagtgcttcagccgctaccccgaccacatgaagcagcacgact tcttcaagtccgccatgcccgaaggctacgtccaggagcgcaccatcttc ttcaaggacgacggcaactacaagacccgcgccgaggtgaagttcgaggg cgacaccctggtgaaccgcatcgagctgaagggcatcgacttcaaggagg acggcaacatcctggggcacaagctggagtacaactacatcagccacaac gtctatatcaccgccgacaagcagaagaacggcatcaaggccaacttcaa gatccgccacaacatcgaggacggcagcgtgcagctcgccgaccactacc agcagaacacccccatcggcgacggccccgtgctgctgcccgacaaccac tacctgagcacccagtccgccctgagcaaagaccccaacgagaagcgcga tcacatggtcctgctggagttcgtgaccgccgcgggatcactctcggca tggacgagctgtacaagtaa

ECFP

SEQ ID NO:30

MVSKGEELFTGVVPILVELDGDVNGHKFSVSGEGEGDATYGKLTLKFICT

TGKLPVPWPTLVTTLTWGVQCFSRYPDHMKQHDFFKSAMPEGYVQERTIF

FKDDGNYKTRAEVKFEGDTLVNRIELKGIDFKEDGNILGHKLEYNYISHN

VYITADKQKNGIKANFKIRHNIEDGSVQLADHYQQNTPIGDGPVLLPDNH

YLSTQSALSKDPNEKRDHMVLLEFVTAAGITLGMDELYK

GUS1381

SEQ ID NO:31 atggtagatctgactagtttacgtcctgtagaaaccccaacccgtgaaat caaaaaactcgacggcctgtgggcattcagtctggatcgcgaaaactgtg gaattgatcagcgttggtgggaaagcgcgttacaagaaagccgggcaatt gctgtgccaggcagttttaacgatcagttcgccgatgcagatattcgtaa ttatgcgggcaacgtctggtatcagcgcgaagtctttataccgaaaggtt gggcaggccagcgtatcgtgctgcgtttcgatgcggtcactcattacggc aaagtgtgggtcaataatcaggaagtgatggagcatcagggcggctatac gccatttgaagccgatgtcacgccgtatgttattgccgggaaaagtgtac gtatcaccgtttgtgtgaacaacgaactgaactggcagactatcccgccg ggaatggtgattaccgacgaaaacggcaagaaaaagcagtcttacttcca tgatttctttaactatgccggaatccatcgcagcgtaatgctctacacca cgccgaacacctgggtggacgatatcaccgtggtgacgcatgtcgcgcaa gactgtaaccacgcgtctgttgactggcaggtggtggccaatggtgatgt cagcgttgaactgcgtgatgcggatcaacaggtggttgcaactggacaag gcactagcgggactttgcaagtggtgaatccgcacctctggcaaccgggt gaaggttatctctatgaactgtgcgtcacagccaaaagccagacagagtg tgatatctacccgcttcgcgtcggcatccggtcagtggcagtgaagggcc aacagttcctgattaaccacaaaccgttctactttactggctttggtcgt catgaagatgcggacttacgtggcaaaggattcgataacgtgctgatggt gcacgaccacgcattaatggactggattggggccaactcctaccgtacct cgcattacccttacgctgaagagatgctcgactgggcagatgaacatggc atcgtggtgattgatgaaactgctgctgtcggctttcagctgtctttagg cattggtttcgaagcgggcaacaagccgaaagaactgtacagcgaagagg cagtcaacggggaaactcagcaagcgcacttacaggcgattaaagagctg atagcgcgtgacaaaaaccacccaagcgtggtgatgtggagtattgccaa cgaaccggatacccgtccgcaaggtgcacgggaatatttcgcgccactgg cggaagcaacgcgtaaactcgacccgacgcgtccgatcacctgcgtcaat gtaatgttctgcgacgctcacaccgataccatcagcgatctctttgatgt gctgtgcctgaaccgttattacggatggtatgtccaaagcggcgatttgg aaacggcagagaaggtactggaaaaagaacttctggcctggcaggagaaa ctgcatcagccgattatcatcaccgaatacggcgtggatacgttagccgg gctgcactcaatgtacaccgacatgtggagtgaagagtatcagtgtgcat ggctggatatgtatcaccgcgtctttgatcgcgtcagcgccgtcgtcggt gaacaggtatggaatttcgccgattttgcgacctcgcaaggcatattgcg cgttggcggtaacaagaaagggatcttcactcgcgaccgcaaaccgaagt cggcggcttttctgctgcaaaaacgctggactggcatgaacttcggtgaa aaaccgcagcagggaggcaaacaagctagccaccaccaccaccaccacgt gtga

GUS1381

SEQ ID NO:32

MVDLTSLRPVETPTREIKKLDGLWAFSLDRENCGIDQRWWESALQESRAI

AVPGSFNDQFADADIRNYAGNVWYQREVFIPKGWAGQRIVLRFDAVTHYG

KVWVNNQEVMEHQGGYTPFEADVTPYVIAGKSVRITVCVNNELNWQTIPP

GMVITDENGKKKQSYFHDFFNYAGIHRSVMLYTTPNTWVDDITVVTHVAQ

DCNHASVDWQVVANGDVSVELRDADQQVVATGQGTSGTLQVVNPHLWQPG

EGYLYELCVTAKSQTECDIYPLRVGIRSVAVKGQQFLINHKPFYFTGFGR

HEDADLRGKGFDNVLMVHDHALMDWIGANSYRTSHYPYAEEMLDWADEHG

IVVIDETAAVGFQLSLGIGFEAGNKPKELYSEEAVNGETQQAHLQAIKEL

IARDKNHPSVVMWSIANEPDTRPQGAREYFAPLAEATRKLDPTRPITCVN

VMFCDAHTDTISDLFDVLCLNRYYGWYVQSGDLETAEKVLEKELLAWQEK

LHQPIIITEYGVDTLAGLHSMYTDMWSEEYQCAWLDMYHRVFDRVSAVVG

EQVWNFADFATSQGILRVGGNKKGIFTRDRKPKSAAFLLQKRWTGMNFGE

KPQQGGKQASHHHHHHV

GUS1391Z

SEQ ID NO:33 atggtagatctgagggtaaatttctagttttttctccttcatttttcttggt taggaccctttttctcttttttatttttttttgagctttgatctttctttaaac tgatctatttttttaattgattggttatggtgtaaatattacatagcttta actgataatctgattacttttatttcgtgtgtctatgatgatgatgatagt tacagaaccgacgactcgtccgtcctgtagaacgtgaaatcaaaaaactc gacggcctgtgggcattcagtctggatcgcgaaaactgtggaattgatca gcgttggtgggaaagcgcgttacaagaaagccgggcaattgctgtgccag gcagttttaacgatcagttcgccgatgcagatattcgtaattatgcgggc aacgtctggtatcagcgcgaagtctttataccgaaaggttgggcaggcca gcgtatcgtgctgcgtttcgatgcggtcactcattacggcaaagtgtggg tcaataatcaggaagtgatggagcatcagggcggctatacgccatttgaa gccgatgtcacgccgtatgttattgccgggaaaagtgtacgtatcaccgt ttgtgtgaacaacgaactgaactggcagactatcccgccgggaatggtga ttaccgacgaaaacggcaagaaaaagcagtcttacttccatgatttcttt aactatgccggaatccatcgcagcgtaatgctctacaccacgccgaacac ctggggtggacgatatcaccgtggtgacgcatgtcgcgcaagactgtaacc acgcgtctgttgactggcaggtggtggccaatggtgatgtcagcgttgaa ctgcgtgatgcggatcaacaggtggttgcaactggacaaggcactagcgg gactttgcaagtggtgaatccgcacctctggcaacccgggtgaaggttatc tctatgaactgtgcgtcacagccaaaagccagacagagtgtgatatctac ccgcttcgcgtcggcatccggtcagtggcagtgaagggcgaacagttcct gattaaccacaaaccgttctactttactggctttggtcgtcatgaagatg cggacttacgtggcaaaggattcgataacgtgctgatggtgcacgaccac gcattaatggactggattggggccaactcctaccgtacctcgcattaccc ttacgctgaagagatgctcgactgggcagatgaacatggcatcgtggtga ttgatgaaactgctgctgtcggctttaacctctctttaggcattggtttc gaagcgggcaacaagccgaaagaactgtacagcgaagaggcagtcaacgg ggaaactcagcaagcgcacttacaggcgattaaagagctgatagcgcgtg acaaaaaccacccaagcgtggtgatgtggagtattgccaacgaaccggat acccgtccgcaagtgcacgggaatatttcgccactggcggaagcaacgcg taaactcgacccgacgcgtccgatcacctgcgtcaatgtaatgttctgcg acgctcacaccgataccatcagcgatctctttgatgtgctgtgcctgaac cgttattacggatggtatgtccaaagcggcgatttggaaacggcagagaa ggtactggaaaaagaacttctggcctggcaggagaaactgcatcagccga ttatcatcaccgaatacggcgtggatacgttagccgggctgcactcaatg tacaccgacatgtggagtgaagagtatcagtgtgcatggctggatatgta tcaccgcgtctttgatcgcgtcagcgccgtcgtcggtgaacaggtatgga atttcgccgattttgcgacctcgcaaggcatattgcgcgttggcggtaac aagaaagggatcttcactcgcgaccgcaaaccgaagtcggcggcttttct gctgcaaaaacgctggactggcatgaacttcggtgaaaaaccgcagcagg gaggcaaacaagctagccaccaccaccaccaccacgtgtga

GUS1391Z

SEQ ID NO:34

MVDLRVNRRLVRPVEREIKKLDGLWAFSLDRENCGIDQRWWESALQESRA

IAVPGSFNDQFADADIRNYAGNVWYQREVFIPKGWAGQRIVLRFDAVTHY

```
GKVWVNNQEVMEHQGGYTPFEADVTPYVIAGKSVRITVCVNNELNWQTIP

PGMVITDENGKKKQSYFHDFFNYAGIHRSVMLYTTPNTWVDDITVVTHVA

QDCNHASVDWQVVANGDVSVELRDADQQVVATGQGTSGTLQVVNPHLWQP

GEGYLYELCVTAKSQTECDIYPLRVGIRSVAVKGEQFLINHKPFYFTGFG

RHEDADLRGKGFDNVLMVHDHALMDWIGANSYRTSHYPYAEEMLDWADEH

GIVVIDETAAVGFNLSLGIGFEAGNKPKELYSEEAVNGETQQAHLQAIKE

LIARDKNHPSVVMWSIANEPDTRPQVHGNISPLAEATRKLDPTRPITCVN

VMFCDAHTDTISDLFDVLCLNRYYGWYVQSGDLETAEKVLEKELLAWQEK

LHQPIIITEYGVDTLAGLHSMYTDMWSEEYQCAWLDMYHRVFDRVSAVVG

EQVWNFADFATSQGILRVGGNKKGIFTRDRKPKSAAFLLQKRWTGMNFGE

KPQQGGKQASHHHHHV

Salmon calcitonin BAC57417
Protein sequence:
                                               SEQ ID NO:35
KCSNLSTCVLGKLSQELHKLQTYPRTNTGSGTPG DNA sequence:
                                               SEQ ID NO:36
aagtgctccaacctctctacctgcgttcttggtaagctctctcaggagct tcacaagctccagacttaccctagaaccaacactggttccggtaccoctg gt
``` hEGF—Construction based in the AAF85790 without the signal peptide

```
Protein sequence:
                                               SEQ ID NO:37
NSDSECPLSH DGYCLHDGVC MYIEALDKYA CNCVVGYIGE

RCQYRDLKWW ELR

DNA sequence:
                                               SEQ ID NO:38
aactctgattcagaatgcccactcagtcacgacggatattgtcttcacga tggggtatgcatgtacatcgaggccttggacaagtacgcatgtaattgtg tagtgggatacattggtgaacgctgtcagtatcgagacttgaaatggtgg gagcttaggtga
``` hGH—Construction based in the P01241 without the signal peptide

```
Protein sequence:
                                               SEQ ID NO:39
FPTIPLSRLFDNAMLRAHRLHQLAFDTYQEFEEAYIPKEQKYSFLQNPQT

SLCFSESIPTPSNREETQQKSNLELLRISLLLIQSWLEPVQFLRSVFANS

LVYGASDSNVYDLLKDLEEGIQTLMGRLEDGSPRTGQIFKQTYSKFDTNS

HNDDALLKNYGLLYCFRKDMDKVETFLRIVQCRSVEGSCGF

DNA sequence:
                                               SEQ ID NO:40
ttcccaaccattcccttatccaggcttttgacaacgctatgctccgcgc ccatcgtctgcaccagctggcctttgacacctaccaggagtttgaagaag cctatatcccaaaggaacagaagtattcattcctgcagaaccccagacc tccctctgtttctcagagtctattccgacaccctccaacagggaggaaac acaacagaaatccaacctagagctgctccgcatctccctgctgctcatcc agtcgtggctggagcccgtgcagttcctcaggagtgtcttcgccaacagc ctggtgtacggcgcctctgacagcaacgtctatgacctcctaaaggacct agaggaaggcatccaaacgctgatggggaggctggaagatggcagcccc ggactgggcagatcttcaagcagacctacagcaagttcgacacaaactca cacaacgatgacgcactactcaagaactacgggctgctctactgcttcag gaaggacatggacaaggtcgagacattcctgcgcatcgtgcagtgccgct ctgtggagggcagctgtggcttctga
```

In another embodiment, the recombinant fusion protein further comprises in addition to the sequences of the PBIS and product of interest, a spacer amino acid sequence. The spacer amino acid sequence can be an amino acid sequence cleavable by enzymatic or chemical means or not cleavable. By "not cleavable" it is meant that cleavage of the spacer does not occur without destruction of some or all of the biologically active polypeptide.

In a particular embodiment, the spacer amino acid sequence is placed between the PBIS and biologically active polypeptide. An illustrative amino acid sequence is cleavable by a protease such as an enterokinase, Arg-C endoprotease, Glu-C endoprotease, Lys-C endoprotease, Factor Xa, SUMO proteases [Tauseef et al., 2005 *Protein Expr. Purif.* 2005 September 43(1):1-9] and the like. Alternatively, the spacer amino acid sequence corresponds to an auto-cleavable sequence such as the FMDV viral auto-processing 2A sequence, protein introns (inteins) such as the Ssp DNAb intein and the like as are commercially available from New England Biolabs and others. The use of an intein linker sequence is preferred as such sequences can be selectively induced to cause protein splicing and thereby eliminate themselves from an expressed, recovered, protein. Inteins are particularly interesting since they do not require large protein enzymes to reach their target site in order to cleave the PBIS from the protein of interest. This property may be particularly useful for direct isolation of proteins of interest from intact RPBLAs. Alternatively, an amino acid sequence is encoded that is specifically cleavable by a chemical reagent, such as, for example, cyanogen bromide that cleaves at methionine residues.

In a further embodiment, the nucleic acid sequence used for transformation or transduction purposes is as disclosed according to co-assigned patent application WO 2004003207, with or without the nucleic acid sequence coding for the cleavable amino acid sequence.

Methods of Preparation

In a preferred embodiment, the fusion proteins are prepared according to a method that comprises transforming a eukaryotic host cell system such as an animal, animal cell culture, plant or plant cell culture, fungus culture, insect cell culture or algae culture with a nucleic acid (DNA or RNA) sequence comprising (i) a first nucleic acid coding for a PBIS that is operatively linked in frame to (ii) a second nucleic acid sequence comprising the nucleotide sequence coding for a polypeptide product of interest that is biologically active; that is, the nucleic acid sequence that encodes the PBIS is chemically bonded (peptide bonded) to the sequence that encodes the polypeptide of interest such that both polypeptides are expressed from their proper reading frames and the protein of interest is biologically active. It is also contemplated that appropriate regulatory sequences be present on either side of the nucleic acid sequences that encode the PBIS and protein of interest as is discussed hereinafter. Such control sequences are well known and are present in commercially available vectors. The use of indirect means of introducing DNA, such as via viral transduction or infection, is also contemplated, and shall be used interchangeably with direct DNA delivery methods such as transfection.

The transformed host cell or entity is maintained for a time period and under culture conditions suitable for expression of the fusion protein and assembly of the expressed fusion protein into RPBLAs. Upon expression, the resulting fusion protein accumulates in the transformed host-system as high density RPBLAs. The fusion protein can then be recovered from the host cells or the host cells containing the fusion protein can be used as desired, as for an animal food containing an added nutrient or supplement. The fusion protein can be isolated as part of the RPBLAs or free from the RPBLAs.

Culture conditions suitable for expression of the fusion protein are typically different for each type of host entity or host cell. However, those conditions are known by skilled workers and are readily determined. Similarly, the duration of maintenance can differ with the host cells and with the amount of fusion protein desired to be prepared. Again, those conditions are well known and can readily be determined in specific situations. Additionally, specific culture conditions can be obtained from the citations herein.

In one embodiment, the 3' end of the first nucleic acid sequence (i) is linked (bonded) to the 5' end of the second nucleic acid sequence (ii). In other embodiment, the 5' end of the first nucleic acid sequence (i) is linked (bonded) to the 3' end of the second nucleic acid sequence (ii). In another embodiment, the PBIS comprises a storage protein or a modified storage protein, a fragment or a modified fragment thereof.

In another particular embodiment, a fusion protein is prepared according to a method that comprises transforming the host cell system such as an animal, animal cell culture, plant, plant cell culture, fungus or algae with a nucleic acid sequence comprising, in addition to the nucleic acid sequences (i) and (ii) previously mentioned, an in frame nucleic acid sequence (iii) that codes for a spacer amino acid sequence. The spacer amino acid sequence can be an amino acid sequence cleavable by enzymatic or chemical means or not cleavable, as noted before. In one particular embodiment, the nucleic acid sequence (iii) is placed between said nucleic acid sequences (i) and (ii), e.g., the 3' end of the third nucleic acid sequence (iii) is linked to the 5' end of the second nucleic acid sequence (ii). In another embodiment, the 5' end of the third nucleic acid sequence (iii) is linked to the 3' end of the second nucleic acid sequence (ii).

A nucleic acid sequence (segment) that encodes a previously described fusion protein molecule or a complement of that coding sequence is also contemplated herein. Such a nucleic acid segment is present in isolated and purified form in some preferred embodiments.

In living organisms, the amino acid residue sequence of a protein or polypeptide is directly related via the genetic code to the deoxyribonucleic acid (DNA) sequence of the gene that codes for the protein. Thus, through the well-known degeneracy of the genetic code additional DNAs and corresponding RNA sequences (nucleic acids) can be prepared as desired that encode the same fusion protein amino acid residue sequences, but are sufficiently different from a before-discussed gene sequence that the two sequences do not hybridize at high stringency, but do hybridize at moderate stringency.

High stringency conditions can be defined as comprising hybridization at a temperature of about 500-55° C. in 6×SSC and a final wash at a temperature of 68° C. in 1-3×SSC. Moderate stringency conditions comprise hybridization at a temperature of about 50° C. to about 65° C. in 0.2 to 0.3 M NaCl, followed by washing at about 50° C. to about 55° C. in 0.2×SSC, 0.1% SDS (sodium dodecyl sulfate).

A nucleic sequence (DNA sequence or an RNA sequence) that (1) itself encodes, or its complement encodes, a fusion protein containing a protein body-inducing sequence (PBIS) and a polypeptide of interest is also contemplated herein. As is well-known, a nucleic acid sequence such as a contemplated nucleic acid sequence is expressed when operatively linked to an appropriate promoter in an appropriate expression system as discussed elsewhere herein. This nucleic acid sequence can be delivered directly or indirectly (via an appropriate vector organism such as a virus or bacterium) to the host eukaryotic cell, and can be integrated stably into the host nuclear or organellar genome, or transiently expressed without genome integration.

Different hosts often have preferences for a particular codon to be used for encoding a particular amino acid residue. Such codon preferences are well known and a DNA sequence encoding a desired fusion protein sequence can be altered, using in vitro mutagenesis for example, so that host-preferred codons are utilized for a particular host in which the fusion protein is to be expressed.

A recombinant nucleic acid molecule such as a DNA molecule, comprising a gene vector or construct containing one or more regulatory sequences (control elements) such as a promoter suitable for driving the expression of the gene in a compatible eukaryotic host cell organism operatively linked to an exogenous nucleic acid segment (e.g., a DNA segment or sequence) that defines a gene that encodes a contemplated fusion protein, as discussed above, is also contemplated in this invention. More particularly, also contemplated is a recombinant DNA molecule that comprises a gene vector comprising a promoter for driving the expression of the fusion protein in host organism cells operatively linked to a DNA segment that defines a gene encodes a protein body-inducing sequence (PBIS) linked to a polypeptide of interest. That recombinant DNA molecule, upon suitable transfection and expression in a host eukaryotic cell, provides a contemplated fusion protein as RPBLAs.

As is well known in the art, so long as the required nucleic acid, illustratively DNA sequence, is present, (including start and stop signals), additional base pairs can usually be present at either end of the DNA segment and that segment can still be utilized to express the protein. This, of course, presumes the absence in the segment of an operatively linked DNA sequence that represses expression, expresses a further product that consumes the fusion protein desired to be expressed, expresses a product that consumes a wanted reaction product produced by that desired fusion protein, or otherwise interferes with expression of the gene of the DNA segment.

Thus, so long as the DNA segment is free of such interfering DNA sequences, a DNA segment of the invention can be about 500 to about 15,000 base pairs in length. The maximum size of a recombinant DNA molecule, particularly an expression vector, is governed mostly by convenience and the vector size that can be accommodated by a host cell, once all of the minimal DNA sequences required for replication and expression, when desired, are present. Minimal vector sizes are well known. Such long DNA segments are not preferred, but can be used.

A DNA segment that encodes a before-described fusion protein can be synthesized by chemical techniques, for example, the phosphotriester method of Matteucci et al., 1981 *J. Am. Chem. Soc.,* 103:3185. Of course, by chemically synthesizing the coding sequence, any desired modifications can be made simply by substituting the appropriate bases for those encoding the native amino acid residue sequence. However, DNA segments including sequences specifically discussed herein are preferred.

DNA segments containing a gene encoding the fusion protein are preferably obtained from recombinant DNA molecules (plasmid vectors) containing that gene. A vector that directs the expression of a fusion protein gene in a host cell is referred to herein as an "expression vector".

An expression vector contains expression control elements including the promoter. The fusion protein-coding gene is operatively linked to the expression vector to permit the promoter sequence to direct RNA polymerase binding and expression of the fusion protein-encoding gene. Useful in expressing the polypeptide coding gene are promoters that are inducible, viral, synthetic, constitutive as described by Paszkowski et al., 1989 *EMBO J.*, 3:2719 and Odell et al., 1985 *Nature*, 313:810, as well as temporally regulated, spatially regulated, and spatiotemporally regulated as given in Chua et al., 1989 *Science*, 244:174-181.

Expression vectors compatible with eukaryotic cells, such as those compatible with cells of mammals, algae or insects and the like, are contemplated herein. Such expression vectors can also be used to form the recombinant DNA molecules of the present invention. Eukaryotic cell expression vectors are well known in the art and are available from several commercial sources. Normally, such vectors contain one or more convenient restriction sites for insertion of the desired DNA segment and promoter sequences. Optionally, such vectors contain a selectable marker specific for use in eukaryotic cells.

Production of a fusion protein by recombinant DNA expression in mammalian cells is illustrated hereinafter using a recombinant DNA vector that expresses the fusion protein gene in Chinese hamster ovary (CHO) host cells, Cos1 monkey host and human 293T host cells. This is accomplished using procedures that are well known in the art and are described in more detail in Sambrook et al., *Molecular Cloning: A Laboratory Manual*, 2$^{nd}$ ed., Cold Spring Harbor Laboratories (1989).

An insect cell system can also be used to express a contemplated fusion protein. For example, in one such system *Autographa californica* nuclear polyhedrosis virus (AcNPV) or baculovirus is used as a vector to express foreign genes in *Spodoptera frugiperda* cells or in *Trichoplusia* larvae. The sequences encoding a fusion protein can be cloned into a non-essential region of the virus, such as the polyhedrin gene, and placed under control of the polyhedrin promoter. Successful insertion of a fusion protein sequence renders the polyhedrin gene inactive and produces recombinant virus lacking coat protein. The recombinant viruses can then be used to infect, for example, *S. Frugiperda* cells or *Trichoplusia* larvae in which the fusion protein can be expressed, for example as described in Engelhard et al. (1994) *Proc. Natl. Acad. Sci., USA*, 91:3224-3227; and V. Luckow, "Insect Cell Expression Technology", pages 183-218, in *Protein Engineering: Principles and Practice*, J. L. Cleland et al. eds., Wiley-Liss, Inc, 1996). Heterologous genes placed under the control of the polyhedrin promoter of the *Autographa californica* nuclear polyhedrosis virus (AcNPV) are often expressed at high levels during the late stages of infection.

Recombinant baculoviruses containing the fusion protein gene are constructed using the baculovirus shuttle vector system (Luckow et al., 1993 *J. Virol.*, 67:4566-4579], sold commercially as the Bac-To-Bac™ baculovirus expression system (Life Technologies). Stocks of recombinant viruses are prepared and expression of the recombinant protein is monitored by standard protocols (O'Reilly et al., *Baculovirus Expression Vectors: A Laboratory Manual*, W.H. Freeman and Company, New York, 1992; and King et al., *The Baculovirus Expression System: A Laboratory Guide*, Chapman & Hall, London, 1992). Use of baculovirus or other delivery vectors in mammalian cells, such as the 'BacMam' system described by T. Kost and coworkers (see, for example Merrihew et al., 2004 *Methods Mol. Biol.* 246:355-365), or other such systems as are known to those skilled in the art are also contemplated in the instant invention.

The choice of which expression vector and ultimately to which promoter a fusion protein-encoding gene is operatively linked depends directly on the functional properties desired, e.g., the location and timing of protein expression, and the host cell to be transformed. These are well known limitations inherent in the art of constructing recombinant DNA molecules. However, a vector useful in practicing the present invention can direct the replication, and preferably also the expression (for an expression vector) of the fusion protein gene included in the DNA segment to which it is operatively linked.

Typical vectors useful for expression of genes in cells from higher plants and mammals are well known in the art and include plant vectors derived from the tumor-inducing (Ti) plasmid of *Agrobacterium tumefaciens* described by Rogers et al. (1987) *Meth. in Enzymol.*, 153:253-277 and mammalian expression vectors pKSV-10, above, and pCI-neo (Promega Corp., #E1841, Madison, Wis.). However, several other expression vector systems are known to function in plants including pCaMVCN transfer control vector described by Fromm et al. (1985) *Proc. Natl. Acad. Sci. USA*, 82:58-24. Plasmid pCaMVCN (available from Pharmacia, Piscataway, N.J.) includes the cauliflower mosaic virus CaMV 35S promoter.

The above plant expression systems typically provide systemic or constitutive expression of an inserted transgene. Systemic expression can be useful where most or all of a plant is used as the source of RPBLAs and their fusion proteins. However, it can be more efficacious to express RPBLAs and their fusion protein contents in a plant storage organ such as a root, seed or fruit from which the particles can be more readily isolated or ingested.

One manner of achieving storage organ expression is to use a promoter that expresses its controlled gene in one or more preselected or predetermined non-photosynthetic plant organs. Expression in one or more preselected storage organs with little or no expression in other organs such as roots, seed or fruit versus leaves or stems is referred to herein as enhanced or preferential expression. An exemplary promoter that directs expression in one or more preselected organs as compared to another organ at a ratio of at least 5:1 is defined herein as an organ-enhanced promoter. Expression in substantially only one storage organ and substantially no expression in other storage organs is referred to as organ-specific expression; i.e., a ratio of expression products in a storage organ relative to another of about 100:1 or greater indicates organ specificity. Storage organ-specific promoters are thus members of the class of storage organ-enhanced promoters.

Exemplary plant storage organs include the roots of carrots, taro or manioc, potato tubers, and the meat of fruit such as red guava, passion fruit, mango, papaya, tomato, avocado, cherry, tangerine, mandarin, palm, melons such cantaloupe and watermelons and other fleshy fruits such as squash, cucumbers, mangos, apricots, peaches, as well as the seeds of maize (corn), soybeans, rice, oil seed rape and the like.

The CaMV 35S promoter is normally deemed to be a constitutive promoter. However, research has shown that a 21-bp region of the CaMV 35S promoter, when operatively linked into another, heterologous usual green tissue promoter, the rbcS-3A promoter, can cause the resulting chimeric promoter to become a root-enhanced promoter. That 21-bp sequence is disclosed in U.S. Pat. No. 5,023,179. The chimeric rbcS-3A promoter containing the 21-bp insert of U.S. Pat. No. 5,023,179 is a useful root-enhanced promoter herein.

A similar root-enhanced promoter, which includes the above 21-bp segment, is the −90 to +8 region of the CAMV 35S promoter itself. U.S. Pat. No. 5,110,732 discloses that that truncated CaMV 35S promoter provides enhanced expression in roots and the radicle of seed, a tissue destined to become a root. That promoter is also useful herein.

Another useful root-enhanced promoter is the −1616 to −1 promoter of the oil seed rape (Brassica napus L.) gene disclosed in PCT/GB92/00416 (WO 91/13922 published Sep. 19, 1991). E. coli DH5-alpha harboring plasmid pRlambdaS4 and bacteriophage lambda.beta.1 that contain this promoter were deposited at the National Collection of Industrial and Marine Bacteria, Aberdeen, GB on Mar. 8, 1990 and have accession numbers NCIMB40265 and NCIMB40266. A useful portion of this promoter can be obtained as a 1.0 kb fragment by cleavage of the plasmid with HaeIII.

A preferred root-enhanced promoter is the mannopine synthase (mas) promoter present in plasmid pKan2 described by DiRita and Gelvin (1987) Mol. Gen. Genet, 207:233-241. This promoter is removable from its plasmid pKan2 as a XbaI-XbaII fragment.

The preferred mannopine synthase root-enhanced promoter is comprised of the core mannopine synthase (mas) promoter region up to position −138 and the mannopine synthase activator from −318 to −213, and is collectively referred to as AmasPmas. This promoter has been found to increase production in tobacco roots about 10- to about 100-fold compared to leaf expression levels.

Another root specific promoter is the about 500 bp 5' flanking sequence accompanying the hydroxyproline-rich glycopeprotein gene, HRGPnt3, expressed during lateral root initiation and reported by Keller et al. (1989) Genes Dev., 3:1639-1646. Another preferred root-specific promoter is present in the about −636 to −1 5' flanking region of the tobacco root-specific gene TORBF reported by Yamamoto et al. (1991) Plant Cell, 3:371-381. The cis-acting elements regulating expression are more specifically located by those authors in the region from about −636 to about −299 5' from the transcription initiation site. Yamamoto et al. reported steady state mRNA production from the TORBF gene in roots, but not in leaves, shoot meristems or stems.

Still another useful storage organ-specific promoter are the 5' and 3' flanking regions of the fruit-ripening gene E8 of the tomato, Lycopersicon esculentum. These regions and their cDNA sequences are illustrated and discussed in Deikman et al. (1988) EMBO J., 7(11):3315-3320 and (1992) Plant Physiol., 100:2013-2017.

Three regions are located in the 2181 bp of the 5' flanking sequence of the gene and a 522 bp sequence 31 to the poly (A) addition site appeared to control expression of the E8 gene. One region from −2181 to −1088 is required for activation of E8 gene transcription in unripe fruit by ethylene and also contributes to transcription during ripening. Two further regions, −1088 to −863 and −409 to −263, are unable to confer ethylene responsiveness in unripe fruit but are sufficient for E8 gene expression during ripening.

The maize sucrose synthase-1 (Sh) promoter that in corn expresses its controlled enzyme at high levels in endosperm, at much reduced levels in roots and not in green tissues or pollen has been reported to express a chimeric reporter gene, β-glucuronidase (GUS), specifically in tobacco phloem cells that are abundant in stems and roots. Yang et al. (1990) Proc. Natl. Acad. Sci., U.S.A., 87:4144-4148. This promoter is thus useful for plant organs such as fleshy fruits like melons, e.g. cantaloupe, or seeds that contain endosperm and for roots that have high levels of phloem cells.

Another exemplary tissue-specific promoter is the lectin promoter, which is specific for seed tissue. The lectin protein in soybean seeds is encoded by a single gene (Le1) that is only expressed during seed maturation and accounts for about 2 to about 5 percent of total seed mRNA. The lectin gene and seed-specific promoter have been fully characterized and used to direct seed specific expression in transgenic tobacco plants. See, e.g., Vodkin et al. (1983) Cell, 34:1023 and Lindstrom et al. (1990) Developmental Genetics, 11:160.

A particularly preferred tuber-specific expression promoter is the 5' flanking region of the potato patatin gene. Use of this promoter is described in Twell et al. (1987) Plant Mol. Biol., 9:365-375. This promoter is present in an about 406 bp fragment of bacteriophage LPOTI. The LPOTI promoter has regions of over 90 percent homology with four other patatin promoters and about 95 percent homology over all 400 bases with patatin promoter PGT5. Each of these promoters is useful herein. See, also, Wenzler et al. (1989) Plant Mol. Biol., 12:41-50.

Still further higher plant organ-enhanced and organ-specific promoter are disclosed in Benfey et al. (1988) Science, 244:174-181.

Each of the promoter sequences utilized is substantially unaffected by the amount of RPBLAs in the cell. As used herein, the term "substantially unaffected" means that the promoter is not responsive to direct feedback control (inhibition) by the RPBLAs accumulated in transformed cells or transgenic plant.

Transfection of plant cells using Agrobacterium tumefaciens is typically best carried out on dicotyledonous plants. Monocots are usually most readily transformed by so-called direct gene transfer of protoplasts. Direct gene transfer is usually carried out by electroportation, by polyethyleneglycol-mediated transfer or bombardment of cells by microprojectiles carrying the needed DNA. These methods of transfection are well-known in the art and need not be further discussed herein. Methods of regenerating whole plants from transfected cells and protoplasts are also well-known, as are techniques for obtaining a desired protein from plant tissues. See, also, U.S. Pat. Nos. 5,618,988 and 5,679,880 and the citations therein.

A transgenic plant formed using Agrobacterium transformation, electroportation or other methods typically contains a single gene on one chromosome. Such transgenic plants can be referred to as being heterozygous for the added gene. However, inasmuch as use of the word "heterozygous" usually implies the presence of a complementary gene at the same locus of the second chromosome of a pair of chromosomes, and there is no such gene in a plant containing one added gene as here, it is believed that a more accurate name for such a plant is an independent segregant, because the added, exogenous chimer molecule-encoding gene segregates independently during mitosis and meiosis. A transgenic plant containing an organ-enhanced promoter driving a single structural gene that encodes a contemplated HBc chimeric molecule; i.e., an independent segregant, is a preferred transgenic plant.

More preferred is a transgenic plant that is homozygous for the added structural gene; i.e., a transgenic plant that contains two added genes, one gene at the same locus on each chromosome of a chromosome pair. A homozygous transgenic plant can be obtained by sexually mating (selfing) an independent segregant transgenic plant that contains a single added gene, germinating some of the seed produced and analyzing the resulting plants produced for enhanced chimer particle accumulation relative to a control (native, non-transgenic) or an independent segregant transgenic plant. A homozygous transgenic plant exhibits enhanced chimer particle accumulation as compared to both a native, non-transgenic plant and an independent segregant transgenic plant.

It is to be understood that two different transgenic plants can also be mated to produce offspring that contain two independently segregating added, exogenous (heterologous) genes. Selfing of appropriate progeny can produce plants that are homozygous for both added, exogenous genes that encode a chimeric HBc molecule. Back-crossing to a parental plant and out-crossing with a non-transgenic plant are also contemplated.

A transgenic plant of this invention thus has a heterologous structural gene that encodes a contemplated chimeric HBc molecule. A preferred transgenic plant is an independent segregant for the added heterologous chimeric HBc structural gene and can transmit that gene to its progeny. A more preferred transgenic plant is homozygous for the heterologous gene, and transmits that gene to all of its offspring on sexual mating.

The expressed RPBLAs and their fusion proteins can be obtained from the expressing host cells by usual means utilized in biochemical or biological recovery. Because the RPBLAs are dense relative to the other proteins present in the host cells, the RPBLAs are particularly amenable to being collected by centrifugation of a cellular homogenate.

Thus, regions of different density are formed in the homogenate to provide a region that contains a relatively enhanced concentration of the RPBLAs and a region that contains a relatively depleted concentration of the RPBLAs. The RPBLAs-depleted region is separated from the region of relatively enhanced concentration of RPBLAs, thereby purifying said fusion protein. The region of relatively enhanced concentration of RPBLAs can thereafter be collected or can be treated with one or more reagents or subjected to one or more procedures prior to isolation of the RPBLAs or the fusion protein therein. In some embodiments, the collected RPBLAs are used as is, without the need to isolate the fusion protein, as where the RPBLAs are used as an oral vaccine. The fusion protein containing the biologically active polypeptide can be obtained from the collected RPBLAs by dissolution of the surrounding membrane in an aqueous buffer containing a detergent and a reducing agent as discussed previously. Illustrative reducing agents include 2-mercaptoethanol, thioglycolic acid and thioglycolate salts, dithiothreitol (DTT), sulfite or bisulfite ions, followed by usual protein isolation methods. Sodium dodecyl sulfate (SDS) is the preferred detergent, although other ionic (deoxycholate, 'N-Lauroylsarcosine, and the like), non-ionic (Tween® 20, Nonidet® P-40, octyl glucoside and the like) and zwitterionic (CHAPS, Zwittergent™ 3-X serie and the like) surfactants can be used. A minimal amount of surfactant that dissolves or disperses the fusion protein is utilized.

Vaccines and Inocula

In yet another embodiment of the invention, RPBLAs are used as the immunogen of an inoculum or vaccine in a human patient or other suitable animal host such as a chimpanzee, mouse, rat, horse, sheep, bovine, dog, cat or the like. An inoculum can induce a B cell or T cell response (stimulation) such as production of antibodies that immunoreact with the immunogenic epitope or antigenic determinant, or T cell activation to such an epitope, whereas a vaccine provides protection against the entity from which the immunogen has been derived via one or both of a B cell or T cell response.

The RPBLAs of a contemplated vaccine or inoculum appear to act upon antigen presenting cells (APCs) such as dendritic cells and monocytes/macrophages that engulf the RPBLAs and process their contents. In acting upon those cell types, the RPBLAs improve the antigen delivery to antigen-presenting cells. Those RPBLAs also improve the antigen processing and presentation to antigen-presenting cells.

Thus, the invention also contemplates a vaccine or inoculum that comprises an immunogenic effective amount of recombinant protein body-like assemblies (RPBLAs) that are dissolved or dispersed in a pharmaceutically acceptable diluent. The RPBLAs contain a recombinant fusion protein recombinant fusion protein that itself contains two sequences linked together in which one sequence is a protein body-inducing sequence (PBIS) and the other is a biologically active polypeptide to which an immunological response is to be induced by said vaccine or inoculum.

T cell activation can be measured by a variety of techniques. In usual practice, a host animal is inoculated with a contemplated RPBLA vaccine or inoculum, and peripheral mononuclear blood cells (PMBC) are thereafter collected. Those PMBC are then cultured in vitro in the presence of the biologically active polypeptide (T cell immunogen) for a period of about three to five days. The cultured PMBC are then assayed for proliferation or secretion of a cytokine such as IL-2, GM-CSF of IFN-γ. Assays for T cell activation are well known in the art. See, for example, U.S. Pat. No. 5,478,726 and the art cited therein.

Using antibody formation as exemplary, a contemplated inoculum or vaccine comprises an immunogenically effective amount of RPBLAs that are dissolved or dispersed in a pharmaceutically acceptable diluent composition that typically also contains water. When administered to a host animal in which an immunological response to the biologically active polypeptide is to be induced by the vaccine or inoculum such as a host animal in need of immunization or in which antibodies are desired to be induced such as a mammal (e.g., a mouse, dog, goat, sheep, horse, bovine, monkey, ape, or human) or bird (e.g., a chicken, turkey, duck or goose), an inoculum induces antibodies that immunoreact with one or more antigenic determinants of the target biologically active polypeptide.

The amount of RPBLA immunogen utilized in each immunization is referred to as an immunogenically effective amount and can vary widely, depending inter alia, upon the RPBLA immunogen, patient immunized, and the presence of an adjuvant in the vaccine, as discussed below. Immunogenically effective amounts for a (i) vaccine and an (ii) inoculum provide the (i) protection or (ii) antibody or T cell activity, respectively, discussed hereinbefore.

Vaccines or inocula typically contain a RPBLA immunogen concentration of about 1 microgram to about 1 milligram per inoculation (unit dose), and preferably about 10 micrograms to about 50 micrograms per unit dose. The term "unit dose" as it pertains to a vaccine or inoculum of the present invention refers to physically discrete units suitable as unitary dosages for animals, each unit containing a predetermined quantity of active material calculated to individually or collectively produce the desired immunogenic effect in association with the required diluent; i.e., carrier, or vehicle.

Vaccines or inocula are typically prepared from a recovered RPBLA immunogen by dispersing the immunogen, in particulate form, in a physiologically tolerable (acceptable)

diluent vehicle such as water, saline, phosphate-buffered saline (PBS), acetate-buffered saline (ABS), Ringer's solution, or the like to form an aqueous composition. The diluent vehicle can also include oleaginous materials such as peanut oil, squalane, or squalene as is discussed hereinafter.

The preparation of inocula and vaccines that contain proteinaceous materials as active ingredients is also well understood in the art. Typically, such inocula or vaccines are prepared as parenterals, either as liquid solutions or suspensions; solid forms suitable for solution in, or suspension in, liquid prior to injection can also be prepared. The preparation can also be emulsified, which is particularly preferred.

The immunogenically active RPBLAs are often mixed with excipients that are pharmaceutically acceptable and compatible with the active ingredient. Suitable excipients are, for example, water, saline, dextrose, glycerol, ethanol, or the like and combinations thereof. In addition, if desired, an inoculum or vaccine can contain minor amounts of auxiliary substances such as wetting or emulsifying agents, pH buffering agents that enhance the immunogenic effectiveness of the composition.

The word "antigen" has been used historically to designate an entity that is bound by an antibody or receptor, and also to designate the entity that induces the production of the antibody. More current usage limits the meaning of antigen to that entity bound by an antibody or receptor, whereas the word "immunogen" is used for the entity that induces antibody production or binds to the receptor. Where an entity discussed herein is both immunogenic and antigenic, reference to it as either an immunogen or antigen is typically made according to its intended utility.

"Antigenic determinant" refers to the actual structural portion of the antigen that is immunologically bound by an antibody combining site or T-cell receptor. The term is also used interchangeably with "epitope".

As used herein, the term "fusion protein" designates a polypeptide that contains at least two amino acid residue sequences not normally found linked together in nature that are operatively linked together end-to-end (head-to-tail) by a peptide bond between their respective carboxy- and amino-terminal amino acid residues. The fusion proteins of the present invention are chimers of a protein body-inducing sequence (PBIS) linked to a second sequence that is a biologically active polypeptide product (e.g., peptide or protein) of interest (target).

Without further elaboration, it is believed that one skilled in the art can, using the preceding description and the detailed examples below, utilize the present invention to its fullest extent. The following preferred specific embodiments are, therefore, to be construed as merely illustrative, and not limiting of the remainder of the disclosure in any way whatsoever.

Example 1

Accumulation of RX3-ECFP Derived Fusion Proteins in Dense Fractions of Transfected Mammal Cells The polynucleotide sequence coding for the N-terminal gamma-zein coding sequence RX3 (WO2004003207) was fused directly, or through a linker consisting of five glycines, to the 5' end of the sequence encoding ECFP, a cyan fluorescent variant of GFP. Those constructs (FIG. 1A) that code for the fusion proteins RX3-ECFP or RX3-Gx5-ECFP were introduced in cultured mammalian CHO cells by the Lipofectamine-based transfection method (Invitrogen). CHO cells transfected with plasmid pECFP-N1 (Clontech) containing the gene sequence of a non-targeted (cytosolic) ECFP were used as controls.

Transfected mammalian cell extracts were loaded on density step gradients and centrifuged. The accumulation of recombinant proteins in the different fractions was analyzed by immunoblot. The results shown in FIG. 2A indicate that RX3-ECFP and RX3-Gx5-ECFP sedimented in fractions F42, F56 and P corresponding to dense RPBLAs, (FIG. 2A, lanes 3-5). This result demonstrates that the fusion proteins are able to assemble and induce RPBLA formation. Some fusion protein was also detected in the supernatant fraction (FIG. 2A, lane 1), probably representing fusion proteins from the RPBLAs solubilized partially during the extraction process, or newly-synthesized fusion proteins that had not yet assembled.

In contrast, when mammalian cell extract transfected with the control plasmid pECFP-N1 was loaded on the same density step gradients, the ECFP protein was observed exclusively in the supernatant. No traces of ECFP were detected in the dense fractions indicating that the ECFP by itself is not able to aggregate and form PB-like structures.

Example 2

Accumulation of Active ECFP Fused to PBIS Domains in RPBLAs of Transfected Mammal Cells To determine if the fusion proteins RX3-ECFP, RX3-Gx5-ECFP and 22aZ-ECFP are active inside the RPBLAs, confocal microscopic analysis was performed to visualize target protein fluorescence in transfected CHO cells (FIG. 1A). Cyan fluorescence was imaged by excitation at 458 nm with an argon ion laser with an emission window set at 470-530 nm. As shown in FIG. 3, the corresponding fusion proteins, RX3-ECFP (FIG. 3A) and RX3-Gx5-ECFP (FIG. 3B) and 22aZ-ECFP (FIG. 3D), were detected in proximity to the ER, indicating that the gamma-zein and the alpha-zein signal peptides are functional in mammalian cells where they mediates the translocation of the fusion protein into the ER.

In addition, the fusion proteins surprisingly also accumulated preferentially into large and dense spherical structures that strongly resembled both authentic PBs of cereal seed and RPBLAs in heterologous systems visualized by immunodetection. The intense fluorescence emission observed in these structures indicates that the fusion proteins remain properly folded, and therefore active, in spite of being tightly packaged inside the RPBLAs. It is also important to note that RX3 domains, as well as other protein body inducing sequences (PBIS) responsible for the formation of PBs and PB-like structures contain multiple cysteine residues. Although it might be predicted that such cysteines could form disulfide bonds with target protein cysteines and hence interfere with the proper folding of the target proteins this was not observed to be the case. Both active target protein (ECFP fluorescence) and functional PBIS (formation of RPBLAs) were observed.

As a control, the construct pECFP-N1 was used to transfect CHO cells. The expression of a cytosolic ECFP showed a homogeneous fluorescence pattern all along the cell, including the nucleus (FIG. 3C).

Example 3

Subcellular Localization of Other Fluorescent Proteins Fused to RX3 in CHO Cells The sub-cellular localization of RX3-DsRED and RX3-GFP fusion proteins in transiently transfected CHO cells was analyzed by confocal microscopy to analyze whether other fluorescent proteins than ECFP fused to RX3 are properly folded and bioactive inside RPBLAs. It is important to note that DsRED shares no homology to ECFP, which implies a completely different folding mechanism. Fluorescence images from the transfected cells were obtained by using a confocal laser scanning microscope (Leica TCS SP, Heidelberg, Germany) fitted with spectrophotometers for emission band wavelength selection. Green fluorescent images were collected by excitation at 488 nm with an Argon ion laser using an emission window set at 495-535 nm. Red fluorescent images were collected using 543 nm excitation with a HeNe laser and an emission window of 550-600 nm. Optical sections were 0.5 μm thick.

The expression of RX3-GFP (FIG. 3E) and RX3-DsRED (FIG. 3F) fusion proteins in CHO cells produced a large amount of highly fluorescent round-shaped RPBLAs. These results confirm that both fusion proteins are properly folded and active inside the intact RPBLAs.

Example 4

Subcellular Localization of Fluorescent RX3 Fusion Proteins in Plants and Insects In order to analyze whether host cells other than CHO cells can produce RPBLAs containing active fluorescent proteins fused to RX3 domains, tobacco plants were transiently transformed with RX3-GFP by syringe agroinfiltration. The analysis by confocal microscopy of the epidermal cells (FIGS. 4A and 4B) revealed the presence of a large amount of fluorescent RPBLAs. Similar results were obtained when transformed tobacco mesophyll cells were analyzed.

Expression of fully functional DsRED fluorescent protein in RPBLAs was also obtained when *Spodoptera* Sf9 insect cells or insect larvae (*Trichoplusia ni*) were infected with baculovirus carrying expression plasmids coding for the fusion protein RX3-DsRED under control of the insect polyhedrin promoter. As shown in FIG. 4C, infected insect cells accumulated a large number of fluorescent RPBLAs containing active RX3-DsRED fusion protein. These structures were approximately 0.5 micrometers in diameter. Confocal analysis of infected larvae also showed an impressive amount of fluorescent RPBLAs in all tissues analyzed. In FIG. 4D, epidermal cells from infected larvae show RPBLAs containing active RX3-DsRED. Interestingly, DsRED fluorescence was not observed in insect haemolymph, suggesting that the expressed protein remained sequestered entirely within RPBLAs.

Example 5

Activity of RX3-hGH Assembled in RPBLAs in CHO Cells

Studies were undertaken to determine if human growth hormone (hGH) produced in RPBLAs still retained biological activity. Growth hormone was chosen because this molecule contains 2 disulphide bonds that are required for the proper folding of the protein into an active conformation. The RX3 domain also contains cysteine residues involved in disulphide bonds that are essential for the assembly and stabilization of the RPBLAs, which could interfere in the proper folding of the hGH.

The p3.1-RX3-hGH construct was introduced into CHO cells by transient transfection with the lipofectamine protocol (Invitrogen). Four days after transfection the cells were fixed and permeabilized. In order to visualize RPBLAs, the cells were incubated with primary anti-RX3 or anti-hGH antisera followed by a secondary antibody conjugated to Alexa Fluor 488 (Invitrogen). Both RX3 and hGH immunodetection (FIGS. 5A and 5B, respectively) revealed the presence of identical large and densely immunostaining structures of ca. 1-3 um containing the RX3-hGH fusion protein.

In order to verify that the PB-like organelles observed by immunodetection were in fact RBPLAs, CHO cells expressing RX3-hGH were homogenized, and the homogenates loaded on a density step gradient and centrifuged as previously described. The accumulation of RX3-hGH in the different fractions was analyzed by immunoblot. As can be seen, part of the fusion protein was present in the supernatant, representing non-assembled RX3-hGH, but most of the fusion protein was detected in fraction F56 corresponding to dense RPBLAs (FIG. 2B, lanes 2 and 5, respectively).

The isolated F56 fraction was diluted 3-fold in buffer PBP4 (100 mM Tris pH7.5, 50 mM KCl, 5 mM $MgCl_2$, 5 mM EDTA) and centrifuged at 80000×g in a swinging-bucket to recover the RPBLAs in the pellet. The presence of hGH was quantified using an ELISA assay (Active® Human Growth Hormone ELISA-DSL-10-1900; Diagnostic Systems Laboratories, Inc), which was able to detect the hGH even in the presence of the intact RPBLA membrane.

The intact hGH RPBLA sample was analyzed for hormone bioactivity using a commercial assay (Active® Bioactive Human Growth Hormone ELISA—DSL-10-11100; Diagnostic Systems Laboratories, Inc). This bioactivity assay is based on the capacity of properly folded hGH to interact with an hGH binding protein provided by the kit, the interaction being dependent on correct functional conformation of the hGH. The sample gave a positive result (24 ng/ml of bioactive protein), demonstrating that the hGH proteins were correctly folded and presented on the outer surface of the dense RPBLAs. Removal of the membrane surrounding the RPBLAs by washing the preparation with 50 mM Tris pH 8 and 1% Triton X-100 and by sonicating at 50% amplitude and 50% cycle for 1 minute, repeated times 5 (Ikasonic U200S—IKA Labortechnik) resulted in greater specific activity (45 ng/ml) due to the exposure of additional hGH molecules on the surface of the aggregates.

The activity of isolated RX3-hGH fusion proteins were also determined following solubilized from RPBLAs isolated by density gradient (F56, diluted 3-fold in buffer PBP4 and centrifuged at 80000×g in a swinging-bucket for 2 hours). The fusion protein was solubilized in buffer S (Tris 50 mM, pH8 and 2% of β-ME) and sonicated (Clycle 5, Amplitude 50%, 1 minute, repeated five times; Ikasonic U200S—IKA Labortechnik). After incubation at 37° C. for 2 hours, the sample was centrifuged at 5000×g for 10 minutes, and the supernatant containing the soluble RX3-hGH fusion protein was assayed to assess the bioactive component of the fraction. The amount of fusion protein in the supernatant was determined to be 250 ng/ml by ELISA (Active® Human Growth Hormone ELISA—DSL-10-1900; Diagnostic Systems Laboratories, Inc). The protein assayed in the bioactivity ELISA assay (Active® Bioactive Human Growth Hormone ELISA—DSL-10-11100; Diagnostic Systems Laboratories, Inc) gave a result of 70 ng/ml, indicating that about 30% of the RX3-hGH fusion protein was active. The loss of hGH activity could be a consequence of the high concentration of reducing agent used in the solubilization, or due to some impairing effect of the RX3 domain over the hGH or the hGH binding protein.

Finally, the RX3-hGH fusion protein was cleaved by a site specific protease to liberate the hGH from the fusion protein.

The solubilized RX3-hGH fusion protein was diluted 2-fold and the digestion was performed using the EKmax kit as described by the manufacturer (Invitrogen). Free hGH was isolated from the insoluble uncleaved fusion protein fraction by centrifugation at 16000×g at 4° C. for 1 hour. The soluble hGH was recovered from the supernatant and assayed for bioactivity as described above. The same value of 90 ng/ml was obtained for the quantification and bioactivity ELISA assays (Active® Human Growth Hormone ELISA—DSL-10-1900; Diagnostic Systems Laboratories, Inc) and Active® Bioactive Human Growth Hormone ELISA—DSL-10-11100; Diagnostic Systems Laboratories, Inc) indicating that all the protein present as detected by the quantification kit is also in the biologically active conformation.

Summary table for the quantification and bioactivity of the hGH protein in all the formulations is presented below:

| Formulation | Quantification Amount ng/ml | Bioactivity Amount ng/ml |
| --- | --- | --- |
| Intact RPBLAs | 14 | 25 |
| Membrane removed RPBLAs | 35 | 45 |
| Soluble RX3-hGH | 250 | 70 |
| Cleaved hGH | 90 | 90 |

It is important to note that CHO cells stably transfected with the vector p3.1-RX3 were used as a negative control. As shown in FIG. 2B, RX3 without a fusion partner expressed in CHO cells also accumulates in dense structures which can be isolated by density step gradient in F56 (FIG. 2B, lane 5). Moreover, optical analysis of CHO cells transfected with p3.1-RX3, showed that the RX3 protein accumulate in RPBLAs (FIG. 5C) These control RX3 RPBLA preparations and isolated RX3 protein showed no hGH activity in the ELISA bioactivity assay.

Example 6

Activity of DNAb Intein after RX3-Int-hGH Solubilization from RPBLAs from CHO Cells The polynucleotide sequence coding for the Ssp DNAb intein (New England Biolabs) was fused in frame to the 3' end of the RX3 sequence (WO2004003207), and to the 5' end of the hGH cDNA. The resulting construct was cloned into vector pcDNA3.1(−) [FIG. 1A] to form vector p3.1-RX3-I-hGH. As a negative control, an inactive version of the same intein was produced by PCR where the amino acid residue Asp154 was mutated to Ala [FIG. 1A] to form vector p3.1-RX3-Im-hGH. The Asp154 amino acid residue has been reported to be essential for the Ssp DNAb self-cleavage activity (Mathys et al, *GENE* (1999) 231:1-13).

Figure 5:
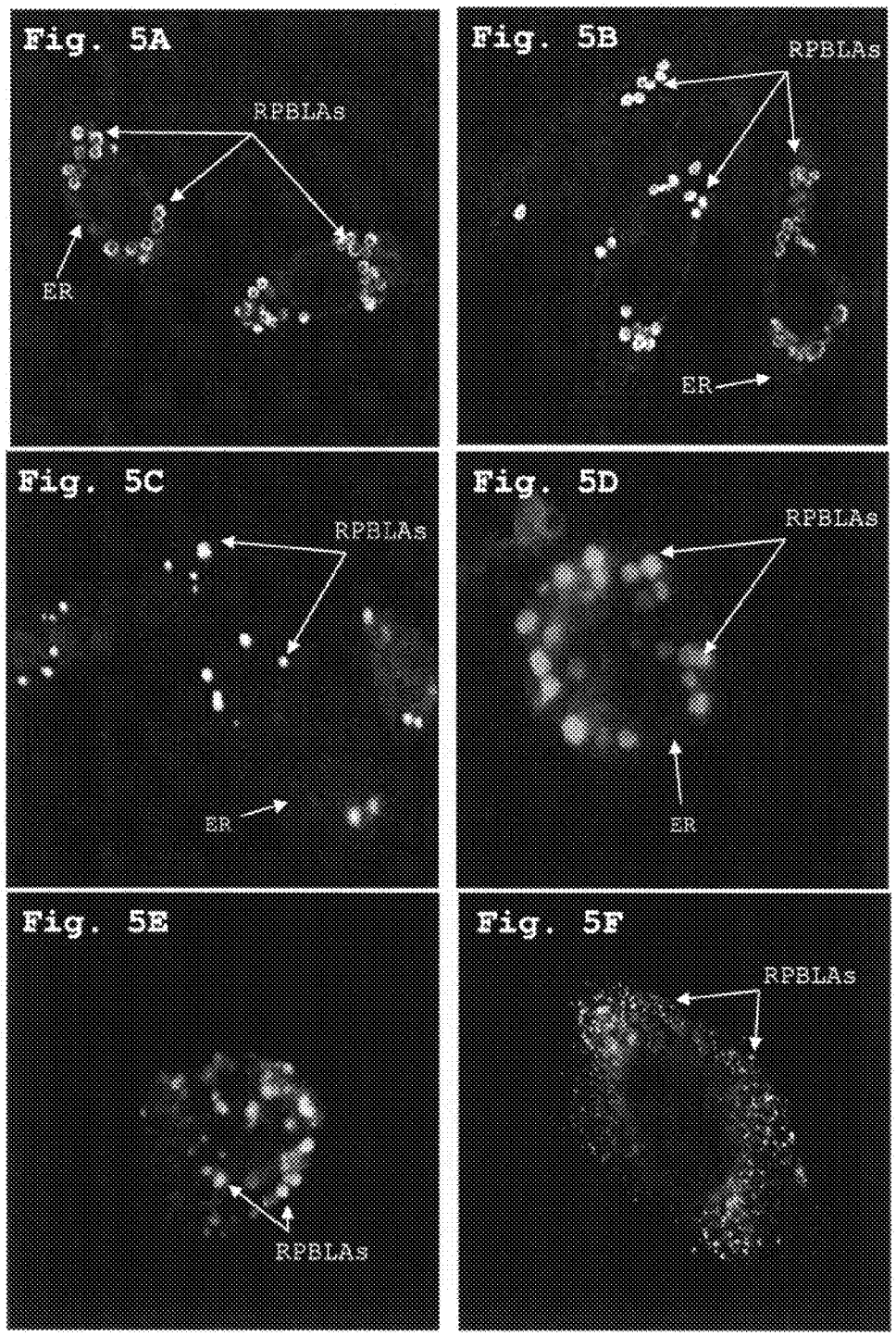
FIG. 5 shows the localization of RX3 fusion proteins inside RPBLAs in CHO cells, four days after transfection. Optical microscopy was used to show CHO cells expressing RX3-hGH (Panels A and B) immunolocalized by using anti-RX3 and anti-hGH serum, respectively. Panel C shows RX3 protein immunolocalized with RX3 antiserum. Anti-hGH serum was used in Panel D to immunolocalize the RX3-I-hGH fusion protein. The incubation of CHO cells expressing RX3-GUS fusion protein with RX3 antiserum is shown in Panel E. Smaller RPBLAs were observed in CHO cells expressing RX3-EK, incubated with anti-RX3 serum (Panel F). The endoplasmic reticulum (ER) and the RPBLAs are indicated.

Immunochemical analysis of CHO cells transfected with p3.1-RX3-I-hGH using anti-hGH antiserum revealed that the fusion protein RX3-Int-hGH accumulated in large round-shaped RPBLAs, similar to the ones observed in CHO cells expressing RX3-hGH (compare FIGS. 5B and 5D). This result indicates that the fusion protein containing the DNAb intein self-assembles and accumulates into high density structures in a similar manner to fusions lacking the intervening intein sequence.

CHO cells transfected with p3.1-RX3-I-hGH were homogenized, the homogenates were loaded in density step gradients, and the fractions corresponding to the different densities were analyzed by immunoblot. Most of the RX3-I-hGH was detected in the fraction F56 corresponding to dense RPBLAs (FIG. 2B). As for other RX3 fusion proteins, the presence of RX3-I-hGH fusion protein in the supernatant probably represents the un-assembled fusion protein contained in the ER and solubilized during the homogenization process.

Once it was demonstrated that the RX3-I-hGH accumulated in RPBLAs, these ER-derived organelles were isolated by low speed centrifugation as described elsewhere herein. The centrifugation of homogenates of CHO cells transfected with p3.1-RX3-I-hGH at 1500×g for 10 minutes permitted the separation of the non-assembled RX3-Int-hGH fusion proteins in the supernatant from the assembled in RPBLAs in the pellet. Equivalent studies were performed with CHO cells expressing the inactive RX3-mInt-hGH fusion protein.

The pellets containing the assembled RX3-Int-hGH and RX3-mInt-hGH fusion proteins were solubilized in S1 buffer (20 mM Tris pH7, 200 mM NaCl, 1 mM EDTA, 0.1% SDS and 0.1 mM TCEP) at 37° C. for 2 hours, and the intein enzymatic activity was induced by incubation at 25° C. for 48 hours after dialysis against the cleavage induction buffer: 20 mM Tris pH 7, 200 mM NaCl, 1 mM EDTA. After induction of intein self-cleavage, the composition was centrifuged at 16000×g for 10 minutes and the supernatant and the pellet analyzed by immunoblot using anti-RX3 and anti-hGH antiserum.

Both fusion proteins were solubilized, but only the fusion protein containing the active intein (RX3-Int-hGH) was able to self-cleave (FIGS. 6A and 6B, black arrowheads). The absence of self-cleavage of the mutated RX3-mInt-hGH fusion protein demonstrates that the self-cleavage observed with the RX3-Int-hGH is due to the specific activity of the intein, and not due to some endogenous protease activity co-purified during the RPBLAs isolation process.

To optimize the efficiency of intein self-cleavage, alternative solubilization protocols were assayed. The intein self-cleavage of the RX3-Int-hGH can be compared, after solubilization with the S1 buffer and the biphasic extraction protocol (S2) described elsewhere (FIG. 6C). From the ratio between the remaining of the full-length fusion protein and the appearance of the band corresponding to the liberated hGH, even though the biphasic extraction protocol was the more efficient permitting more than 50% of cleavage, it can be concluded that in both cases a large proportion of DNAb intein was active and able to self-cleave.

Example 7

Activity of RX3-EGF Assembled in RPBLAs in Tobacco Plants

RPBLAs from transgenic tobacco plants expressing the RX3-EGF fusion protein were isolated by low speed centrifugation essentially as described in U.S. Ser. No. 11/289,264. The fusion protein was solubilized by sonication (Cycle 5, Amplitude 50%, 1 minute, repeated five times; Ikasonic U200S—IKA Labortechnik) in 50 mM Tris pH 8 and 2% of β-ME and incubation at 37° C. for 2 hours. Afterwards, the solubilized material was centrifuged at 16000×g at 4° C. for 30 minutes to discard the unsolubilized fusion protein in the pellet. The supernatant was dialyzed against 50 mM Tris pH 8 to remove the β-ME, centrifuged once again at 16000×g at 4° C. for 30 minutes, and the supernatant quantified by the hEGF kit from Biosource International Inc. (KHG0062).

The bioactivity of EGF was analyzed by determining the proliferation rate (radioactive thymidine incorporation to DNA) of MDA-MB231 cells (breast cancer cells that overexpress EGF receptor) incubated with 1.2 ng/mL of RX3-EGF fusion protein. As a positive control, MDA-MB231 cells were incubated with 10 ng/mL of commercial EGF (Promega) or fetal calf serum (FCS). The results, summarized in the following Table, are represented as percentage (%) of proliferation with regard to the basal proliferation rate of MB231 cells (100%), determined as the proliferation rate of these cells cultivated in the absence of EGF (deprived).

| | Proliferation of MDA-MB231 cells | | |
|---|---|---|---|
| | | % proliferation with respect to Deprived cells | |
| Sample | Concentration | Mean | STD |
| Deprived | — | 100 | — |
| FCS | — | 145 | 1.27 |
| EGF (Promega) | 10 ng/mL | 158 | 11.7 |
| RX3-EGF | 1.2 ng/mL | 146 | 4 |

As expected, the supplementation of MB231 cell culture with commercial EGF (Promega) or the FCS produced a significant increase of the proliferation rate (158% and 145%, respectively). Remarkably, the addition of 1.2 ng/mL of RX3-EGF also produced an increase of 146% of the proliferation rate. It is important to note that almost the same proliferation rate was observed with 10-fold more concentration of commercial EGF than with RX3-EGF. This surprising result could be explained by previous results showing that saturation of the proliferation rate of MB231 cell was observed at 5 ng/mL of the commercial EGF. Another possible explanation could be a more active conformation of EGF when fused to RX3. In any case, this result shows that RX3-EGF is at least as active as the commercial hGH (Promega).

Example 8

Activity of RX3-GUS Assembled in RPBLAs in CHO Cells

The β-glucuronidase enzyme (GUS) is a broadly used reporter protein (Gilisen et al., *Transgenic Res.* (1998) 7(3): 157-163). The expression of an active RX3-GUS fusion protein in RPBLAs was predicted to be difficult due to the protein's large size (ca. 70 kDa) and the presence of 9 cysteine residues.

The polynucleotide sequence coding for RX3 (WO2004003207) was fused in frame to the 5' end of the sequence encoding GUS (FIG. 1A. RX3-GUS), and the resulting construct used to transfect CHO cells as described in Example 7 above. Immunochemical analysis of CHO cells transfected with p3.1-RX3-GUS incubated with anti-RX3 antiserum revealed the presence of large RPBLAs (FIG. 5E). To verify the density of those RPBLAs, CHO cells transfected with the same plasmid were homogenized and loaded onto step-density gradients. The analysis of the different fractions by immunoblot showed that the fusion proteins localized in the higher dense fractions (FIG. 2B. F56), indicating that the RX3-GUS fusion proteins are able to assemble and accumulate in dense RPBLAs. It is important to note that no fusion protein was detected in the supernatant, meaning that almost all RX3-GUS is assembled in dense structures (RPBLAs).

Once it was demonstrated that the RX3-GUS accumulated in RPBLAs, the fusion protein was recovered from the F56 fraction (as described in Example 5 for RX3-hGH) and solubilized in 50 mM Tris, pH 8, β-ME 2% and SDS 0.1% at 37° C. for 2 hours. Afterwards, the solubilized material was centrifuged at 16000×g at room temperature for 10 minutes, and the supernatant containing the soluble disassembled RX3-GUS fusion protein was dialyzed at 4° C. against a 50 mM Tris pH 8 solution over night (about 18 hours).

The GUS activity assay is based in the conversion of metilumbeliferil-β-glucuronide acid (MUG) to the 4-metilumbeliferone (4-MU) fluorescent product (Jefferson et al. 1987 *EMBO J.* 6(13):3901-3907). Fifty μL of the solubilized RX3-GUS fusion protein (about 0.25 ng of RX3-GUS/μL) was incubated in the presence of MUG at room temperature, and the appearance of 4-MU was measured by fluorescence (excitation wavelength 355 nm; emission wavelength 420 nm). To rule out the possibility of an endogenous GUS-like activity in the RPBLA preparation from CHO cells, RPBLAs from CHO cells transfected with p3.1-RX3 were isolated, and the solubilized RX3 protein was included in the activity assay as a control. The table below summarizes the results obtained:

| | Absorbance at 420 nm | | | |
|---|---|---|---|---|
| Time | RX3-GUS | | RX3 | |
| (minutes) | Mean | STD | Mean | STD |
| 0 | 337 | 24 | 227 | 6.4 |
| 30 | 534 | 4.2 | 236 | 15 |
| 60 | 690 | 12.7 | 265 | 9.2 |
| 90 | 909 | 30.4 | 299 | 21.2 |
| 120 | 1049 | 38.9 | 309 | 10.6 |
| 160 | 1141 | 21.9 | 311 | 82 |

From the results shown in this table, it is clear that the RX3-GUS fusion protein remains active once solubilized from the RPBLAs. The specific activity of the RX3-GUS calculated from these experiments was 0.2 pmol of 4-MU/min-1*12.5 ng-1 of RX3-GUS. No significant endogenous GUS-like activity was observed using RX3 RPBLA preparations.

Example 9

Activity of RX3-EK Assembled in RPBLAs in CHO Cells

*Bos taurus* enterokinase (enteropeptidase) is a membrane-bound serine protease of the duodenal mucosa, involved in the processing of trypsinogen to trypsin (DDDK↓) with a chymotrypsin-like serine protease domain. The enteropeptidase is a disulfide linked two-chain peptide formed by the heavy chain ($EK_{HC}$—120 kD) and the catalytic light chain ($EK_{LC}$—47 kD). The catalytic subunit (here referred as EK) is almost as active and specific by itself as the complete holoenzyme (LaVallie et al. 1993 *J. Biol. Chem.* 268(31):23311-23317). It is important to point out that bovine EK has 4 disulphide bonds. Moreover, the N-terminal end of the protein is folded inside the protein, and it is essential for the proper folding of a functional EK. These two EK requirements make EK protein a challenging protein to be expressed as an active protein in RPBLAs.

The polynucleotide sequence coding for RX3 (WO2004003207) was fused through a linker comprising the FXa cleavage site (IEGR) to the 5' end of the EK sequence, and cloned in pcDNA3.1(−) (FIG. 1A, p3.1-RX3-EK).

This construct was used to transfect CHO cells using lipofectamine (Invitrogen). Immunocytochemistry analysis of those transfected cells using anti-RX3 antiserum revealed the presence of a large quantity of small RPBLAs. These organelles were visible all along the cytoplasm of the transfected cells, but their size usually did not exceed 0.5µ (FIG. 5F).

To verify the density of those small RPBLAs, CHO cells transfected with the same plasmid were homogenized and loaded in step-density gradients. The RX3-EK fusion protein was localized in the F56 fraction (FIG. 2B). The high density of the RX3-GUS fusion protein assemblies suggests that this fusion protein accumulates into dense RPBLAs. It is important to note that no fusion protein was detected in the supernatant, meaning that almost all RX3-EK is assembled into aggregates. Interestingly, the molecular weight of the RX3-EK fusion protein was estimated at 58 KDa, about 15 KDa higher than the theoretical molecular weight expected. This result suggests that the EK in the RPBLAs can be glycosylated, as has been described for the natural protein (LaVallie et al., 1993 *J. Biol. Chem.* 268(31):23311-23317).

The fusion protein was recovered from the F56 fraction (as described in Example 5 for RX3-hGH) and solubilized in 50 mM Tris, pH 8, β-ME 2% and SDS 0.1% at 37° C. for 2 hours. To increase the solubilization, the sample was sonicated at 50% amplitude and 50% cycle for 1 minute, repeated 5 times (Ikasonic U200S—IKA Labortechnik), before the SDS addition. Afterwards, the sample was centrifuged at 5000×g at room temperature for 10 minutes, and the supernatant containing the soluble disassembled RX3-GUS fusion protein was dialyzed at 4° C. against a 50 mM Tris pH 8 solution for 18 hours. The fusion protein was digested by FXa as described by the manufacturer (Quiagen), and the EK activity was measured by fluorimetric assay (Grant, et al., 1979 *Biochim. Biophys. Acta* 567:207-215). The liberated EK from the RX3-EK had enteropeptidase activity.

Example 10

Activity of RX3-Casp2 and RX3-Casp3 Assembled in RPBLAs in CHO Cells

Studies were undertaken to determine the activity of caspases produced in RPBLAs. Caspases are a family of cysteine proteases involved in apoptosis that cleave a unique consensus sequence with high specificity. Caspases exist as inactive procaspases with a prodomain of variable length followed by a large subunit (p20) and a small subunit (p10). They are activated through proteolysis and mature active caspase consists of the heterotetramer $p20_2$-$p10_2$ (Lavrik et al., 2005 *J. Clin. Invest.* 115:2665-2671). Caspases are divided into initiator caspases and executioner caspases that differ in their mechanism of action. Caspase2 (initiator caspase) and caspase3 (executioner caspase) have been chosen as an example of proteins which are active in the RPBLAs (Baliga et al., 2004 *Cell Death and Differentiation* 11:1234-1241; Feeney et al., 2006 *Protein Expression and Purification* 47(1):311-318). Those proteins are especially challenging because they are synthesized as zymogens that, to become active, need to be self-cleaved and to form a heterotetramer.

The p3.1-RX3-C2 and p3.1-RX3-C3 constructs (FIG. 1) were introduced into CHO cells by transient transfection with the lipofectamine protocol (Invitrogen). Four days after transfection, to determine if caspases are accumulated in dense RPBLAs organelles, CHO cells expressing RX3-Casp2 or RX3-Casp2 were homogenized, loaded on a density step gradient and centrifuged as described elsewhere.

The accumulation of both RX3-caspases fusion proteins in the different fractions was analyzed by immunoblot (FIG. 2B). As can be seen, most of the RX3-Casp2 or RX3-Casp2 fusion proteins sediment to fraction F56 and F42 corresponding to dense RPBLAs. This result indicates that these two fusion proteins are able to tightly assemble in dense structures.

In the immunoblot presented in FIG. 2B, only the full length fusion protein is shown, but bands of different molecular weight are present in this fraction. These bands are cross-reactive to either anti-RX3 antibody or anti-CASP (SA-320 and SA-325, Biomol International) antibody correspond to the different caspase subunits, indicating that autocatalytic activation has taken place inside RPBLAs. These observations indicate that Caspase2 and Caspase 3 are active in vivo.

The F56 and F42 fractions were diluted 4-fold in buffer PBP4 and centrifuged at 80000×g in a swinging-bucket to recover the RPBLAs in the pellet. The ER membrane surrounding this organelle was removed by washing the RPBLAs preparation with 50 mM Tris pH 8 and 1% Triton X-100. Upon removal of the ER membrane, activity of caspase is assayed using the BIOMOL Quantizyme™ Assay System, CASPASE-3 Cellular Activity Assay Kit PLUS-AK703 (caspase 3) and BIOMOL Quantizyme™ Assay System, CASPASE-2 Cellular Activity Assay Kit PLUS-AK702 (Caspase 2). This kit measures caspase activity colorimetrically with a specific substrate. The RX3-Casp2 and the RX3-Casp3 RPBLAs show caspase activity.

In determining the activity of caspases fused to RX3, the fusion protein is solubilized from RPBLAs isolated by density gradient (F56 and F42, diluted 4-fold in buffer PBP4 and centrifuged at 80000×g in a swinging-bucket). The fusion protein is solubilized in buffer CA (50 mM Hepes, pH 7.4, 100 mM NaCl, 1 mM EDTA, 100 mM DTT, 1% CHAPS, 10% glycerol) after sonication (50% amplitude and 50% cycle for 30 seconds, 5 times). Solubilization is performed by a 2-hour incubation at 37° C. and insoluble material is discarded by centrifugation at 16000×g for 10 minutes. The supernatant containing the soluble RX3-casp fusion protein is dialyzed against caspase kit assay buffer (50 mM Hepes, pH 7.4, 100 mM NaCl, 1 mM EDTA, 10 mM DTT, 0.1% CHAPS, 10% glycerol). Activity of the dialyzed sample containing RX3-Casp2 and RX3-Casp3 are assessed with the BIOMOL QuantiZyme™ Assay System, CASPASE-3 Cellular Activity Assay Kit PLUS-AK703 (caspase 3) and BIOMOL Quantizyme™ Assay System, CASPASE-2 Cellular Activity Assay Kit PLUS-AK702 (caspase 2). Caspase 2 and Caspase 3 are active.

Example 11

Activity of RX3-RTB Assembled in RPBLAs in Agroinfiltrated Tobacco Plants

The polynucleotide sequence coding for RTB (Reed et al., 2005 *Plant Cell Report* 24:15-24) was fused in frame to the 3' end of RX3 domain and cloned in a binary vector (pB-RX3-RTB). This construct was used in tobacco plants transformed by syringe agroinfiltration, as described elsewhere. The agroinfiltrated tobacco leaves were homogenized and loaded in step density gradients. The RX3-RTB fusion protein was localized to fractions F42 and F56 (FIG. 2B), consistent with the fusion protein self-assembling and accumulating in dense RPBLAs. As described for RX3-EK, the RX3-RTB fusion protein isolated from the RPBLAs has a lower electrophoretic mobility compared to the theoretical molecular weight. This results supports that RTB also can be glycosylated in RPBLAs.

The fusion protein was recovered from those dense fractions (as described in Example 5 for RX3-hGH) and solubilized in 50 mM Tris, pH 8, β-ME 0.8% at 37° C. for 2 hours. To increase the solubilization, the sample is sonicated at 50% amplitude and 50% cycle for 1 minute, repeated 5 times (Ikasonic U200S—IKA Labortechnik). Subsequently, the sample is centrifuged at 5000×g at room temperature for 10 minutes, and the supernatant containing the soluble disassembled RX3-RTB is analyzed by ELISA for binding to the glycoprotein fetuin treated with sialydase to expose galactose-terminated glycans, and they bind.

Example 12

Plasmid Construction for Plant Transformation

The coding sequences of human epidermal growth factor (hEGF) were obtained synthetically and were modified in order to optimize its codon usage for expression in plants.

```
hEGF protein
                                        SEQ ID NO:41
NSDSECPLSH DGYCLHDGVC MYIEALDKYA CNCVVGYIGE

RCQYRDLKWW ELR hEGF DNA
                                        SEQ ID NO:42
aactctgatt cagaatgccc actcagtcac gacggatatt gtcttcacga tggggtatgc atgtacatcg aggccttgga caagtacgca tgtaattgtg tagtgggata cattggtgaa cgctgtcagt atcgagactt gaaatggtgg gagcttaggt ga
```

The synthetic gene encoding the 53 amino acids of active hEGF was obtained by primer overlap extension PCR method, using 4 oligonucleotides of around 60 bases, with 20 overlapping bases. The synthetic hEGF cDNA included a 5' linker sequence corresponding to the Factor Xa specific cleavage site. The oligonucleotides were purified by polyacrylamide denaturing gel.

Synthetic hEGF cDNA was purified from agarose (Amersham) following gel electrophoresis and cloned into the PGEM vector (Promega). The RX3 cDNA fragment (coding for an N-terminal domain of gamma-zein) containing cohesive ends of BspHI and NcoI, was inserted into the vector pCKGFPS65C (Reichel et al., 1996 *Proc. Natl. Acad. Sci. USA* 93:5888-5893) previously digested with NcoI (as described in patent application WO2004003207). The sequence coding for EGF was fused in frame to the RX3 sequence. The constructs RX3-EGF was prepared by substitution of the GFP coding sequence for the EGF synthetic gene.

The resulting construct named pCRX3EGF contained a nucleic acid sequence that directs transcription of a protein as the enhanced 35S promoter, a translation enhancer as the tobacco etch virus (TEV), the EGF coding sequence and the 3' polyadenylation sequences from the cauliflower mosaic virus (CaMV). Effective plant transformation vector p19RX3EGF was ultimately obtained by inserting the HindIII/HindIII expression cassettes into the binary vector pBin19 (Bevan, 1984 *Nucleic Acids Research* 12:8711-8721).

The cDNA encoding the alpha-zein of 22 kD (22aZ) and the rice prolamin of 13 kD (rP13) were amplified by RT-PCR from a cDNA library from maize W64A and Senia rice cultivar, respectively. The oligonucleotides used in the PCR reaction were:

```
22aZ-5'
                                        SEQ ID NO:43
5' GAGGATCCGCATGGCTACCAAGATATTAGCCCT3'

22aZ-3'
                                        SEQ ID NO:44
5' CATTCATGATTCCGCCACCTCCACCAAAGATGGCACCTCCAACGATG

G3'

Rice13Prol-5'
                                        SEQ ID NO:45
5' GAGTCGACGGATCCATGAAGATCATTTTCGTCTTTGCTCTCC3'

Rice13Prol-3'
                                        SEQ ID NO:46
5' CATCCATGGTTCCGCCACCTCCACCCAAGACACCGCCAAGGGTGGTA

ATGG3'
```

The corresponding PCR fragments were cloned in the pCRII vector (Invitrogen), sequenced and cloned in pUC18 vectors containing the enhanced CaMV 35S promoter, the TEV sequence and 3' ocs terminator. The pCRII-rP13 was digested by SalI and NcoI, and cloned in the pUC18RX3Ct, pUC18RX3hGH and pUC18RX3EGF plasmids digested by the same enzymes to obtain plasmid pUC18rP13EGF. The pCRII-22aZ was digested by SalI/NcoI and cloned in the pUC18RX3EGF plasmid digested by the same enzymes to obtain plasmid pUC1822aZtEGF. Finally, the pUC18-derived vector was cloned in pCambia 5300 by HindIII/EcoRI.

The construct pBIN m-gfp4-ER, contain an optimized GFP for expression in plants (Haseloff et al., 1997 *Proc. Natl. Acad. Sci. USA* 94:2122-2127). This construct was used as template for PCR amplification of the GFP. The oligonucleotides were designed to eliminate the signal peptide and HDEL motif present in the original sequence as well as to introduce the restriction sites for further cloning.

```
Primers:
GFP 5':
                                        SEQ ID NO:50
5' AATTCATGAGCAGTAAAGGAGAAGAACTTTTCAC 3'

GFP 3':
                                        SEQ ID NO:51
5' ATTGGATCCTCATTATTTGTATAGTTCATCCATGC 3'
```

The PCR product was cloned in a PCR cloning vector (PCR®II Vector, Invitrogen)) and the sequence verified. The GFP fragment containing cohesive ends RcaI/BamHI was cloned into pUC18RX3hGH (US2006123509 (A1)), giving the cassette RX3-GFP in a pUC18 vector. This cassette was liberated by HindIII/BamHI digestion and subsequently inserted in a pCAMBIA 2300 vector (pB-RX3-GFP)

The RTB clone (GenBank accession no. X03179) was amplified by PCR (RTB5 and RTB3) and digested by RcaI/SmaI. The digested PCR fragment was cloned in pUC18RX3hGH (US2006123509 (A1)) digested by NcoI/SmaI to obtain pUC18RX3RTB. Then, this vector was digested by HindIII/EcoRI and the liberated fragment cloned in a pCAMBIA 2300 vector digested by the same restriction enzymes (pB-RX3-RTB)

```
Primers:
RTB5:
                                         SEQ ID NO:52
5' AATTCATGAGCAGTAAAGGAGAAGAACTTTTCAC 3'

RTB3:
                                         SEQ ID NO:53
5' TTACCATTATTTTGATACCCGGGAAG 3'
```

Plant Material

Tobacco (*Nicotiana tabacum* var. Wisconsin) plants were grown in an in vitro growth chamber at 24-26° C. with a 16 hour photoperiod. Adult plants were grown in greenhouse between at 18-28° C., humidity was maintained between 55 and 65% with average photoperiod of 16 hours.

Plantlets for agroinfiltration (Vaquero et al., 1999 *Proc. Natl. Acad. Sci., USA* 96(20):11128-11133; Kapila et al., 1997 *Plant Sci.* 122:101-108) method were grown from seeds for 4-6 weeks in the in vitro conditions described above.

Tobacco Stable Transformation

The binary vectors were transferred into LBA4404 strain of *A. tumefaciens*. Tobacco (*Nicotiana tobaccum*, W38) leaf discs were transformed as described by Draper and Hamil 1988, In: *Plant Genetic Transformation and Gene Expression. A Laboratory Manual* (Eds. Draper, J., Scott, R., Armitage, P. and Walden, R.), Blackwell Scientific Publications. Regenerated plants were selected on medium containing 200 mg/L kanamycin and transferred to a greenhouse. Transgenic tobacco plants having the highest transgene product levels were cultivated in order to obtain T1 and T2 generations.

Recombinant protein levels were detected by immunoblot. Total protein extracts from tobacco leaves were quantified by Bradford assay, separated onto 15% SDS-PAGE and transferred to nitrocellulose membranes using a Mini Trans-Blot Electrophoretic Transfer Cell (Bio Rad). Membranes were incubated with gamma-zein antiserum (dilution 1/7000) (Ludevid et al. 1985, *Plant Science* 41:41-48) and were then incubated with horseradish peroxidase-conjugated antibodies (dilution 1/10000, Amersham Pharmacia). Immunoreactive bands were detected by enhanced chemiluminescence (ECL western blotting system, Amersham Pharmacia).

Tobacco Agroinfiltration

Vacuum Agroinfiltration

Plantlets for agroinfiltration method were grown from seeds for 4-6 weeks in an in vitro growth chamber at 24-26° C. with a 16 hour photoperiod.

*A. tumefaciens* strain LB4404 containing a desired construct was grown on LB medium (Triptone 10 g/l, yeast extract 5 g/l, NaCl 10 g/l) supplemented with kanamycin (50 mg/l) and rifampin (100 mg/l) at 28° C. with shaking (250 rpm) overnight (about 18 hours). *Agrobacterium* cells were inoculated into 30 ml of LB also supplemented with kanamycin (50 mg/l) and rifampin (100 mg/l). After overnight culture at 28° C. cells were collected by centrifugation for 10 minutes at 3000×g and resuspended in 10 ml of liquid MS medium with MES (Sigma Chemical) 4.9 g/l and sucrose 30 g/l at pH 5.8. Bacterial cultures were adjusted to a final $OD_{600}$ of 0.1 and supplemented with acetosyringone to a final concentration of 0.2 mM and incubated for 90 min at 28° C.

For agroinfiltration, plantlets were totally covered with the suspension and vacuum was applied (100 KPa) for 5-6 seconds. The suspension was removed and plantlets maintained in a growth chamber at 24-26° C. under a photoperiod of 16 hours for four days. Plant material was recovered and total protein extracts were analyzed by immunoblot using anti-gamma-zein antibody.

Agroinfiltration by Syringe

*Agrobacterium tumefaciens* strain EHA 105 was grown to stationary phase at 28° C. in L-broth supplemented with 50 μg mL$^{-1}$ kanamycin and 50 μg mL$^{-1}$ rifampin. Bacteria were sedimented by centrifugation at 5000 g for 15 minutes at room temperature and resuspended in 10 mM MES buffer pH 5.6, 10 mM $MgCl_2$ and 200 μM acetosyringone to a final $OD_{600}$ of 0.2. Cells were left in this medium for 3 hr at room temperature. Individual *Agrobacterium* cultures carrying the RX3 constructs and the HC-Pro silencing suppressor constructs (Goytia et al., 2006) were mixed together and infiltrated into the abaxial face of leaves of 2-4-week-old *Nicotiana benthamiana* plants (Voinnet et al, 2003).

Example 13

Isolation (Purification) of RPBLAs by Density Gradient from Transgenic Plant Vegetative Tissues The gene coding for RX3-EGF gamma-zein derived fusion proteins was introduced into tobacco plants via *Agrobacterium tumefaciens*. Transformed plants were analyzed by immunoblot to identify those with higher recombinant protein expression. The fusion proteins usually accumulated as multimers and the amount of monomers and oligomers detected in the immunoblots depended on the disulfide bond reduction state.

Tobacco leaf extracts were loaded on density step gradients and the accumulation of recombinant proteins in the different fractions was analyzed by immunoblot. The results indicate that RX3-EGF appeared in fractions corresponding to dense RPBLAs. Most of these organelles exhibited densities higher than 1.2632 g/cm$^3$ and a significant portion of them showed a density higher than 1.3163 g/cm$^3$. These densities were comparable to or higher than that of natural maize PBs (Ludevid et al., 1984 *Plant Mol. Biol.* 3:227-234; Lending et al., 1989 *Plant Cell* 1:1011-1023).

It was estimated that more than 90 percent of the recombinant protein was recovered in the dense RPBLAs fractions and pellet. Thus, isolation of RPBLAs by density appears to be a useful system to purify (concentrate) the fusion proteins.

To evaluate the purification of the recombinant protein RX3-EGF by RPBLAs isolation, the different density fractions were analyzed by silver stain. More than 90 percent of tobacco endogenous proteins were located in the soluble and the interphase fractions of the gradient where the RX3-EGF protein was absent or barely detected. Thus, soluble proteins and the bulk of proteins present in less dense organelles could be discarded by selecting one or two fractions of the gradient.

In respect to the degree of fusion proteins purification in the RPBLAs fractions, it was estimated that RX3-EGF protein represents approximately 80 percent of the proteins detected in the PBLS-containing fractions. This result indicates that, using an RPBLA isolation procedure, one can achieve an important enrichment of fusion proteins in only one step of purification.

Example 14

Recombinant Proteins Recovery in RPBLAs Isolated from Dry Plant Tissues

The ability of RPBLAs to stabilize and protect recombinant proteins of interest was assessed by means of accelerated stability testing using heat-dried plant leaf biomass. Transformed tobacco leaves accumulating RX3-EGF fusion protein were dried at 37 C for one week and then stored at room temperature under low humidity conditions. After 5 months of dry storage, the levels of recombinant proteins were compared to those of identical leaves harvested at the same time but frozen at −80 C instead of being heat-dried. Protein extracts from equivalent amounts of fresh-frozen and dried leaf tissue were analyzed by immunoblot. The RX3-EGF protein was found to be highly stable in desiccated transformed plants, as the amount recovered in wet and dry plants was virtually identical.

The distribution in step density gradients of RX3EGF fusion protein from homogenates of dried leaves was analyzed by immunoblot. The fusion protein was mainly recovered in dense structures exhibiting densities higher than 1.1868 g/cm$^3$ and 1.2632 g/cm$^3$.

Given the abundant proteases and metabolites present in tobacco leaves, the remarkable ability of RPBLA sequestration to protect recombinant proteins was unexpected. However, similar results were subsequently obtained using rice seed expressing RX3 which had been dried for prolonged periods.

Example 15

Recombinant Protein Recovery by Isolation of RPBLAs from Transiently Transformed Tobacco Plantlets The transient expression systems can be a convenient tool to test the accumulation of recombinant proteins over a short period of time. Thus, the recombinant protein RX3-EGF was also expressed and accumulated in transiently transformed tobacco plantlets via agroinfiltration. The protein extracts from transformed plantlets analyzed by immunoblot show the characteristic complex electrophoretic pattern observed from stably-transformed plants, indicating that the fusion proteins assemble correctly using this method of transformation.

Example 16

Recovery of Recombinant Proteins by Low and Medium Speed Centrifugation

To simplify the procedure used to purify recombinant proteins via dense recombinant protein body-like assemblies, two additional alternative methods were performed: i) clarified homogenates were centrifuged through only one dense sucrose cushion and ii) clarified homogenates were centrifuged without gradients at low speed (i.e. 1000-2500×g for 10 minutes).

In agreement with the previously described results, the RX3-EGF protein was recoverable at high yields (greater than 90%) in pellets obtained after centrifugation through 1.1868 g/cm3 sucrose cushions. In addition, the purification of RX3-EGF protein was still effective in that contaminating endogenous tobacco proteins were barely detected in the corresponding pellet.

The principal advantage of this method as compared to step-density gradients lies in its easy scalability for industrial production of recombinant proteins. It should be noted that the cushion density as well other properties such as its viscosity and osmolarity can be adjusted in each case in order to optimize recovery and purification of the recombinant proteins.

In addition, low speed centrifugation (LSC) was also assayed to concentrate and purify fusion protein-containing protein body-like structures. The results indicated that, after 1000×g for 10 minutes, practically all the RX3-EGF fusion protein was recovered in the pellet. But the staining of the proteins contained in this pellet revealed that the fusion protein was not highly purified as compared with that obtained after centrifugation through 1.1868 g/cm3 sucrose cushion.

Thereafter, the first pellet obtained by low speed centrifugation washed by using a buffer containing 5% Triton X-100. After washing, the sample was centrifuged at 12,000×g for 5 minutes and, interestingly, the bulk of contaminating proteins present in the P1 pellet were eliminated after washing and centrifugation and the new pellet contained a highly enriched RX3-EGF protein. The amount as well the pattern of proteins noted in this study was similar to those obtained after washing the pellet obtained by centrifugation through the sucrose cushion in the Triton X-100-containing buffer. The low speed centrifugation alternative is based on the high density of the structures containing fusion proteins and centrifugation conditions can be optimized for every target before scale-up.

Transgenic tobacco plants expressing fusion proteins including EGF linked to rice prolamin or alpha-zein rather than RX3, rP13-EGF and the 22aZ-EGF, were produced by *Agrobacterium tumefasciens* transformation. Highly-expressing lines were identified by immunoblot using an antibody against EGF, and those cell lines were used in a comparative analysis with tobacco plantlets agroinfiltrated with the same constructs. In all cases, the RPBLAs where recovered in unique interface, suggesting that the RPBLAs are very dense and homogeneous.

Taking all these results together, it is clear that a broad range of prolamins are able to induce high-density RPBLAs, even when they are fused to heterologous proteins. This was an unexpected result, as almost no homology exists between the various prolamins of diverse origin, and suggests that structural rather than sequence-specific motifs may mediate RPBLA formation. Moreover, some data suggests that the different prolamins interact to stabilize the natural PBs of cereals. In contrast to gamma-zein, alpha-zein for example might not be stable when expressed alone in vegetative tissue (Coleman et al., 1996 *Plant Cell* 8:2335-2345).

Example 17

Extraction of Recombinant Proteins from Isolated RPBLAs

Like isolation of bacterial inclusion bodies, isolation of dense recombinant PB-like assemblies is an advantageous method to recover recombinant proteins with high yield and high pre-purification levels from transgenic organisms. Here it is shown that these recombinant proteins can be extracted from the storage organelles.

RX3-EGF proteins were solubilized following overnight (ca. 18 hr) incubation of RPBLA fractions at 37° C. in a buffer containing a detergent and reducing agents (SB buffer with sodium borate 12.5 mM pH 8, 0.1% SDS and 2% β-mercaptoethanol). The extracted fusion proteins were recovered in a soluble form for further purification or use directly as partially-purified extracts.

Example 18

Plasmid Construction for Animal Cell Transformation

The RX3 sequence was amplified by PCR to obtain the cDNA fragments corresponding to RX3 and RX3-(Gly)x5. These fragments were digested by SalI/BamHI cloned in plasmid pECFP-N1 (Clontech) digested by the same enzymes to obtain pRX3-ECFP and pRX3-G-ECFP plasmids, respectively.

```
Primers:
SPfor:
                                       SEQ ID NO:54
5' CAGTCGACACCATGAGGGTGTTGCTCGTTGCCCTCGCTC 3'

RX3ECFP3':
                                       SEQ ID NO:55
5' GGTGGATCCCTAGAATCCATGGTCTGGCAC 3'

RX3G5ECFP3':
                                       SEQ ID NO:56
5' GGTGGATCCCTAGAGCCACCGCCACCTCCATCCATGGTCTGGCA 3'
```

The p22aZ-ECFP vector corresponds to the following HindIII/XbaI DNA fragment in pEGFP-N1 plasmid (Clontech).

```
                                       SEQ ID NO:57
aagcttcgaattctgcagtcgacaacatggctaccaagatattagccctc
cttgcgcttcttgccctttttgtgagcgcaacaaatgcgttcattattcc
acaatgctcacttgctcctagtgccattataccacagttcctcccaccag
ttacttcaatgggcttcgaacacctagctgtgcaagcctacaggctacaa
caagcgcttgcggcaagcgtcttacaacaaccaattaaccaattgcaaca
acaatccttggcacatctaaccatacaaaccatcgcaacgcaacagcaac
aacagttcctaccagcactgagccaactagatgtggtgaaccctgtcgcc
tacttgcaacagcagctgcttgcatccaacccacttgctctggcaaacgt
agctgcataccaacaacaacaattgcagcagtttctgccagcgctca
gtcaactagccatggtgaaccctgccgcctacctacaacagcaacaactg
cttcatctagccctctcgctgtgggtaatgcacctacatacctgcaaca
acaattgctgcaacagattgtaccagctctgactcagctagctgtggcaa
accctgctgcctacttgcaacagctgcttccattcaaccaactgactgtg
tcgaactctgctgcgtacctacaacagcgacaacagttacttaatccact
agaagtgccaaacccattggtcgctgccttcctacagcagcaacaattgc
taccatacagccagttctctttgatgaaccctgccttgtcgtggcagcaa
cccatcgttggaggtgccatctttggtggaggtggcggaatcatggtgag
caagggcgaggagctgttcaccggggtggtgcccatcctggtcgagctgg
acggcgacgtaaacggccacaagttcagcgtgtccggcgagggcgagggc
gatgccacctacggcaagctgaccctgaagttcatctgcaccaccggcaa
gctgcccgtgccctggcccaccctcgtgaccaccctgacctgggcgtgc
agtgcttcagccgctaccccgaccacatgaagcagcacgacttcttcaag
tccgccatgcccgaaggctacgtccaggagcgcaccatcttcttcaagga
cgacggcaactacaagacccgcgccgaggtgaagttcgagggcgacaccc
tggtgaaccgcatcgagctgaagggcatcgacttcaaggaggacggcaac
atcctggggcacaagctggagtacaactacatcagccacaacgtctatat
caccgccgacaagcagaagaacggcatcaaggccaacttcaagatccgcc
acaacatcgaggacggcagcgtgcagctcgccgaccactaccagcagaac
acccccatcggcgacggccccgtgctgctgcccgacaaccactacctgag
cacccagtccgccctgagcaaagacccaacgagaagcgcgatcacatgg
tcctgctggagttcgtgaccgccgcgggatcactctcggcatggacgag
ctgtacaagtaaagcggccgcgactctaga
```

The GFP was obtained by PCR amplification of the plasmid pEGFP-N1 (Clontech) with specific oligonucleotides containing enzyme restriction sites for further cloning:

```
ECFP NcoI 5':
                                       SEQ ID NO:58
5' GTACCATGGTGAGCAAGGGCGAGGAGCTG 3'

ECFPN1 BamNotSac 3':
                                       SEQ ID NO:59
5' GCAGAGCTCGCGGCCGCGGATCCTTACTTGTACAGCTCGTCCATGCC
G3'
```

The PCR product (GFP) was cloned in a PCR cloning vector (PCR®II Vector, Invitrogen) and the sequence verified. The GFP fragment was excised by NcoI/BamHI digestion and cloned into pUC18RX3hGH (US2006123509 (A1)), giving the cassette RX3-GFP in a pUC18 vector. This cassette was liberated by SalI/BamHI digestion and subsequently cloned into a pcDNA3.1(−) (Invitrogen) previously digested by XhoI/BamHI (p3.1-RX3-GFP)

A construct containing the coding sequence of an improved monomeric DS Red protein (mCherry; Shaner et al., 2004 *Nat. Biotechnol.* 22:1567-1572) was used as a template in a PCR reaction (mCherry RcaI 5'/ECFPN1 BamNotSac 3').

```
mCherry RcaI 5'
                                       SEQ ID NO:60
5' ATCATGATGGTGAGCAAGGGCGAG 3'
```

The PCR product (DsRed) was cloned in a PCR cloning vector (PCR®II Vector, Invitrogen)) and the sequence verified. The DsRed fragment was excised by RcaI/BamHI digestion and cloned into pUC18RX3hGH (US2006123509 (A1)), giving the cassette RX3-DsRed in a pUC18 vector. This cassette was liberated by SalI/BamHI digestion and subsequently cloned into a pcDNA3.1(−) (Invitrogen) previously digested by XhoI/BamHI (p3.1-RX3-DsRED)

To obtain a RX3 cDNA with a STOP codon at the 3' end, the RX3 fragment was amplified by PCR (SPFOR/RX3STOP) and digested by SalI/BamHI. The fragment was cloned in pcDNA3.1(−) digested by the same restriction enzymes to obtain p3.1-RX3.

```
RX3STOP3':
                                       SEQ ID NO:61
5' TCGGATCCTTCTAGAATCATCAGGTCT 3'
```

The cDNA encoding the hGH were fused to the RX3 N-terminal gamma-zein coding sequence (patent WO2004003207) and was introduced into the vector pcDNA3.1(−) (Invitrogen) as described elsewhere. In the resulting construct named p3.1RX3hGH, the fusion protein sequences were under the CMV promoter and the terminator pA BGH.

The Ssp DNAb intein from pTWIN1 plasmid (New England Biolabs) and the hGH cDNA were amplified by PCR. Both PCR fragments were fused in frame, also by PCR, digested by NcoI/BamHI and cloned in pUC18RX3hGH (US2006121573 (A1)) vector also digested by NcoI/BamHI. The RX3-Int-hGH insert was obtained by SalI/BamHI digestion of this intermediate vector and cloned in pcDNA3.1(−) (Invitrogen) digested by XhoI/BamHI. The resulting construct was named p3.1-RX3-I-hGH. The PCR product was digested by BsRGI/BamHI and cloned in p3.1-RX3-I-hGH plasmid digested with the same restriction enzymes.

```
Primers:
5'DNAb:
                                         SEQ ID NO:62
5' AGCCATGGCGCGAGTCCGGAGCTATCTCTG 3'

3'DNAb:
                                         SEQ ID NO:63
5' GTTGTGTACAATGATGTCATTCG 3'

DNAb-hGH:
                                         SEQ ID NO:64
5' GAATGACATCATTGTACACAACTTCCCAACCATTCCCTTATCC 3'

3'hGH:
                                         SEQ ID NO:65
5' ATGGTACCACGCGTCTTATCAGAAGCCACAGCTGCCCTCC 3'
```

As a negative control for cleavage induction, a non-cleavable Ssp DnaB was engineered. The mutated (Asp154→Ala154) Ssp DnaB intein fused in frame to the hGH was obtained by PCR from p3.1-RX3-I-hGH.

```
Primers:
IM-for:
                                         SEQ ID NO:66
5' ATCATTGTACACGCCTTCCCAACCATTCCCTTATCC 3'

IM-rev:
                                         SEQ ID NO:67
5' TCAGGATCCTTATCAGAAGCCACAGCTGCCCTCCA 3'
```

Full length cDNAs of human caspase-2 (IRAUp969A0210D6) and caspase-3 (IRATp970B0521D6) were acquired from RZPD GmbH (Berlin), based on an original sequence reference from the Lawrence Livermore National Laboratory.

The caspase-3 and the caspase-2 specific cleavage sites (DEVD and DEHD, respectively) were added by PCR at the 5' termini of the corresponding caspase sequences. It is important to note that amplified fragment corresponding to caspase-2 did not contain the pro-domain.

```
Casp3 forward
                                         SEQ ID NO:68
5' GACTCATGATCGATGAGGTGGACATGGAGAACACTGAAAACTCA
G 3'

Casp3 reverse
                                         SEQ ID NO:69
5' CTGGGTACCATGTCTAGATCATTAGTGATAAAAATAGAGTTCTTTTG
TG3'

Casp2 for
                                         SEQ ID NO:70
5' GACTCATGATCGATGAGCACGACGGTCCTCTCTGCCTTCAGGT 3'

Casp2 reverse
                                         SEQ ID NO:71
5' CTGGGTACCATGTCTAGATAATCATGTGGGAGGGTGTCCTGGG 3'
```

The amplified sequences were cloned into pUC18RX3hGH (US2006123509 (A1)) by digesting with NcoI and KpnI. The resulting construct was then digested by SalI/KpnI and cloned to a pcDNA3.1 (Invitrogen) vector digested by XhoI/KpnI. The corresponding vectors were named (p3.1-RX3-C2 and p3.1-RX3-C3).

The pUC18RX3hGH (US2006123509 (A1)) vector was digested by HindIII/EcoRI, and the liberated insert cloned into pCambia2300 also digested by these enzymes. The corresponding vector was digested by HindIII/NcoI and the insert cloned in pCambia1381 opened by HindIII/NcoI (p4-17). The DNA comprising the RX3-(gly)x5-GUS fragment was obtained by digesting p4-17 with BstEII, filling in the overhang with Klenow and finally digesting with SalI. The resulting fragment was cloned into pcDNA3.1(−) digested by XhoI/EcoRV to obtain the p3.1-RX3-GUS clone.

The p3.1-RX3-EK corresponds to the following NheI/HindIII DNA fragment in pcDNA3.1(−) (Invitrogen)

```
                                         SEQ ID NO:72
gctagcgtttaaacgggccctctagactcgacaccatgagggtgttgctc
gttgccctcgctctcctggctctcgctgcgagcgccacctccacgcatac
aagcggcggctgcggctgccagccaccgccgccggttcatctaccgccgc
cggtgcatctgccacctccggttcacctgccacctccggtgcatctccca
ccgccggtccacctgccgccgccggtccacctgccaccgccggtccatgt
gccgccgccggttcatctgccgccgccaccatgccactaccctactcaac
cgccccggcctcagcctcatcccagccacacccatgcccgtgccaacag
ccgcatccaagcccgtgccaaaggcgcgccggtggaggcggaggtaccat
gattgagggtaggattgttggtgaagtgattcccgtgaaggtgcttggc
cttgggttgtggctctttatttcgatgatcagcaagtttgtggagcctcc
cttgtttctagagattggcttgtgtctgctgcacattgcgtgtatggaag
aaatatggaaccaagtaagtggaaggcagttcttggattgcatatggctt
caaatcttacaagtccacagattgaaactcgtctcatcgatcaaattgtt
atcaacccacactataacaagaggagaaaaaacaatgatattgctatgat
gcatcttgagatgaaagtgaactacacagattacattcagccaatttgtc
ttccagaggaaaaccaagttttcccacctggaaggatttgttctattgcc
ggttggggagcacttatctatcaaggatcaactgcagatgttcttcaaga
agcagatgttccacttttgtcaaatgagaaatgccaacagcaaatgcctg
agtataacattactgagaatatggtgtgtgctggatacgaggcaggaggt
gtggattcttgtcagggagattctggaggtcctcttatgtccaggagaa
taacagatggcttttagccggagttacttctttcggataccaatgcgcat
tgccaaatagacctggtgtgtatgctagagttccaaggtttacagagtgg
attcaatcatttctacattgataaggatccgagctcggtaccaagctt
```

Example 19

Plasmid Construction for Insect Infection

The RX3-DsRED fragment from p3.1-RX3-DsRED was digested by XbaI/HindIII and cloned into pFastBacl (Invitrogen) digested also by these two enzymes in order to obtain pF-RX3-DsRED vector.

The DsRED cDNA was amplified by PCR from pF-RX3-DsRED by using the following primers:

```
bGH rev:
                                   SEQ ID NO:73
5' CCTCGACTGTGCCTTCTA 3' bGH rev2:
                                   SEQ ID NO:74
5' CCTCTAGACTCGACCCATGGTGAGCAAGGGCGAGGAG 3'
```

To obtain the pF-DsRED vector, the PCR-amplified DNA fragment was digested by XbaI/HindIII and cloned into pFastBacl (Invitrogen) also digested by XbaI/HindIII.

Example 20

Insect Cell and Larvae Infection

Baculovirus and Larvae

The pFastBac baculoviral expression vector system (Invitrogen) was used for all experiments. The recombinant virus was produced and amplified according to the manufacturer's instructions. Eggs of cabbage looper, *Trichoplusia ni*, were obtained from Entopath, Inc. (Easton, Pa.). The eggs were hatched and larvae reared according to the directions provided by the manufacturer, and fourth instar larvae were used for baculovirus infection.

Larvae Infection

Various amounts of baculovirus stock solution, consisting of occluded recombinant virus were spread on the larval diet, which was ordered premade in Styrofoam cups from Entopath, Inc. (Easton, Pa.). The cups were covered and allowed to stand for an hour so that the virus was completely absorbed by the media. The fourth instar larvae were then placed into the cups (approximately 10 to 15 larvae per cup), and the cups were inverted. The larvae fed from the top (bottom of cup) so that fecal matter dropped on to the lid where it was discarded daily. The quantity of food was sufficient for at least 5 days of growth. Three to five larvae were collected daily for RX3-DsRED and DsRED analysis.

SF9 Infection

*Spodoptera* Sf9 cell cultures were obtained from Invitrogen (San Diego, Calif., U.S.A.) and cultured as previously (O'Reilly et al., 1992) using Grace's insect medium supplemented with lactalbumin hydrolysate, yeastolate, L-glutamine, 10% heat-inactivated fetal bovine serum and 1% penicillin/streptomycin solution (Gibco). Cells were grown in either spinner flasks (Bellco Glass, Vineland, N.J., U.S.A.) or 100 mm plastic tissue culture dishes (Falcon). Recombinant virus was produced using the BaculoGold Transfection Kit (PharMingen, San Diego, Calif., U.S.A.). Single plaques were isolated and amplified two to four times to obtain a high-titer viral stock which was stored at 4° C. until use. For routine infection, Sf9 cells in Grace's medium were allowed to attach to the bottom of a 100 mm plastic culture dish ($10^7$ cells/dish). After incubation for 15 min to 1 h, a portion of viral stock was added and the cultures were maintained at 27° C. in a humidified air atmosphere. Cells were typically used at 30-36 hours after infection.

Example 21

RPBLAs Preparation from Mammal Cells and Insect Larvae

Homogenization

Mammalian Cells

Transfected cells were recovered from culture plates by scraping and were suspended in the homogenization B medium (10 mM Tris-HCl pH 8.0, 0.9% NaCl, 5 mM EDTA with protease inhibitors). The cell suspension was aspirated into a 5 ml syringe fitted with a 23 gauge needle and it was taken up and expelled approximately 30 times. Cell rupture was monitored by a phase contrast microscope.

Insect Larvae

Frozen *Trichoplusia ni* larvae expressing RX3-DsRED and DsRED proteins were homogenized in PBP5 buffer (20 mM Hepes pH 7.5, 5 mM EDTA) by polytron for 2 minutes at 13500 rpm and/or by Potter for 5 minutes in ice at 2000 rpm. This homogenate was centrifuged at 200 g 10 minutes to remove cuticle and tissue debris and the supernatant was loaded on a density step-gradient.

RPBLAs Isolation by Density

RPBLAs from mammal cells and frozen insect larvae were isolated essentially as described for plants (density step gradient or low-speed centrifugation).

Example 22

Solubilization by Triton X-114-Based Biphasic Separation

Cell homogenates were diluted with PBS and centrifuged at 16,000×g for 15 minutes. The supernatant was removed and the pellet dried. 2 ml of ice cold Solubilization Buffer (50 mM Tris pH 7, 5% Triton X-114, 20 mM TCEP, 20 mM NDSB195 and 100 mM $MgCl_2$) was added to the pellet followed by 1 ml of PBS containing 1M Urea, 10% Glycerol and 100 mM $MgCl_2$. This composition was incubated on ice for 15 min with occasional vortexing. The suspension was then sonicated for 20 seconds×4 at 50% potential, keeping it on ice between bursts for 1 minute to maintain cold temperature. The suspension was then incubated at 37° C. for 15 minutes to form the 2 phases. Three ml of 10% PEG were added to the lower hydrophobic layer (Triton X-114 rich) and the composition was incubated on ice for 20 minutes. The solution was then incubated at 37° C. for 15 minutes to re-form the 2 phases. The upper phase (4 ml) was recovered and stored for analysis.

Example 23

Immunolocalization

Immunocytochemistry was performed two to four days after transfection using a fluorescent microscope (Vertical Eclipse Microscope Nikon E600A). Cells were fixed for 30 minutes in a 1% paraformaldehyde solution, washed with phosphate saline buffer, and incubated for 45 minutes with antibodies raised against either (i) hGH (dilution 1/150), (ii) EK (dilution 1/500), or (iii) RX3 (dilution 1/700). In order to detect the antigen-antibody reaction, cells were incubated for 45 minutes with anti-rabbit antisera conjugated to Alexa Fluor 488 (Invitrogen).

Confocal analysis was performed using a Confocal laser scanning microscope (Leica TCS SP, Heidelberg, Germany) fitted with spectrophotometers for emission band wavelength selection. Green fluorescent images were collected following excitation at 488 nm with an Argon ion laser using an emission window set at 495-535 nm. Red fluorescent images were collected using 543 nm excitation with a HeNe laser and emission window of 550-600 nm. Optical sections were 0.5 to 1 µm thick.

Example 24

Activity Assays

EGF Activity Assay

MDA-MB231 breast cancer cells over-expressing the human EGF receptor were seeded in 96-well plates at 5,500 cells/well. Cells were allowed to adhere for 8 hours in growth medium supplemented with 10% FCS (Fetal calf serum) and then starved overnight in medium with 0.1% of FCS. Afterwards, the medium was removed and the positive-control EGF from Promega or the corresponding experimental sample (solubilyzed RX3-EGF) was added at different concentrations. Radioactive thymidine was added to a final concentration of 0.5 µCi. The cells were washed twice with cold PBS and kept on ice to stop the cell metabolism, and proliferation was studied at 48 hours after stimulation at 37° C. A 10% trichloroacetic acid (TCA) solution was added, and the cells were incubated for 20 minutes at 4° C. Once the TCA solution was removed, the plates were washed twice with 70% Ethanol, and the cells were incubated for 20 minutes at 37° C. in 0.5 mL of lysis solution (2% $CO_3Na_2$, 0.1N NaOH and 10% SDS). Plates were mixed by vortex agitation and the sample was not measured before 12 hours to avoid undesired chemo-luminescent phenomena.

EK Activity Assay

The enzymatic activity was measured by fluorometric assay (Grant et al. (1979) *Biochim. Biophys. Acta* 567:207-215). The reaction was initiated by adding the enzyme to 0.3 to 1.0 mM of the fluorogenic substrate Gly-(Asp)4-Lys-β-naphtylamide (Sigma) in 25 mM Tris-HCl (pH 8.4), 10 mM $CaCl_2$, 10% DMSO (dimethyl sulfoxide) at 37° C. Free β-naphtylamine concentration was determined from the increment of fluorescence ($\lambda ex=337$ nm and $\lambda em=420$ nm) continuously monitored for 1 minute. The activity was calculated as change in fluorescence over time.

GUS Activity Assay

GUS activity assay is based in the catalysis of metilumbeliferil-β-glucuronide acid (MUG) to the 4-metilumbeliferone (4-MU) fluorescent product, by the GUS enzyme (Jefferson et al. 1987 *EMBO J.* 6(13):3901-3907). 50 µL of solubilyzed RX3-GUS (or solubilyzed RX3 as a control) was added to 200 µL of Reaction buffer (50 mM of phosphate buffer pH 7, 10 mM EDTA, 0.1% SDS and 0.1% Triton X100) plus 66 µL of Methanol. The substrate (MUG) was added to a final concentration of 10 mM. The standard was prepared by adding 0, 50, 100, 200, 300 or 500 pmols of 4-MU (the product of the reaction) to 200 µL of Reaction buffer of the reaction (4-MU).

The samples and the standard were mixed and they were measured in a fluorimeter (Victor, Perkin-Elmer) at $\lambda ex=355$ nm and $\lambda em=460$ nm. The samples were measured each 30 minutes for 3 hours. The specific activity was calculated by the formula: GUS activity (pmols 4-MU/min-1*mg-1)=($\lambda em$ (T1)−($\lambda em$(T0))/(k*(T1−T0)). "K"=ratio (Units of fluorescence)/(pmol 4-MU).

RTB Activity Assay (Asialofetuin-Binding ELISA)

The functionality of RX3-RTB in the protein extracts from RPBLAs was determined via binding to asialofetuin, the glycoprotein fetuin treated with sialydase to expose galactose-terminated glycans. Two hundred microliters of asialofetuin (Sigma) at a concentration of 300 mg/mL in modified PBS (mPBS) buffer (100 mM Na-phosphate, 150 mM NaCl, pH 7.0) was bound to the wells of an Immulon 4HBX (Fisher, Pittsburgh, Pa.) microtiter plate for 1 hour at RT. The coating solution was discarded and the wells blocked with 200 ml 3% BSA, 0.1% Tween 20 in mPBS for 1 hour at RT. After the blocking solution was discarded, 100 ml of RTB standards and protein extracts (see below) were applied and incubated for 1 hr at RT. The wells were then washed three times with 200 ml PBS, 0.1% Tween 20. Rabbit anti-*R. communis* lectin (RCA60) polyclonal Ab (Sigma) at 1:4000 in blocking buffer (as above) was applied and incubated for 1 hour at RT. The wells were then washed as before. AP-conjugated goat-anti-rabbit IgG (Bio-Rad) was applied at a dilution of 1:3000 in blocking buffer and incubated for 1 hour at RT. The wells were washed three times as described above and 100 ml pNPP (p-nitrophenyl phosphate disodium salt) substrate (Pierce, Rockford, Ill.) was applied. The reaction was stopped after 15 minutes by the addition of 50 µl of 2N NaOH. Absorbance ($A_{405}$) was read in a Bio-Tek EL808 Ultra Microplate Reader. Protein extracts were prepared at a ratio of 1 g FW leaf to 3 ml of Tris-acorbate buffer (above), and the samples compared against a standard curve consisting of serially-diluted castor bean-derived RTB (Vector Labs, Burlingame, Calif.) in Tris-acorbate buffer, with the concentrations ranging from 5 ng to 500 ng per well.

Example 25

Enhanced Uptake of RX3-DsRED Assembled in RPBLAs from Insect Larvae by Macrophages The cDNA coding for RX3-DsRED and DsRED were cloned in the baculovirus FastBac vector (Invitrogen) to obtain pFB-RX3-DsRED and pFB-DsRED. These constructs were used to infect *Trichoplusia ni* larvae. Frozen larvae expressing RX3-DsRED and DsRED proteins were homogenized and loaded on a density step gradient. After centrifugation at 80000×g in a swinging-bucket for 2 hours, the analysis of the RX3-DsRED fusion protein and the control corresponding to DsRED expressed in the cytosol was performed by immunoblot (FIG. 2C). As expected, when expressed in the larval cells cytosol, the DsRED protein did not assemble in highly dense structures and was localized in the supernatant and the F35 fraction (FIG. 2C, lane 2 and 3). On the other hand, RX3-DsRED fusion protein was able to assemble and accumulate in dense structures that can be isolated from F56 (FIG. 2C, lane 5). As shown by confocal microscopy analysis in Example 4 (FIG. 4), the RX3-DsRED accumulated in round-shaped RPBLAs.

The RPBLAS of RX3-DsRED from F56 were diluted 3-fold in PBP5 (10 mM HEPES pH 7.4, 2 mM EDTA) and collected in the pellet by centrifugation at 80000×g at 4° C. in a swinging-bucket for 2 hours. The pellet was resuspended in PBS buffer and the number of RPBLAs was quantified by FACS. From one larva infected with the pFB-RX3-DsRED vector, approximately 1×10⁹ RPBLAs particles were obtained at a concentration of 500,000 RPBLAs per microliter (µl).

It has been reported that antigen presentation by the antigen presentation cells (APC) such as macrophages and dendritic cells is a key process necessary to induce an immune response (Greenberg et al, *Current Op. Immunology* (2002), 14:136-145). In this process, the APC takes up (phagocytoses) the antigen, which is subsequently cleaved into small peptides in the phagolysosome. These peptides interact with the major histocompatibility II (MHCII) protein and are sorted to the plasma membrane to be presented to the cell- and antibody-mediated immunity responses (Villandagos et al., *Immunological Reviews* (2005) 207:101-205).

To determine the antigenicity of RX3 fusion proteins present inside the RPBLAs, a macrophage cell culture was incubated with these organelles at different RPBLA/cell ratios (100:1 and 1000:1). The macrophage cell cultures were grown on starved conditions or in the presence of GM-CSF. These cell cultures were incubated with RPBLAs for 1 hour, and 1, 2, 5 and 10 hours after RPBLA removal the macrophages were extensively washed with PBS and fixed with 2% paraformaldehyde. Afterwards, these fixed macrophages were analyzed by FACS to quantify the amount of fluorescent RPBLAs up taken by the macrophages as well as the percentage of macrophages that had phagocytosed the fluorescent RX3-DsRED RPBLAs Percentage of Fluorescent Macrophages

| Time (hours) | Starved (RPBLA/cell ratio 100:1) | | M-CSF (RPBLA/cell ratios 100:1) | | M-CSF (RPBLA/cell ratio 1000:1) | |
|---|---|---|---|---|---|---|
| | Mean | STD | Mean | STD | Mean | STD |
| zero | 1.19 | 1.21 | 0.82 | 0.35 | 0.82 | 0.35 |
| 1 | 65.42 | 2.29 | 65.19 | 3.2 | 85.78 | 1.65 |
| 2 | 79.64 | 1.66 | 75.08 | 3.94 | 91.55 | 1.5 |
| 5 | 91.85 | 2.17 | 87.68 | 1.58 | 91.53 | 1.09 |
| 10 | 88.91 | 0.7 | 90.54 | 1.59 | 94.4 | 0.08 |

From these results, it is clear that the macrophages phagocytosed the RX3-DsRED RPBLAs with an unexpected avidity. Even at the lower RPBLAs/cells ratio (1:100) and in the presence of M-CSF, at 1 hour after RPBLAs addition, 65% of macrophages are fluorescent. Even the presence of a mitogenic cytokine, such as M-CSF, which has a negative effect on macrophage phagocytosis could not impair significantly the RPBLA uptake. At 5 hours, almost all (more than 80%) of the macrophages were fluorescent, meaning that the majority of the cells had up taken some RPBLAs from the medium.

When the amount of fluorescence associated with the macrophages was analyzed over the time of incubation, the results were even more surprising, as no saturation of the capacity of the macrophages to uptake the RPBLAs was observed. If the results of the Tables above and below are compared at 5 and 10 hours of incubation, it is seen that almost all the macrophages are fluorescent, but there is a continuous increase in the total fluorescence associated with the macrophages. This result is consistent with the macrophages phagocytosing a large quantity of fluorescent RPBLAs particles.

Time Dependent Macrophage Fluorescence

| Time (hours) | Starved (RPBLA/cell ratio 100:1) | | M-CSF (RPBLA/cell ratios 100:1) | | M-CSF (RPBLA/cell ratio 1000:1) | |
|---|---|---|---|---|---|---|
| | Mean | STD | Mean | STD | Mean | STD |
| 0 | 0.975 | 0.31 | 0.725 | 0.1 | 0.725 | 0.1 |
| 1 | 8.9 | 0.42 | 10.3 | 1.13 | 24 | 1.7 |
| 2 | 16.35 | 0.07 | 16.25 | 0.5 | 41.5 | 0.3 |
| 5 | 64.65 | 2.05 | 42.35 | 4.45 | 93.3 | 2.2 |
| 10 | 120.7 | 1.84 | 79.9 | 5.66 | 125.65 | 13.08 |

To demonstrate that RPBLAs containing the RX3-DsRED fusion protein were inside the macrophages and not simply adsorbed externally to the plasma membrane, confocal microscopy analysis was performed. FIG. 7A (left panel) shows macrophage cells incubated with RX3-DsRED particles (at 100:1) for 1 hour. On the left panel of the same figure, a section of 1 micrometer of the same cells shows the typical green auto-fluorescence of macrophages observed with a green filter (FIG. 7A, white arrowhead). The presence of the nucleus and the red-fluorescent RPBLA particles (FIG. 7A, black arrowhead) in the same optical section indicates that the RPBLAs had been taken up inside the cells.

Another important factor to be analyzed is protein degradation following macrophage phagocytosis. Antigen degradation is needed to produce the antigenic peptides that are presented on the MHCII receptor. Analysis of the DsRED fluorescent pattern of the macrophages over time is consistent with the RPBLA particles being actively digested.

Another set of micrographs shows that after 1 hr of incubation, the RPBLA particles were still not fully degraded and could still be observed inside the cells (FIG. 7B, upper panels). After 10 hours, the red fluorescence pattern was more homogenous, however, indicating that the macrophages had begun to degrade the RPBLA particles (FIG. 7B, bottom panels).

Example 26

Enhanced Uptake of RX3-DsRED in RPBLAs from Insect Larvae by Dendritic Cells

To assess the capacity of dendritic cells to phagocytose RX3-DsRED fusion proteins assembled in RPBLAs from insect larvae, a dendritic cell culture was incubated with these organelles at a 100 RPBLAs/cell ratio. Two kinds of RPBLAs were prepared: (i) RPBLAs isolated as described previously and (ii) the same RPBLAs washed in 50 mM Tris pH 8, 1% Triton X-100, in order to remove the surrounding membrane.

The dendritic cell cultures were grown on starved conditions in the presence of RPBLAs, and samples were analyzed at 0, 1, 2, 5 and 10 hours.

Percentage of Fluorescent Dendritic cells

| Time | % of fluorescent dendritic cells | | | |
|---|---|---|---|---|
| | RPBLAs | | Membrane-less RPBLAs | |
| (hours) | Mean | STD | Mean | STD |
| 0 | 1.43 | — | 1.41 | — |
| 1 | 26.76 | — | 36.46 | 0.28 |
| 2 | 33.79 | 0.6 | 50.785 | 0.21 |
| 5 | 45.845 | 0.07 | 67.275 | 3.4 |
| 10 | 61.885 | 5.73 | 74.97 | 4.17 |

Time Dependent Dendritic cells Fluorescence

| Time | Fluorescence associated ot dendritic cells | | | |
|---|---|---|---|---|
| | RPBLAs | | Membrane-less RPBLAs | |
| (hours) | Mean | STD | Mean | STD |
| 0 | 0.5 | — | 1.1 | — |
| 1 | 3.1 | — | 5.1 | 0.28 |
| 2 | 3.55 | 0.6 | 5.05 | 0.21 |
| 5 | 25.15 | 0.07 | 54 | 3.4 |
| 10 | 37.05 | 5.73 | 74.05 | 4.17 |

As can be concluded from Tables above, the dendritic cells show a surprising avidity for RPBLAs. As expected, they have a slower phagocytosis rate compared to the macrophages (compare the previous tables), as is described elsewhere. The percentage of fluorescent dendritic cells increases all along the time course analyzed, and no saturation effect was observed even at 10 hours after RPBLAs incubation. Similar conclusions can be drawn when the amount of fluorescence associated with the macrophages over time was analyzed.

The dendritic cells' capacity to take up the RPBLAs did not exhibit a saturation effect. This lack of effect can be explained by the fact that more and more dendritic cells are induced to phagocytosis (and becoming fluorescent) over time. Nevertheless, it is also possible that the phagocytosis capacity of individual cells is not saturated, as has been observed with macrophages.

Unexpectedly, the FACS analysis of dendritic cells incubated with membrane-less RPBLAs showed a significantly higher percentage of fluorescent dendritic cells than the same cells incubated with membrane-containing RPBLAs. Moreover, the fluorescence of these dendritic cells was also higher as well. Similar results were obtained using macrophages with membrane-less RPBLAs. This was somewhat surprising as it was expected that the presence of insect-derived membrane proteins in the membrane-containing RPBLAs would be recognized as foreign proteins by the murine dendritic cells, and hence enhance phagocytosis. It is thus apparent that insect-derived RPBLAs in the presence or absence of the surrounding membrane are very efficient antigen presentation vehicles.

To demonstrate that RPBLAs and membrane-less RPBLAs containing the RX3-DsRED fusion protein were taken up by the dendritic cells, optical microscopy analysis was done. FIG. 8A (upper) shows dendritic cells incubated for 2, 5 and 10 hours with RX3-DsRED RPBLAs (100:1 ratio). On the bottom of FIG. 8B, the red fluorescence of the DsRED protein illustrates the uptake of the RPBLAs by those cells. At 2 hours of incubation, some phagocytosis can be observed, but most of the RPBLAs are only adsorbed to the plasmatic membrane. At 5 hours, and even more at 10 hours, many phagocytosed red fluorescent RPBLAs were observed. Similar results were obtained when dendritic cells were incubated with membrane-less RPBLAs (FIG. 8B).

It is important to note that even at 10 hours of incubation with RPBLAs or membrane-less RPBLAs, most of the phagocytosed particles remained visible as particles, meaning that little proteolysis had take place. This observation agrees with previous observation showing that the kinetics of protease acquisition, and hence, of proteolysis, is slower in dendritic cells than in macrophages (Lennon-Dum'enil et al. (2002) *J. Exp. Med.* 196:529-540). These conditions may limit the proteolysis of proteins in dendritic cells and favor the generation of peptide antigens of appropriate length for loading onto MHC class II molecules.

Example 27

Phagocytosis of Macrophages and Dendritic Cells

Macrophages

Macrophages were obtained from the marrow of Balb/C mice. Mice were sacrificed by a cervical dislocation and femur and tibia were extracted. The bones were cut and the marrow was extracted with DMEM medium using a syringe. The marrow was cultivated on a 150 mm Petri plate with complete DMEM medium (supplemented with 20% FCS and 30% L-cell). A murine macrophage culture of 99% purity was obtained after 7 days of incubation at 37° C.

The differentiated macrophages were cultivated in complete medium to give rise 350,000 cells per well. When the cells were adhered, the medium was removed and cells were incubated with new medium that contained RX3-DsRED RPBLAs from larvae. The experiment was repeated with either 100 or 1000 particles per cell. The number of particles (RPBLAs) was counted by Coulter Epics XL FACS using an Argon laser at 488 nm for excitation and FL2 at 575 nm+/−30 for emission. Flow-count from Beckman Coulter ref. 7547053 (lot 754896F) was used to verify the flow.

After 0, 1, 2, 5 and 10 hours the medium was removed and two washings with PBS were performed. Cells were permitted to recuperate and then were fixed with 2% paraformaldehyde in PBS. The treated macrophages were stored at 4° C. and the cell fluorescence was analyzed by FACS using the same program as for counting.

Immunohistochemistry was performed to verify that RX3-DsRED particles were located inside the cells following phagocytosis. The differentiated macrophages (50,000 cells/well) were incubated with 100:1 particles of RX3-DsRED for 1 hour. After incubation, cells were washed twice with PBS and fixed with PBS/2% formaldehyde for 15 minutes. Treated cells were analyzed by confocal microscopy.

Dendritic Cells

The marrow from Balb/C mice was cultivated with complete medium (DMEM, 10% FCS, 5 ng/ml GM-CSF) for one day. In order to remove granulocytes, plates were agitated and medium was changed twice. Medium was then changed twice without agitation and plates were incubated 2 days to obtain immature dendritic cells. Dendritic cells were incubated with 100:1 particles of RX3-DsRED for 1, 5 and 10 hours. After treatment, cells were fixed with 2% paraformaldehyde, stored at 4° C. and the fluorescence was analyzed by FACS.

Each of the patent applications, patents and articles cited herein is incorporated by reference. The use of the article "a" or "an" is intended to include one or more.

The foregoing description and the examples are intended as illustrative and are not to be taken as limiting. Still other variations within the spirit and scope of this invention are possible and will readily present themselves to those skilled in the art.

What is claimed:

1. A method of preparing a biologically active enzyme composition, said method comprising:
   a) providing a recombinant protein body (PB) assembly formed in an isolated animal cell or multi-cellular fungal cells, wherein the recombinant PB assembly comprises a membrane-enclosed fusion protein, said fusion protein comprising a protein body-inducing sequence (PBIS) and a biologically active enzyme;
   b) contacting the recombinant PB assembly with an aqueous buffer containing a membrane-disassembling amount of a surfactant;
   c) maintaining said contact for a time period sufficient to disassemble the membrane and at a temperature that does not denature the biologically active enzyme, to separate the membrane from the fusion protein to produce a membrane-less recombinant PB assembly that contains the biologically active enzyme;

d) collecting the membrane-less recombinant PB assembly that contains the biologically active enzyme; and e) contacting a substrate of the enzyme with the membrane-less recombinant PB assembly, to form the biologically active enzyme composition.

2. The method according to claim 1 wherein the membrane-less recombinant PB assembly exhibits the biological activity of said biologically active enzyme.

3. The method according to claim 1 wherein said biologically active enzyme is linked to said PBIS by a spacer amino acid sequence that is cleavable by enzymatic or chemical means.

4. The method of claim 1, wherein the PBIS comprises a prolamin sequence.

5. The method of claim 4, wherein the prolamin sequence comprises a gamma-zein RX3 sequence.

6. The method of claim 1, wherein the animal cell is a mammalian cell.

7. The method of claim 6, wherein the mammalian cell is a CHO cell, COS cell, or 293T cell.

8. The method of claim 1, wherein the animal cell is an insect cell.

9. The method of claim 8, wherein the insect cell is a *Spodoptera frugiperda* cell or a *Trichoplusia* cell.

10. The method of claim 1, wherein the enzyme is a hydrolase or oxido-reductase.

11. The method of claim 10, wherein the hydrolase is a glycosidase, cellulase, or phytase.

12. A method of delivering an enzyme to a substrate, said method comprising contacting a substrate of an enzyme with a membrane-less recombinant PB assembly, wherein the membrane-less recombinant PB assembly comprises a fusion protein, wherein the fusion protein comprises the enzyme and a PBIS, and wherein the enzyme is biologically active.

13. The method of claim 12, wherein the recombinant PB assembly is produced in an isolated animal cell.

14. The method of claim 13, wherein the animal cell is a mammalian cell.

15. The method of claim 13, wherein the animal cell is an insect cell.

16. The method of claim 12, wherein the recombinant PB assembly is produced in a higher plant cell.

17. The method of claim 12, wherein the PBIS comprises a prolamin sequence.

18. The method of claim 17, wherein the prolamin sequence comprises a gamma-zein RX3 sequence.

19. The method of claim 12, wherein the enzyme is a hydrolase or oxido-reductase.

20. The method of claim 19, wherein the hydrolase is a glycosidase, cellulase, or phytase.

* * * * *